United States Patent
Shirley

(10) Patent No.: US 7,399,904 B2
(45) Date of Patent: Jul. 15, 2008

(54) CASEIN KINASE STRESS-RELATED POLYPEPTIDES AND METHODS OF USE IN PLANTS

(75) Inventor: Amber Shirley, Wake Forest, NC (US)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 11/737,826

(22) Filed: Apr. 20, 2007

(65) Prior Publication Data

US 2008/0050820 A1    Feb. 28, 2008

Related U.S. Application Data

(60) Division of application No. 10/904,588, filed on Nov. 17, 2004, now abandoned, which is a continuation-in-part of application No. 09/828,313, filed on Apr. 6, 2001, now Pat. No. 6,867,351, which is a continuation-in-part of application No. 10/904,588, which is a continuation-in-part of application No. 10/292,408, filed on Nov. 12, 2002, now Pat. No. 7,176,026.

(60) Provisional application No. 60/346,096, filed on Nov. 9, 2001, provisional application No. 60/196,001, filed on Apr. 7, 2000.

(51) Int. Cl.
    *A01H 5/00*    (2006.01)
    *C12N 15/82*    (2006.01)
    *C12N 15/87*    (2006.01)
    *C12N 5/14*    (2006.01)
    *C07H 21/00*    (2006.01)

(52) U.S. Cl. .................... 800/295; 435/320.1; 435/419; 435/468; 536/23.6

(58) Field of Classification Search ............... None
    See application file for complete search history.

(56) References Cited

OTHER PUBLICATIONS

Kotani et al., NCBI, GenBank, Sequence Accession No. AB012246, Published Aug. 9, 2000.*

* cited by examiner

*Primary Examiner*—Phuong T. Bui
*Assistant Examiner*—Vinod Kumar
(74) *Attorney, Agent, or Firm*—Patricia A. McDaniels

(57) ABSTRACT

A transgenic plant transformed by a casein kinase Stress-Related Polypeptide (CKSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated CKSRPs, and isolated nucleic acid coding CKSRPs, and vectors and host cells containing the latter.

22 Claims, 11 Drawing Sheets

PpCK-1 Freezing

Control Freezing

```
                            301                                                                                         400
         Orf 760      (233) RDDIESLGHVFFYFIRGSLPWQG---LKAPNNKLKYEKIGMTKQLNPDDLLLNNAIPYQFATYLKYARSLKFDEDPDYDYIISLMDDALRLNDLKDDGH
AAB68417 (yeast YCKI) (255) RDDIESLGHVFFYFIRGHLPWQG---LKAPNNKQKYEKIGEKKRSTNVYDLAQG---LPVQFGRYLEIVRSLSFEECPDYEGYRLLLSVLDDLGETADGQ
AAA35230 (yeast YCK2) (262) RDDMEAIGHVFFYFIRGQLPWQG---LKAPNNKQKYEKIGEKKRLTNVYDLAQG---LPIQFGRYLEIVRNLSFETPDYEGYRMLLSVLDDLGETADGQ
         EST 263      (193) RDDIESLGVVLMYFLRGNLPWQG---LKAGTKKQKYEKISEKRMSTPLEVLCKN---YPSEFASYFHYCRSLRFDDKPDYAYLKRRLFRDLFIREGFQFDYV
         EST 194      (265) RDDIESLGVNILMYFLRGNLPWQGGKGGQRLTDQKQHEYMHNKIRMNTTVEELCDG---YPSQFADFLHEARSLGFYEQPDYCYLRSLFRDLFIQKKFQLDHV
         EST 289      (193) RDDIESLGVVLMYFLRGSLPWQG---MKAGTKKQKYEKISEKRMSTPLEFICKA---YPSEFASYFHYCRSLRFDDKPDYAYLKRLERDLFIREGFQFDYV
AAH06490 (human CKI epsilon)(193) RDDIESLGVVLMYFLRGSLPWQG---LKAATKROKYEKISEKRMSTPLEVLCKG---YPSESTYENECRSLRFDDKPDYSYLRQFRNLFHQGFSVDYV
AAH03558 (human CKI delta) (193) RDDIESLGVVLMYTNLGSLPWQG---LKAATKROKYEKISEKRMSTPIEVLCKG---YPSEATYLNECRSLRFDDKPDYSYLRQFRNLFHQGESLDYV
AAH08717 (human CKI alpha) (201) RDDMESLGVVLMYFNRTSLPWQG---LKAATKKQKYEKISEKRMSTPVEVLCKG---FPAEFAMYLANVCRGLRFEAPDYMYLRQFRLLFFRTLNHQYDYT
AAD26525 (human CKI gamma) (229) RDDMEAIGHMFMYFIRGSLPWQG---LKADTLKERYQKIGDTKRATPLEVLCEN---FP-EMATYLRRYVVRLGFFYKPDYEYLRKLETDLFEDKGYMEDYE
         EST 142      (265) RDDIESLGVILMYFIRGNLPWQGGQGQRFTDQKQHEYMHNKIRMETTLEEDICDG---YPRQFADFLHHARELGFYEQPDYSVLESLFRDLFIQKKFQLDHV
AJ487966 (rice CK1)   (193) RDDIESLGVVLMYFIRGSLPWQG---LKAGTKKQKYKDKISEKKMLTPVEVLCKS---YPTEFISYFHYCRSLRFEDKPDYSYLRFRDLFIREGYQLDYI 401                                                                                         500
         Orf 760      (330) YDWMDENGGKGWNIKINRRANLHGYGNPNPRVNGNTARNNVN------TNSKTRNTTPVATPKQQ------NSYNKDNSKSRISSN
AAB68417 (yeast YCKI) (350) YDWMKINDGRGWDLNINKKPNLHGYGHPNPPNEKSRKHRNK------QLQMQQLQMQQLQQQQ------QYAQKTEADMRNSQY
AAA35230 (yeast YCK2) (357) YDWMKENGGRGWDLSINKKPNLHGYGHPNPPNEKSRKHRSKNHQYSSPDHHHHYNQQQQQQQA------QA------QAQAQAQAKVQQQQL
         EST 263      (288) FDWTHKYQQSQISGG------SSTRLGASAGQTSGALGTGATGSRDLQRPTEPMDPSRRRLPGANGSGVANALDSSKHKSPGLDESA-KDSALAVVSEP
         EST 194      (363) YDWIVNTQ------LPQNGSLQSVRS------ONSASSHLQN
         EST 289      (288) FDWTIEKYQQTHFSGG---PLRPAAAAGGSSGAAAAAAGIGTVPRDAQRAIEPTDVAARTRMVGATRSSGLNPLDASRHKSTSPDEAASKDIALSGLAEP
AAH06490 (human CKI epsilon)(288) FDWNMLFGAARNPED------VDRERREHERE------ERMGQLRGSATRALPPGPPTGA------TANRLRSAAEP
AAH03558 (human CKI delta) (288) FDWNMLKFGASRAADD------AERERR--DRE---ERLRHSRNPATRGLP---ST------ASGRLRGTQEV
AAH08717 (human CKI alpha) (296) FDWNMLKQKAAQQAAS------SSGQGQ------QAQTPTGKQTDK------TKSNMKGF--
AAD26525 (human CKI gamma) (323) YDWIGKQLPTP--VG------AVQQDPALSSNRE------AHQHRDKMQQSKNQS
         EST 142      (363) YDWIVNTQ------PPQNGSAQTVRS------PAAGPQTHLQS
AJ487966 (rice CK1)   (288) EDWTIKQGSESNRLRSSGR---TSGLVGPSAERTERAAARQDVP------DRFSGTVDPFFARRTSGSGSHYG------EHTKHRNILDSLLAPKTAVDLDKRRP 501                                                                                         600
         Orf 760      (406) PQSFTRQQHVLKKIEPNSKYIPETHSNLQRPIKSQSQTYDSISHTQNSPFVPYSSSKANPKRSNNEHNLPNHYTNLANKNINYQSQRNYEQENDAYSDDE
AAB68417 (yeast YCKI) (425) KPKLDPESYEAYQHQQQKYEQQQK-RQQQQKLQEQQLQEQQLQQQQQQQQLRATGQPPSQPQAQTQSQQFGARYQPQQQPSAALRTPEQHPNDDNSS
AAA35230 (yeast YCK2) (437) QQAQAQQQANRYQLQPDDSHYDEER---EASKLDPTSYEAYQQQTQQKYAQQQQKQMQQKSKQFANTGANGQTNKYPYNAQPTANDEQNAKNAAQDRNS
         EST 263      (382) ERMHTSSYATRGGSSRRAVISSSRPSGASAEVVDSSRTGSSKLGPTSLRSSAGMQRSSPVTSDPKRISSRHPQPPSANLRIYEAAIKGVESLSVEVDQS
         EST 194      (394) RPSNVSYCPPLTKSEFRREVAAN------G------SVQVVSSTNGELNTDDETAGRSNAPITAPTEVEVMDETKCCCFFKRRKRKTIQRHK-
         EST 289      (386) ERTHASSFVR-GSSSSRRAVVGCARP-AGSTEAGDGTRVLAGKMGPTSLRTSAGMQRSSPVASTDPKRTGRDSYAG--NSGRNPSSSRNSKE---
AAH06490 (human CKI epsilon)(348) VASTPASRIQPAGNTSPRAISRVDRE------RKVSMRLHRGA------FANVSSSDLTGRQEVSRIPASQTSVPFDHLGK--
AAH03558 (human CKI delta) (341) APPTPLPTSHTANTSPRPVSGMERE------RKVSMRLHRGA------PVNISSSDLTGRQDTSRMSTSQIPGRVASSGLQSVVHR---
AAH08717 (human CKI alpha) (338) ------
AAD26525 (human CKI gamma) (364) ADHRAWDSQQANPHLRAHIAADRHG------
         EST 142      (394) RPSNVSYCPPLTKPEFRREVVAAN------
AJ487966 (rice CK1)   (376) ------TSSSRN--GSTSRKALILSSSRP--SSGDPIDPNRS------NLIPTESGSSRPS--TMQRLHQSTGLETRSSLTKTARNVHDDPTLRTFERLSISADRR
```

FIGURE 5 (Continued)

```
                                        601                 619
            Orf 760              (506)  NDTFCSKIYKYCCCCFCCC
AAB68417 (yeast YCKI)            (524)  LAASHKGFFQKLGCC----
AAA35230 (yeast YCK2)            (533)  NKSS-KGFFSKLGCC----
            EST 263              (482)  RYK----------------
            EST 194              (418)  -------------------
            EST 289              (474)  -------------------
AAH06490 (human CKI epsilon)     (417)  -------------------
AAH03558 (human CKI delta)       (416)  -------------------
AAH08717 (human CKI alpha)       (338)  -------------------
AAD26525 (human CKI gamma)       (448)  -------------------
            EST 142              (418)  -------------------
AJ487966 (rice CKI)              (463)  K------------------
```

| Gene name | EST | Functional Categories | Function | Assay | Relative WUE Data (% difference from controls) | | | | | | Drought Cycling Biomass (% difference from controls) | |
|---|---|---|---|---|---|---|---|---|---|---|---|---|
| | | | | | WUE vs SCO24 | WUE vs BPS C24 | DW vs SCO24 | DW vs BPS C24 | E vs SCO24 | E vs BPS C24 | Drought vs BPS C24 | Watered vs BPS C24 |
| PpPK-4 | 142 | Protein Kinase | protein kinase | E | 20 | 27 | 9 | 22 | -7 | -3 | | |
| | | | | J | 11 | 8 | 30 | 6 | 17 | -3 | | |
| | | | | P | | | | | | | 23 | 22 |
| | | | | Y | | | | | | | 24 | 14 |
| | 289 | Protein kinase | casein kinase | G | 4 | 20 | 13 | 66 | 9 | 37 | | |
| | | | | J | 4 | 1 | 32 | 7 | 31 | 8 | | |
| PpCK-2 | 263 | Protein kinase | casein kinase | A | -8 | 0 | -25 | 5 | -21 | 2 | | |
| | | | | T | | | | | | | 25 | 3.5 |
| PpCK-1 | 194 | Protein kinase | casein kinase | A | 8 | 17 | 6 | 47 | -2 | 26 | | |
| | | | | D | -5 | -17 | 12 | -22 | 14 | -5 | | |
| | | | | T | | | | | | | 78 | 43 |
| Mean for all genes | | | | | 5 | 8 | 11 | 19 | 6 | 9 | 37 | 21 |

CASEIN KINASE STRESS-RELATED POLYPEPTIDES AND METHODS OF USE IN PLANTS

CROSS-REFERENCE TO RELATED APPLICATIONS

This application is a divisional of U.S. application Ser. No. 10/904,588, filed Nov. 17, 2004 now abandoned, which is a continuation-in-part application of U.S. application Ser. No. 09/828,313, which was filed on Apr. 6, 2001 now U.S. Pat. No. 6,867,351 claiming the priority benefit of U.S. Provisional Patent Application Ser. No. 60/196,001 filed Apr. 7, 2000, and the entire contents of each such application is hereby incorporated by reference. U.S. application Ser. No. 10/904,588 is also a continuation-in-part application of U.S. application Ser. No. 10/292,408, which was filed on Nov. 12, 2002 now U.S. Pat. No. 7,176,026, claiming the priority benefit of U.S. Provisional Patent Application Ser. No. 60/346,096 filed Nov. 9, 2001, and the entire contents of each such applications is hereby incorporated by reference.

BACKGROUND OF THE INVENTION

1. Field of the Invention

This invention relates generally to nucleic acid sequences encoding polypeptides that are associated with abiotic stress responses and abiotic stress tolerance in plants. In particular, this invention relates to nucleic acid sequences encoding polypeptides that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as soybean, rice, maize (corn), cotton, and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on development, growth, and yield of most crop plants are profound. Continuous exposure to drought conditions causes major alterations in the plant metabolism, which ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold, and salt tolerance in model drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerant plants using biotechnological methods.

Drought stresses, heat stresses, cold stresses, and salt stresses have a common theme important for plant growth and that is water availability. As discussed above, most plants have evolved strategies to protect themselves against conditions of desiccation; however, if the severity and duration of the drought conditions are too great, the effects on plant development, growth and yield of most crop plants are profound. Furthermore, most of the crop plants are very susceptible to higher salt concentrations in the soil. Because high salt content in some soils results in less water being available for cell intake, high salt concentration has an effect on plants similar to the effect of drought on plants. Additionally, under freezing temperatures, plant cells lose water as a result of ice formation that starts in the apoplast and withdraws water from the symplast. A plant's molecular response mechanisms to each of these stress conditions are common, and protein kinases, such as casein kinases, play an essential role in these molecular mechanisms.

Protein kinases represent a superfamily, and the members of this superfamily catalyze the reversible transfer of a phosphate group of ATP to serine, threonine, and tyrosine amino acid side chains on target polypeptides. Protein kinases are primary elements in signaling processes in plants and have been reported to play crucial roles in perception and transduction of signals that allow a cell (and the plant) to respond to environmental stimuli. In particular, casein kinase I proteins are monomeric serine/threonine type protein kinases that contain a highly conserved central kinase domain. Members of this family have divergent N-terminal and C-terminal extensions. The N-terminal region is responsible for substrate recognition and the C-terminal extension is important for the interaction of the kinase with substrates. The C-terminal extension also is thought to be important for mediating regulation through autophosphorylation (Gross and Anderson, 1998 Cell Signal 10:699-711; Graves and Roach, 1995, J Biol Chem 270:21689-21694).

Although some genes that are involved in stress responses and water use efficiency in plants have been characterized, the characterization and cloning of plant genes that confer stress tolerance and water use efficiency remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a fundamental physiochemically-constrained trade-off, in all terrestrial photosynthetic organisms, between $CO_2$ absorption and water loss (Taiz and Zeiger 1991 Plant Physiology, Benjamin/Cummings Publishing Co, p 94). $CO_2$ needs to be in aqueous solution for the action of $CO_2$ fixation enzymes such as Rubisco (Ribulose 1,5-bisphosphate Carboxylase/Oxygenase) and PEPC (Phosphoenolpyruvate carboxylase). As a wet cell surface is required for $CO_2$ diffusion, evaporation will inevitably occur when the humidity is below 100% (Taiz and Zeiger 1991 Plant Physiology, Benjamin/Cummings Publishing Co p 257). Plants have numerous physiological mechanisms to reduce water loss (e.g. waxy cuticles, stomatal closure, leaf hairs, sunken stomatal pits). As these barriers do not discriminate between water and $CO_2$ flux, these water conservation measures will also act to increase resistance to $CO_2$ uptake (Kramer 1983 Water Relations of Plants, Academic Press p 305). Photosynthetic $CO_2$ uptake is absolutely required for plant growth and biomass accumulation in photoautotrophic plants. Water Use Efficiency (WUE) is a parameter frequently used to estimate the trade off between water consumption and $CO_2$ uptake/growth (Kramer 1983 Water Relations of Plants, Academic Press p 405). WUE has been defined and measured in multiple ways. One approach is to calculate the ratio of whole plant dry weight, to the weight of water consumed by the plant throughout its life (Chu et al 1992 Oecologia 89:580). Another variation is to use a shorter time interval when biomass accumulation and water use are measured (Mian et al 1998 Crop Sci. 38:390). Often measurements from restricted parts of the plant are used, for example, measuring only aerial growth and water use (Nienhuis et al 1994 Amer J Bot 81:943). WUE has also been defined as the ratio of $CO_2$ uptake to water vapor loss from a leaf or portion of a leaf, often measured over a very short time period (seconds/minutes) (Kramer 1983 Water Relations of Plants, Academic Press p 406). The ratio of $^{13}C/^{12}C$ fixed in plant tissue, and measured with an isotope ratio mass-spectrometer, has also been used to estimate WUE in plants using $C_3$ photosynthesis (Martin et al 1999 Crop Sci. 1775).

An increase in WUE is informative about the relatively improved efficiency of growth and water consumption, but on its own it does not describe which of these two processes (or both) have changed. In selecting traits for improving crops, an increase in WUE due to a decrease in water use, without a change in growth would have particular merit in an irrigated agricultural system where the water input costs were high. An increase in WUE driven mainly by an increase in growth without a corresponding jump in water use would have applicability to all agricultural systems. In many agricultural systems where water supply is not limiting, an increase in growth, even if it came at the expense of an increased water use (i.e. no change in WUE), could also increase yield. Therefore new methods to increase both WUE and biomass accumulation are required to improve agricultural productivity. As WUE integrates many physiological processes relating to primary metabolism and water use, it is typically a highly polygenic trait with a large genotype by environment interaction (Richards et al 2002 Crop Sci 42:111). For these and other reasons few attempts to select for WUE changes in traditional breeding programs have been successful.

There is a need, therefore, to identify genes expressed in stress tolerant plants and plants that are efficient in water use that have the capacity to confer stress tolerance and water use efficiency to its host plant and to other plant species. Newly generated stress tolerant plants will have many advantages, such as an increased range in which the crop plants can be cultivated, by for example, decreasing the water requirements of a plant species. Other desirable advantages include increased resistance to lodging, the bending of shoots or stems in response to wind, rain, pests, or disease.

SUMMARY OF THE INVENTION

This invention fulfills in part the need to identify new, unique casein kinases capable of conferring stress tolerance to plants upon over-expression. The present invention describes a novel genus of Casein Kinase Stress-Related Polypeptides (CKSRPs) and CKSRP coding nucleic acids that are important for modulating a plant's response to an environmental stress. More particularly, overexpression of these CKSRP coding nucleic acids in a plant results in the plant's increased tolerance to an environmental stress.

Therefore, the present invention includes an isolated plant cell comprising a CKSRP coding nucleic acid, wherein expression of the nucleic acid sequence in the plant cell results in increased tolerance to environmental stress as compared to a wild type variety of the plant cell. Preferably, the CKSRP is from *Physcomitrella patens, Saccharomyces cerevisiae*, or *Brassica napus*. Namely, described herein are the *Physcomitrella patens* Casein Kinase-4 (PpCK-4 or EST 289), *Physcomitrella patens* Casein Kinase-1 (PpCK-1 or EST 194), *Physcomitrella patens* Casein Kinase-2 (PpCK-2 or EST 263), *Physcomitrella patens* Protein Kinase-4 (PpPK-4 or EST 142), *Saccharomyces cerevisiae* Casein Kinase-1 (ScCK-1 or ORF 760), *Brassica napus* Casein Kinase-1 (BnCK-1), *Brassica napus* Casein Kinase-2 (BnCK-2), *Brassica napus* Casein Kinase-3 (BnCK-3), *Brassica napus* Casein Kinase-4 (BnCK-4), and *Brassica napus* Casein Kinase-5 (BnCK-5).

The invention provides in some embodiments that the CKSRP and coding nucleic acid are those that are found in members of the genus *Physcomitrella, Saccharomyces*, or *Brassica*. In another preferred embodiment, the nucleic acid and polypeptide are from a *Physcomitrella patens* or *Brassica napus* plant or a *Saccharomyces cerevisiae* yeast. The invention provides that the environmental stress can be salinity, drought, temperature, metal, chemical, pathogenic and oxidative stresses, or combinations thereof. In preferred embodiments, the environmental stress can be selected from one or more of the group consisting of drought, high salt, and low temperature.

The invention further provides a seed produced by a transgenic plant transformed by a CKSRP coding nucleic acid, wherein the plant is true breeding for increased tolerance to environmental stress as compared to a wild type variety of the plant.

The invention further provides an agricultural product produced by any of the below-described transgenic plants, plant parts, or seeds. The invention further provides an isolated CKSRP as described below. The invention further provides an isolated CKSRP coding nucleic acid, wherein the CKSRP coding nucleic acid codes for a CKSRP as described below.

The invention further provides an isolated recombinant expression vector comprising a CKSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a CKSRP coding nucleic acid, wherein expression of the nucleic acid in the plant results in increased tolerance to environmental stress as compared to a wild type variety of the plant comprising: (a) transforming a plant cell with an expression vector comprising a CKSRP coding nucleic acid, and (b) generating from the plant cell a transgenic plant with an increased tolerance to environmental stress as compared to a wild type variety of the plant. In preferred embodiments, the CKSRP and CKSRP coding nucleic acid are as described below.

The present invention further provides a method of identifying a novel CKSRP, comprising (a) raising a specific antibody response to a CKSRP, or fragment thereof, as described below; (b) screening putative CKSRP material with the antibody, wherein specific binding of the antibody to the material indicates the presence of a potentially novel CKSRP; and (c) identifying from the bound material a novel CKSRP in comparison to known CKSRP. Alternatively, hybridization with nucleic acid probes as described below can be used to identify novel CKSRP nucleic acids.

The present invention also provides methods of modifying stress tolerance of a plant comprising, modifying the expression of a CKSRP nucleic acid in the plant, wherein the CKSRP is as described below. The invention provides that this method can be performed such that the stress tolerance is either increased or decreased. Preferably, stress tolerance is increased in a plant via increasing expression of a CKSRP nucleic acid.

BRIEF DESCRIPTION OF THE DRAWINGS

FIG. 5 shows an alignment of the amino acid sequences of the five disclosed *Physcomitrella patens* and *Saccharomyces cerevisiae* casein kinases with the amino acid sequences of other known casein kinases (SEQ ID NOS 10, 47-48, 6, 4, 2, 49-52, 8, and 53, respectively in order of appearance). Amino acid residues that are conserved among each of the sequences, and those amino acid residues that are either identical or similar over some or all of the sequences, are indicated with shading.

FIG. 7 shows an alignment of the amino acid sequence of the five disclosed *Physcomitrella patens* and *Saccharomyces cerevisiae* casein kinases with the disclosed *Brassica napus* casein kinases (SEQ ID NOS 10, 12, 14, 16, 18, 20, 8, 4, 6, and 2, respectively in order of appearance). The figure also indicates the consensus sequence of casein kinase I based on the aligned sequences. Amino acid residues that are conserved among each of the sequences, and those amino acid residues that are either identical or similar over some or all of the sequences, are indicated with shading.

FIG. 8 is the drawing pertaining to Table 15: ScCK-1 (ORF 760) was overexpressed in *Arabidopsis thaliana* under the control of a constitutive promoter. The transgenic lines were assayed for dessication tolerance, measuring the average number of days of survival after the wild type control was dead (Table 7). *Please see table 15.

DETAILED DESCRIPTION OF THE INVENTION

Figure 1:
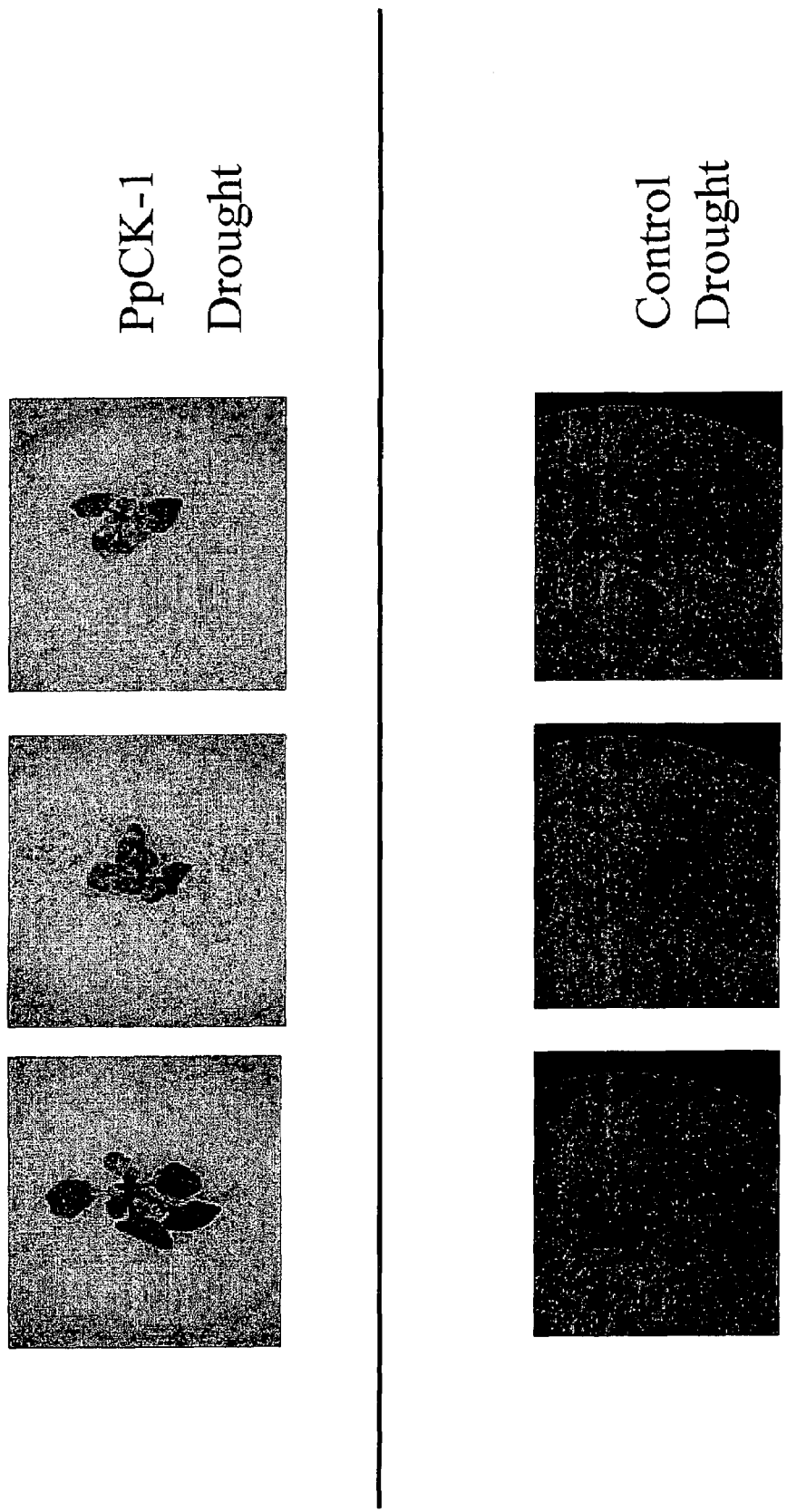
FIG. 1 shows the results of a drought stress test with over-expressing PpCK-1 transgenic plants and wild-type *Arabidopsis* lines. The transgenic lines display a tolerant phenotype. Individual transformant lines are shown.
Figure 2:
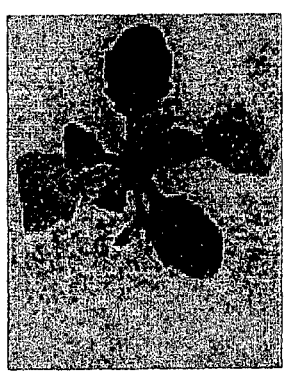
FIG. 2 shows the results of a freezing stress test with over-expressing PpCK-1 transgenic plants and wild-type *Arabidopsis* lines. The transgenic lines display a tolerant phenotype. Individual transformant lines are shown.
Figure 2:
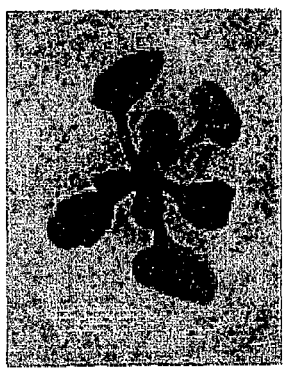
Figure 2:
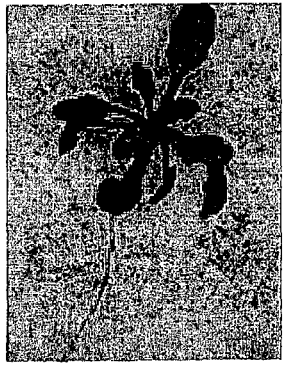
Figure 2:
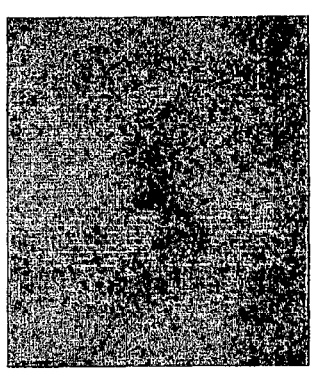
Figure 2:
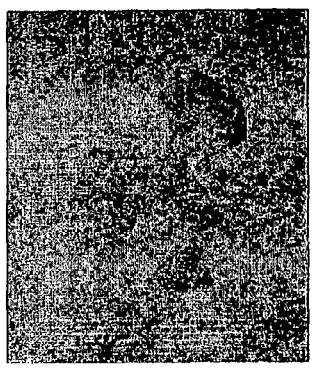
Figure 2:
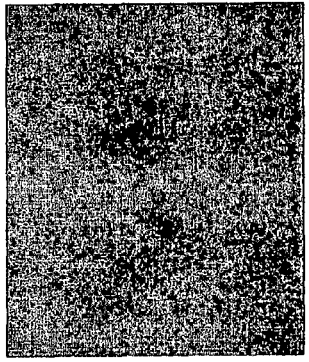
Figure 3:
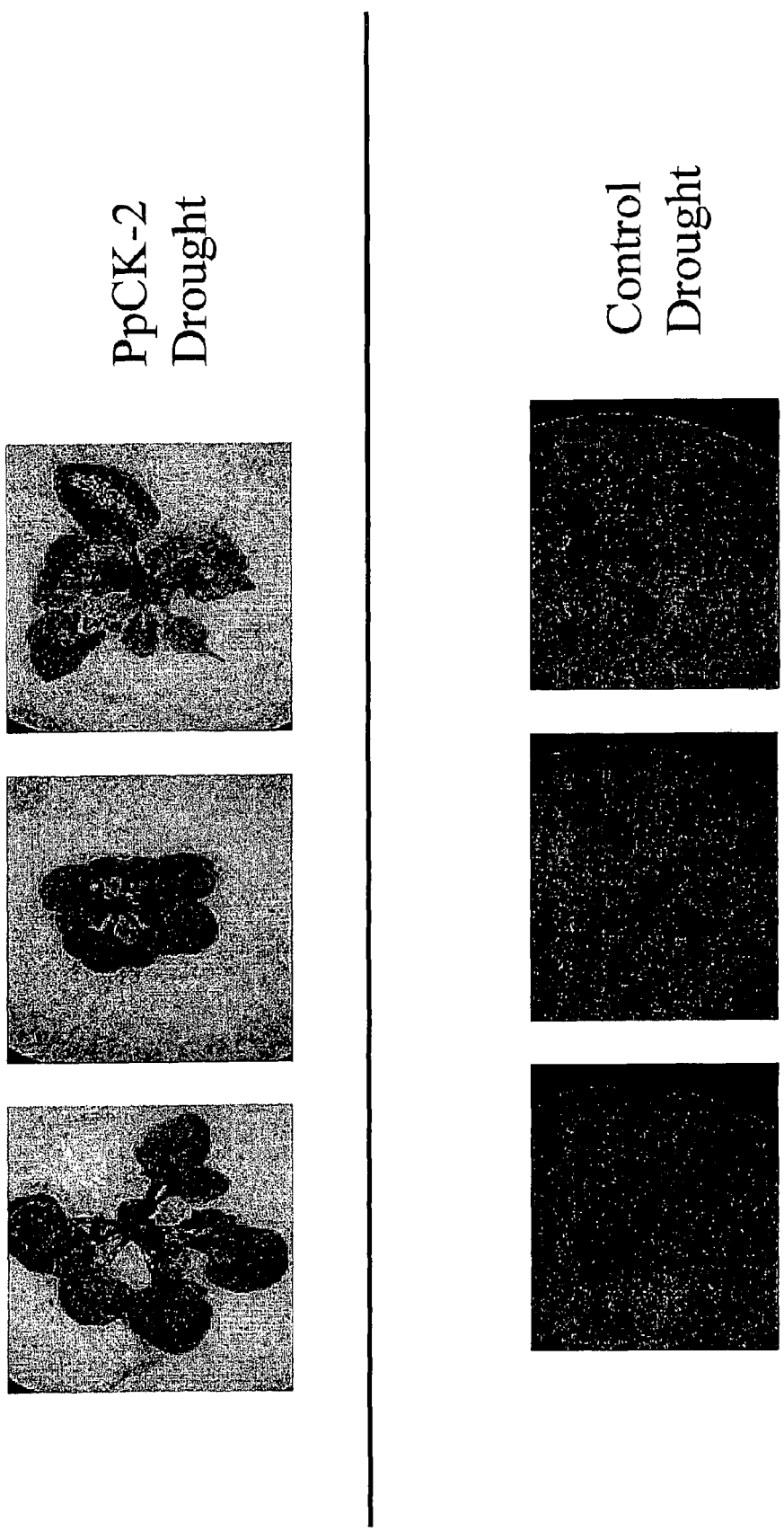
FIG. 3 shows the results of a drought stress test with over-expressing PpCK-2 transgenic plants and wild-type *Arabidopsis* lines. The transgenic lines display a tolerant phenotype. Individual transformant lines are shown.
Figure 4:
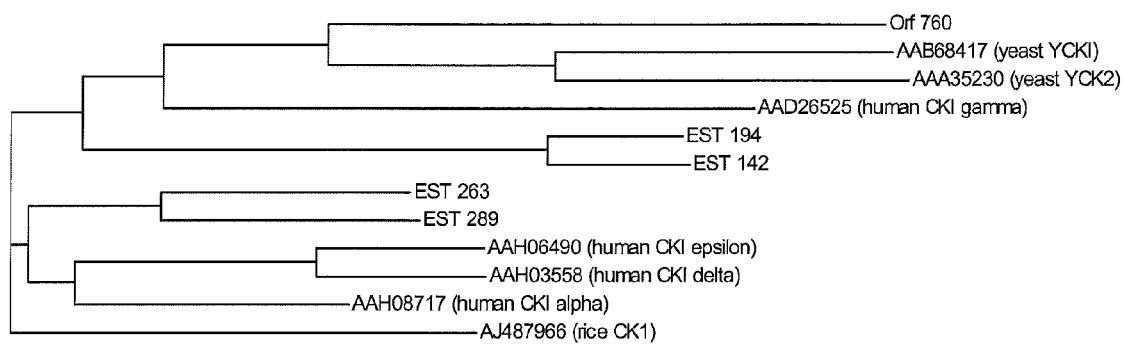
FIG. 4 shows a diagram illustrating the relative homology of the disclosed *Physcomitrella patens* and *Saccharomyces cerevisiae* casein kinases and other known casein kinases.
Figure 6:
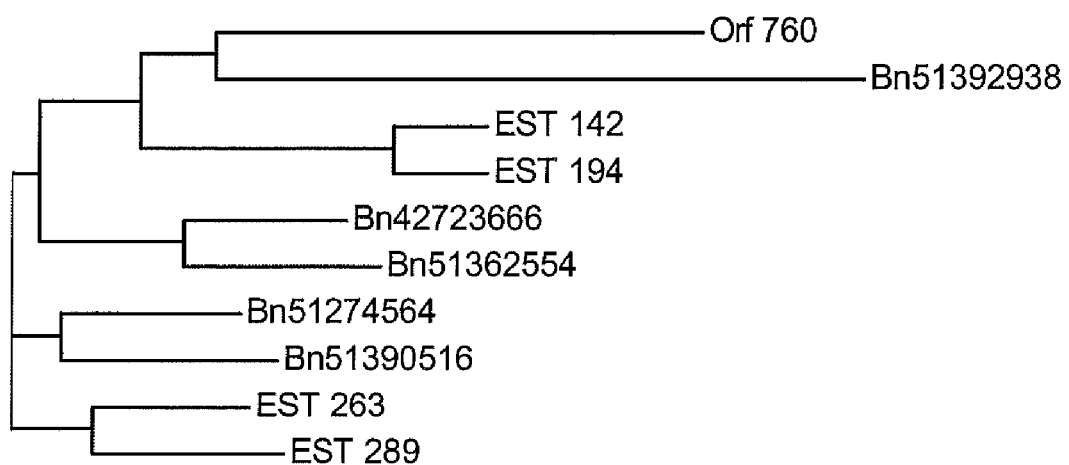
FIG. 6 shows a diagram illustrating the relative homology of the five disclosed *Physcomitrella patens* and *Saccharomyces cerevisiae* casein kinases with the disclosed *Brassica napus* casein kinases.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as polypeptide "Casein Kinase Stress-Related Polypeptides" (CKSRPs), in no way limits the functionality of those sequences.

The present invention describes a novel genus of CKSRPs and CKSRP coding nucleic acids that are important for modulating a plant's response to an environmental stress. More particularly, over-expression of these CKSRP coding nucleic acids in a plant results in the plant's increased tolerance to an environmental stress. Representative members of the CKSRP genus include, but are not limited to, PpCK-1, PpCK-2, PpCK-4, PpPK-4, ScCK-1, BnCK-1, BnCK-2, BnCK-3, BnCK-4, and BnCK-5. In a preferred embodiment, all members of the genus are biologically active casein kinases.

Accordingly, the present invention encompasses CKSRP polynucleotide and polypeptide sequences and their use for increasing a plant's tolerance to an environmental stress. In one embodiment, the CKSRP sequences are from a plant, preferably a *Physcomitrella* plant or a *Brassica* plant, and more preferably a *Physcomitrella patens* plant or a *Brassica napus* plant. In another embodiment, the CKSRP sequences include PpCK-1 (SEQ ID NOS:3 and 4), PpCK-2 (SEQ ID NOS:5 and 6), PpCK-4 (SEQ ID NOS:1 and 2), PpPK-4 (SEQ ID NOS:7 and 8), ScCK-1 (SEQ ID NOS:9 and 10), BnCK-1 (SEQ ID NOS:11 and 12), BnCK-2 (SEQ ID NOS: 13 and 14), BnCK-3 (SEQ ID NOS:15 and 16), BnCK-4 (SEQ ID NOS:17 and 18), and BnCK-5 (SEQ ID NOS:19 and 20). The disclosed *Physcomitrella patens* CKSRP sequences and the disclosed *Saccharomyces cerevisiae* CKSRP sequence have significant percent identity to known casein kinases as is indicated in Table 1.

TABLE 1

|  | ORF 760 Sim (%) | ORF 760 Iden (%) | EST 142 Sim (%) | EST 142 Iden (%) | EST 194 Sim (%) | EST 194 Iden (%) | EST 263 Sim (%) | EST 263 Iden (%) | EST 289 Sim (%) | EST 289 Iden (%) |
|---|---|---|---|---|---|---|---|---|---|---|
| ORF 760 |  |  | 32.9 | 25.4 | 33.4 | 24.7 | 43.3 | 34.5 | 42.0 | 32.4 |
| AAB68417 | 50.9 | 41.2 | 36.3 | 26.0 | 36.8 | 26.5 | 42.7 | 32.8 | 41.9 | 31.4 |
| AAA35230 | 48.8 | 39.4 | 36.2 | 25.8 | 36.9 | 26.1 | 42.3 | 31.3 | 43.2 | 31.1 |
| EST 263 | 43.3 | 34.5 | 40.4 | 32.5 | 40.5 | 33.2 |  |  | 80.8 | 74.0 |
| EST 194 | 33.4 | 24.7 | 90.2 | 86.9 |  |  | 40.5 | 33.2 | 42.0 | 32.4 |
| EST 289 | 42.0 | 32.4 | 41.3 | 33.3 | 41.7 | 33.7 | 80.8 | 74.0 |  |  |
| AAH06490 | 43.7 | 33.4 | 44.2 | 34.6 | 43.0 | 33.8 | 63.7 | 53.8 | 63.9 | 53.4 |
| AAH03558 | 42.4 | 33.0 | 43.7 | 34.5 | 44.1 | 34.9 | 63.2 | 54.5 | 65.0 | 54.2 |
| AAH08717 | 39.7 | 31.5 | 50.7 | 40.0 | 51.7 | 40.7 | 53.3 | 45.8 | 54.1 | 46.7 |
| AAD26525 | 41.6 | 32.8 | 43.6 | 32.3 | 42.5 | 31.9 | 48.9 | 38.4 | 49.0 | 38.0 |
| EST 142 | 32.9 | 25.4 |  |  | 90.2 | 86.9 | 40.4 | 32.5 | 41.3 | 33.3 |

TABLE 1-continued

| | ORF 760 Sim (%) | ORF 760 Iden (%) | EST 142 Sim (%) | EST 142 Iden (%) | EST 194 Sim (%) | EST 194 Iden (%) | EST 263 Sim (%) | EST 263 Iden (%) | EST 289 Sim (%) | EST 289 Iden (%) |
|---|---|---|---|---|---|---|---|---|---|---|
| AJ487966 | 44.8 | 33.6 | 40.1 | 30.7 | 40.5 | 30.9 | 72.0 | 58.6 | 68.7 | 55.9 |

The present invention provides a transgenic plant cell transformed by a CKSRP coding nucleic acid, wherein expression of the nucleic acid sequence in the plant cell results in increased tolerance to an environmental stress as compared to a wild type variety of the plant cell. The invention further provides transgenic plant parts and transgenic plants containing the plant cells described herein. Plant parts include, but are not limited to, stems, roots, ovules, stamens, leaves, embryos, meristematic regions, callus tissue, gametophytes, sporophytes, pollen, microspores, and the like. In one embodiment, the transgenic plant is male sterile. Also provided is a plant seed produced by a transgenic plant transformed by a CKSRP coding nucleic acid, wherein the seed contains the CKSRP coding nucleic acid, and wherein the plant is true breeding for increased tolerance to environmental stress as compared to a wild type variety of the plant. The invention further provides a seed produced by a transgenic plant expressing a CKSRP, wherein the seed contains the CKSRP, and wherein the plant is true breeding for increased tolerance to environmental stress as compared to a wild type variety of the plant. The invention also provides an agricultural product produced by any of the below-described transgenic plants, plant parts, and plant seeds. Agricultural products include, but are not limited to, plant extracts, proteins, amino acids, carbohydrates, fats, oils, polymers, vitamins, and the like.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* CKSRPs, PpCK-1, PpCK-2, PpCk-3, and PpPK-4; *Saccharomyces cerevisiae* CKSRP ScCK-1; and *Brassica napus* CKSRPs, BnCK-1, BnCK-2, BnCK-3, BnCK-4, and BnCK-5 are useful for increasing a plant's tolerance to environmental stress. As used herein, the term polypeptide refers to a chain of at least four amino acids joined by peptide bonds. The chain may be linear, branched, circular, or combinations thereof. Accordingly, the present invention provides isolated CKSRPs selected from PpCK-1, PpCK-2, PpCK-4, PpPK-4, ScCK-1, BnCK-1, BnCK-2, BnCK-3, BnCK-4, and BnCK-5, and homologs thereof. In preferred embodiments, the CKSRP is selected from: 1) *Physcomitrella patens* Casein Kinase-1 (PpCK-1) polypeptide as defined in SEQ ID NO:4) *Physcomitrella patens* Casein Kinase-2 (PpCK-2) polypeptide as defined in SEQ ID NO:6) *Physcomitrella patens* Casein Kinase-4 (PpCK-4) polypeptide as defined in SEQ ID NO:1) *Physcomitrella patens* Protein Kinase-4 (PpPK-4) polypeptide as defined in SEQ ID NO:8) *Saccharomyces cerevisiae* Casein Kinase-1 (ScCK-1) polypeptide as defined in SEQ ID NO:10) *Brassica napus* Casein Kinase-1 (BnCK-1) polypeptide as defined in SEQ ID NO:12; *Brassica napus* Casein Kinase-2 (BnCK-2) polypeptide as defined in SEQ ID NO:14; *Brassica napus* Casein Kinase-3 (BnCK-4) polypeptide as defined in SEQ ID NO:16; *Brassica napus* Casein Kinase-4 (BnCK-4) polypeptide as defined in SEQ ID NO:18; *Brassica napus* Casein Kinase-5 (BnCK-5) polypeptide as defined in SEQ ID NO:20; and homologs and orthologs thereof. Homologs and orthologs of the amino acid sequences are defined below.

The CKSRPs of the present invention are preferably produced by recombinant DNA techniques. For example, a nucleic acid molecule encoding the polypeptide is cloned into an expression vector (as described below), the expression vector is introduced into a host cell (as described below), and the CKSRP is expressed in the host cell. The CKSRP can then be isolated from the cells by an appropriate purification scheme using standard polypeptide purification techniques. For the purposes of the invention, the term "recombinant polynucleotide" refers to a polynucleotide that has been altered, rearranged, or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, a CKSRP, or peptide thereof, can be synthesized chemically using standard peptide synthesis techniques. Moreover, native CKSRP can be isolated from cells (e.g., *Physcomitrella patens, Saccharomyces cerevisiae*, or *Brassica napus* cells), for example using an anti-CKSRP antibody, which can be produced by standard techniques utilizing a CKSRP or fragment thereof.

As used herein, the term "environmental stress" refers to sub-optimal conditions associated with salinity, drought, temperature, metal, chemical, pathogenic, and oxidative stresses, or combinations thereof. In preferred embodiments, the environmental stress can be selected from one or more of the group consisting of salinity, drought, or temperature, or combinations thereof, and in particular, can be selected from one or more of the group consisting of high salinity, low water content, or low temperature. It is also to be understood that as used in the specification and in the claims, "a" or "an" can mean one or more, depending upon the context in which it is used. Thus, for example, reference to "a cell" can mean that at least one cell can be utilized. As also used herein, the term "water use efficiency" refers to the amount of organic matter produced by a plant divided by the amount of water used by the plant in producing it, i.e. the dry weight of a plant in relation to the plant's water use.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences, which naturally flank the nucleic acid (i.e. sequences located at the 5' and 3' ends of the nucleic acid) in its naturally occurring replicon. For example, a cloned nucleic acid is considered isolated. In various embodiments, the isolated CKSRP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Physcomitrella patens* cell, a *Saccharomyces cerevisiae* cell, or a *Brassica napus* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or a portion thereof, can be isolated using standard molecular biology techniques and the sequence information provided herein. For example, a *P. patens* CKSRP cDNA can be isolated from a *P. patens* library using all or a portion of one of the sequences disclosed herein. Moreover, a nucleic acid molecule encompassing all or a portion of one of the sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, and SEQ ID NO:19, can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18:5294-5299), and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, and SEQ ID NO:19. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a CKSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. These cDNAs may comprise sequences encoding the CKSRPs, (i.e., the "coding region"), as well as 5' untranslated sequences and 3' untranslated sequences. Alternatively, the nucleic acid molecules of the present invention can comprise only the coding region of any of the sequences in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or can contain whole genomic fragments isolated from genomic DNA. The present invention also includes CKSRP coding nucleic acids that encode CKSRPs as described herein. Preferred is a CKSRP coding nucleic acid that encodes a CKSRP selected from the group consisting of PpCK-1 (SEQ ID NO:4), PpCK-2 (SEQ ID NO:6), PpCK-4 (SEQ ID NO:2), PpPK-4 (SEQ ID NO:8), ScCK-1 (SEQ ID NO:10), BnCK-1 (SEQ ID NO:12), BnCK-2 (SEQ ID NO:14), BnCK-3 (SEQ ID NO:16), BnCK-4 (SEQ ID NO:18), and BnCK-5 (SEQ ID NO:20).

Moreover, the nucleic acid molecule of the invention can comprise a portion of the coding region of one of the sequences in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, and SEQ ID NO:19, for example, a fragment that can be used as a probe or primer or a fragment encoding a biologically active portion of a CKSRP. The nucleotide sequences determined from the cloning of the CKSRP genes from *Physcomitrella patens, Saccharomyces cerevisiae*, and *Brassica napus* allow for the generation of probes and primers designed for use in identifying and/or cloning CKSRP homologs in other cell types and organisms, as well as CKSRP homologs from other mosses and related species. The portion of the coding region can also encode a biologically active fragment of a CKSRP.

As used herein, the term "biologically active portion of" a CKSRP is intended to include a portion, e.g., a domain/motif, of a CKSRP that participates in modulation of stress tolerance in a plant, and more preferably, drought tolerance or salt tolerance. For the purposes of the present invention, modulation of stress tolerance refers to at least a 10% increase or decrease in the stress tolerance of a transgenic plant comprising a CKSRP expression cassette (or expression vector) as compared to the stress tolerance of a non-transgenic control plant. Methods for quantitating stress tolerance are provided at least in Example 7 below. In a preferred embodiment, the biologically active portion of a CKSRP increases a plant's tolerance to an environmental stress.

Figure 5:
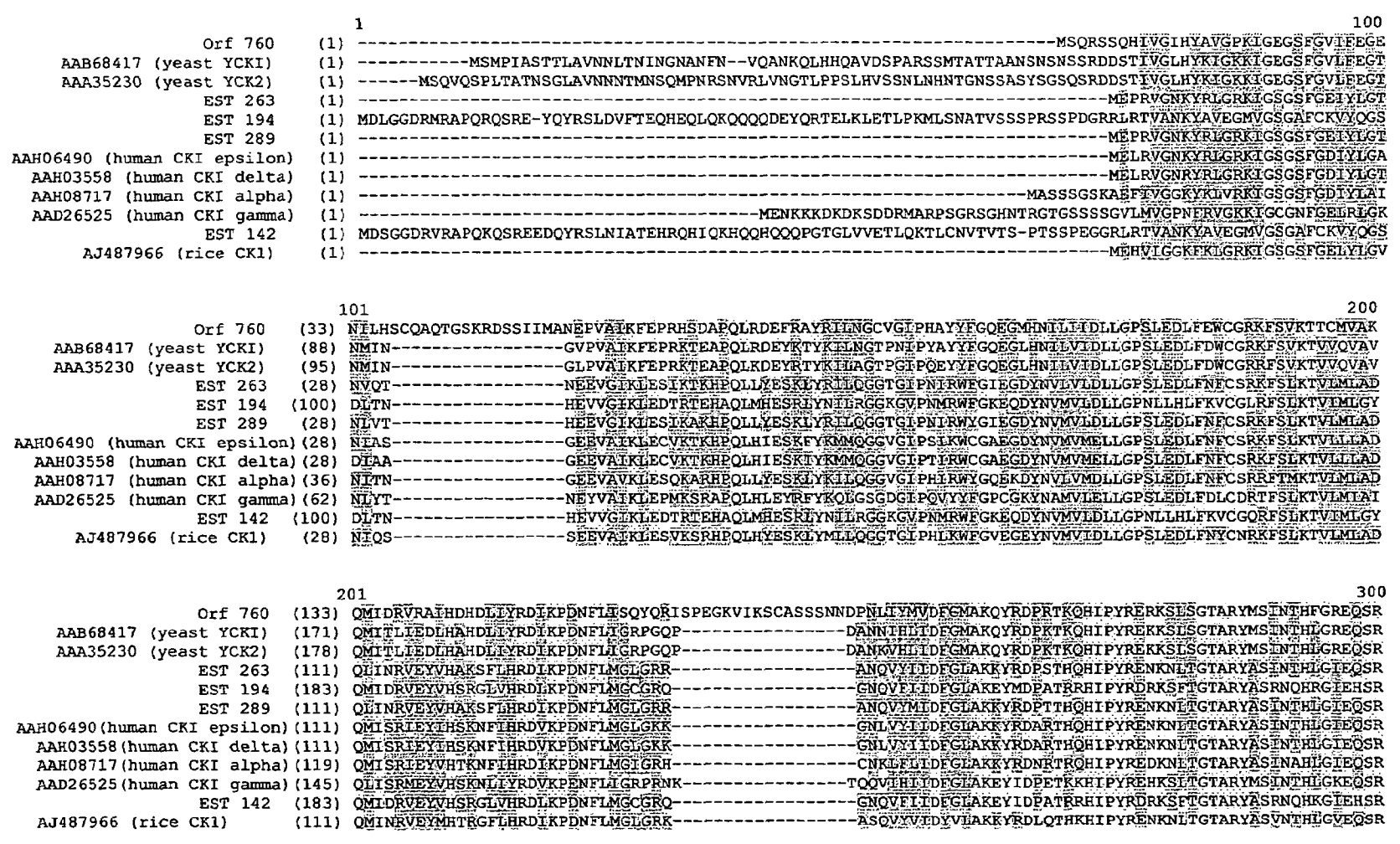
Figure 7:
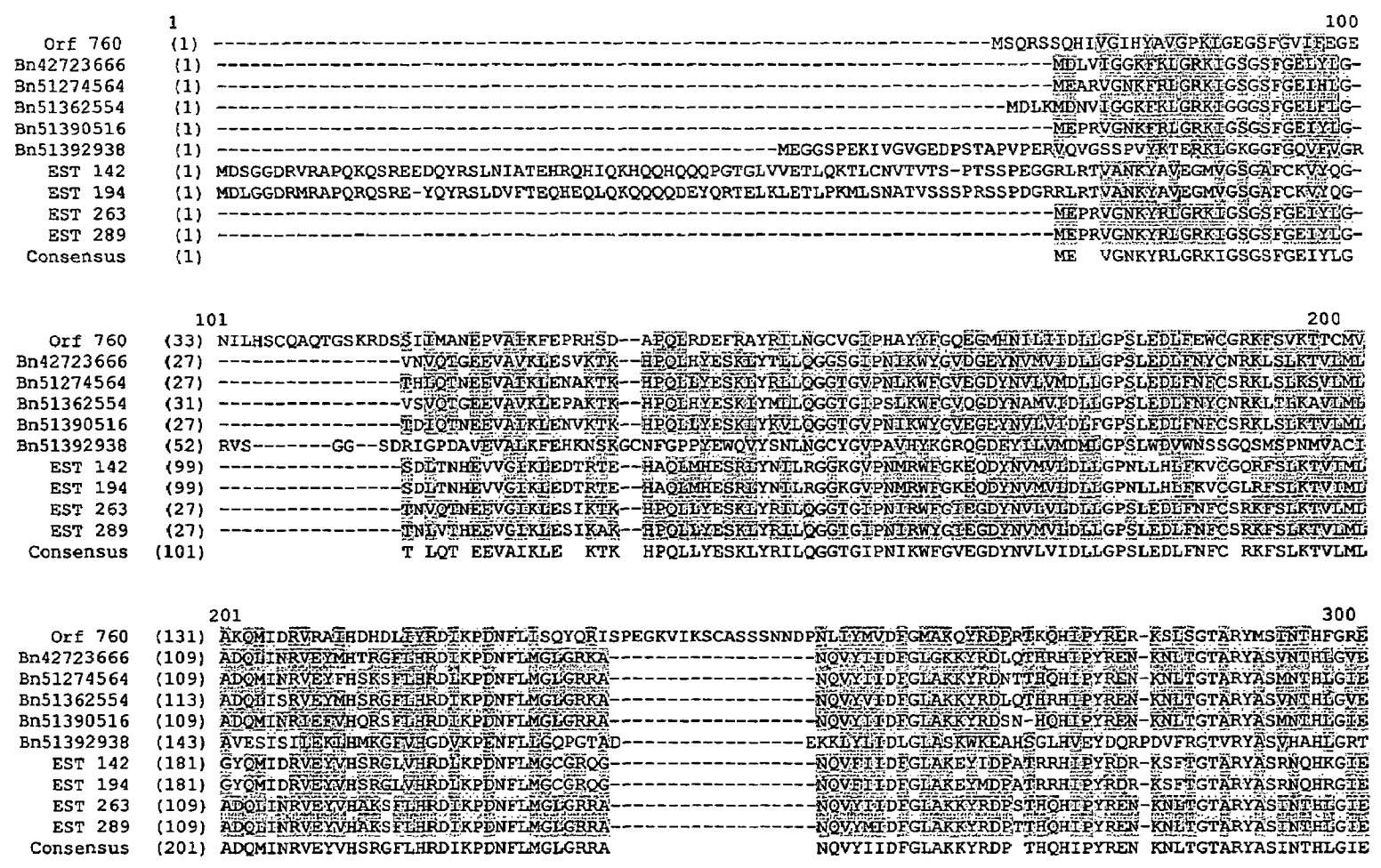
Figure 7:
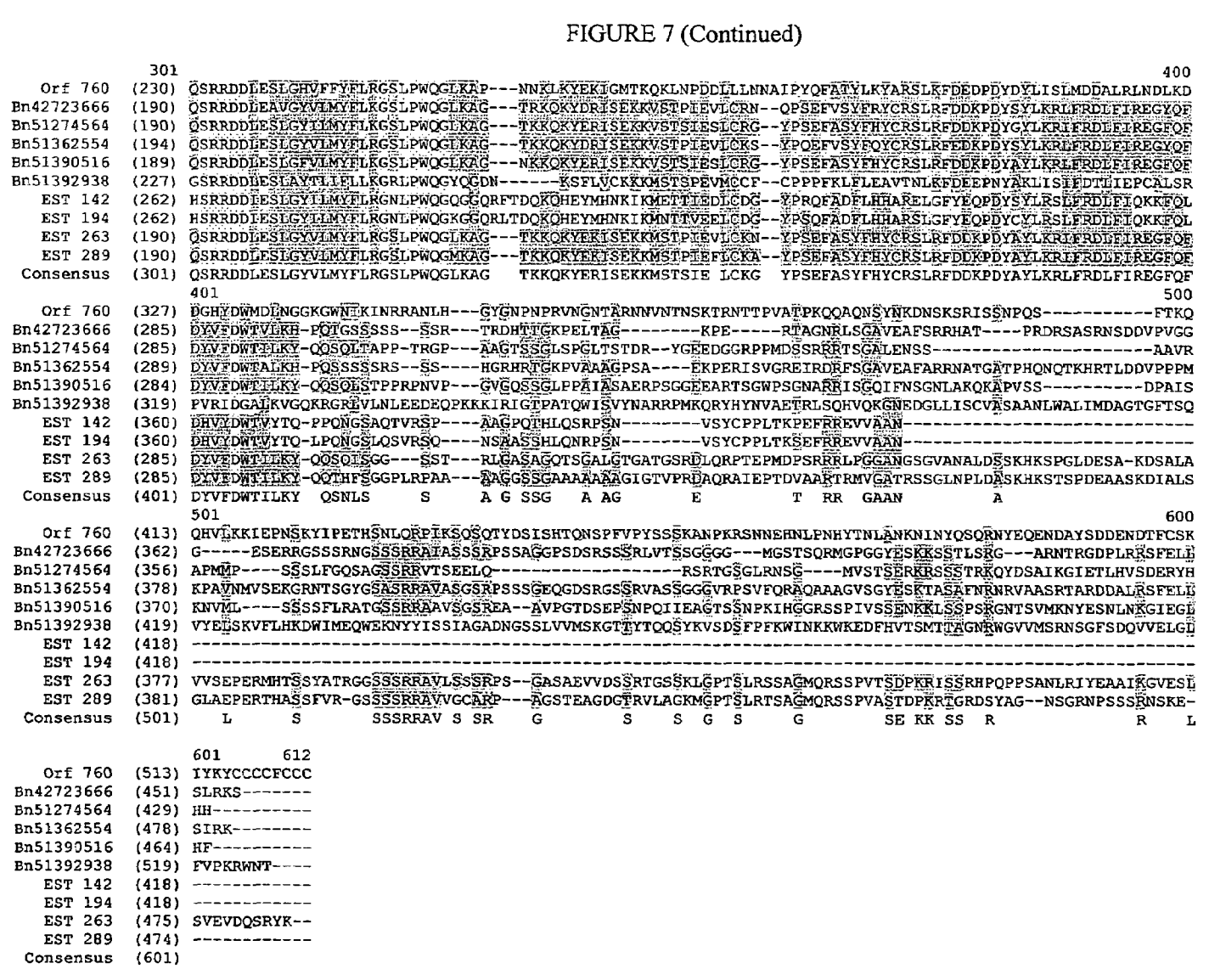

Biologically active portions of a CKSRP include peptides comprising amino acid sequences derived from the amino acid sequence of a CKSRP, e.g., an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, or the amino acid sequence of a polypeptide identical to a CKSRP, which include fewer amino acids than a full length CKSRP or the full length polypeptide which is identical to a CKSRP, and exhibit at least one activity of a CKSRP. Typically, biologically active portions (e.g., peptides which are, for example, 5, 10, 15, 20, 30, 35, 36, 37, 38, 39, 40, 50, 100, or more amino acids in length) comprise a domain or motif with at least one activity of a CKSRP. Moreover, other biologically active portions, in which other regions of the polypeptide are deleted, can be prepared by recombinant techniques and evaluated for one or more of the activities described herein. Preferably, the biologically active portion of a CKSRP includes one or more selected domains/motifs, or portions thereof, having biological activity such as the conserved central kinase domain, as is shown in FIGS. 5 and 7. In a preferred embodiment, the conserved central kinase domain comprises four conserved regions, wherein the first region commences with a glycine residue at position 1 and has a glycine at position 3 and a phenylalanine residue at position 5; the second region is downstream from the first region, commences with a valine residue at position 1, and has a lysine at position 4, a glutamate residue at position 6, a glutamine residue at position 14, a leucine residue at position 15, a glutamate residue at position 18, a tyrosine residue at position 22, a proline residue at position 32, a glycine residue at position 38, a asparagine residue at position 44, a leucine residue at positions 50 and 51, a glycine residue at position 52, a proline residue at position 53, a leucine residue at position 55, a leucine residue at position 58, a phenylalanine residue at position 59, a cysteine residue at position 62, a phenylalanine residue at position 66, a lysine residue at position 69, a threonine residue at position 70, a glutamine residue at position 77, a isoleucine residue at position 79, a histidine residue at position 86, an arginine residue at position 93, an aspartic acid residue at position 94, a lysine residue at position 96, a proline residue at position 97, a asparagine residue at position 99, a phenylalanine residue at position 100, and a leucine residue at position 101; the third region is downstream from the second region, commences with an aspartic acid residue at position 1, and has an alanine residue at position 5, a lysine residue at position 6, a tyrosine residue at position 8, an aspartic acid residue at position 10, a threonine residue at position 13, a histidine residue at position 16, a isoleucine residue at position 17, a proline residue at position 18, a tyrosine residue at position 19, a arginine residue at position 20, a lysine residue at position 23, a glycine residue at position 27, a threonine residue at position 28, a alanine residue at position 29, a arginine residue at position 30, a tyrosine residue at position 31, a serine residue at position 33, an asparagines residue at position 35, a histidine residue at position 37, a glycine residue at position 39, a glutamate residue at position 41, a serine residue at position 43, an arginine residue at position 44, an arginine residue at position 45, an aspartic acid residue at position 46, an aspartic acid residue at position 47, a glutamate residue at position 49, a glycine residue at position 52, a tyrosine residue at position 57, a phenylalanine residue at position 58, a leucine residue at position 63, a proline residue at position 64, a tryptophan residue at position 65, a glutamine residue at position 66, and a glycine residue at position 67, and the fourth region is downstream from the third region, commences with a proline residue at position 1, and has an arginine residue at position 12, a leucine residue at position 14, a phenylalanine residue at position 16, a proline residue at position 20, an aspartic acid residue at position 21, a tyrosine residue at position 22, an aspartic acid residue at position 41, an aspartic acid residue at position 45, and a tryptophan residue at position 46.

The invention also provides CKSRP chimeric or fusion polypeptides. As used herein, a CKSRP "chimeric polypeptide" or "fusion polypeptide" comprises a CKSRP operatively linked to a non-CKSRP. A CKSRP refers to a polypeptide having an amino acid sequence corresponding to a CKSRP, whereas a non-CKSRP refers to a polypeptide having an amino acid sequence corresponding to a polypeptide which is not substantially identical to the CKSRP, e.g., a polypeptide that is different from the CKSRP and is derived from the same or a different organism. Within the fusion polypeptide, the term "operatively linked" is intended to indicate that the CKSRP and the non-CKSRP are fused to each other so that both sequences fulfill the proposed function attributed to the sequence used. The non-CKSRP can be fused to the N-terminus or C-terminus of the CKSRP. For example, in one embodiment, the fusion polypeptide is a GST-CKSRP fusion polypeptide in which the CKSRP sequences are fused to the C-terminus of the GST sequences. Such fusion polypeptides can facilitate the purification of recombinant CKSRPs. In another embodiment, the fusion polypeptide is a CKSRP containing a heterologous signal sequence at its N-terminus. In certain host cells (e.g., mammalian host cells), expression and/or secretion of a CKSRP can be increased through use of a heterologous signal sequence.

Preferably, a CKSRP chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al. John Wiley & Sons: 1992). Moreover, many expression vectors are commercially available that already encode a fusion moiety (e.g., a GST polypeptide). A CKSRP encoding nucleic acid can be cloned into such an expression vector such that the fusion moiety is linked in-frame to the CKSRP.

In addition to fragments and fusion polypeptides of the CKSRPs described herein, the present invention includes homologs and analogs of naturally occurring CKSRPs and CKSRP encoding nucleic acids in a plant. "Homologs" are defined herein as two nucleic acids or polypeptides that have similar, or "identical," nucleotide or amino acid sequences, respectively. Homologs include allelic variants, orthologs, paralogs, agonists, and antagonists of CKSRPs as defined hereafter. The term "homolog" further encompasses nucleic acid molecules that differ from one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, and SEQ ID NO:19 (and portions thereof) due to degeneracy of the genetic code and thus encode the same CKSRP as that encoded by the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. As used herein, a "naturally occurring" CKSRP refers to a CKSRP amino acid sequence that occurs in nature. Preferably, a naturally occurring CKSRP comprises an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20.

An agonist of the CKSRP can retain substantially the same, or a subset, of the biological activities of the CKSRP. An antagonist of the CKSRP can inhibit one or more of the activities of the naturally occurring form of the CKSRP. For example, the CKSRP antagonist can competitively bind to a downstream or upstream member of the cell membrane component metabolic cascade that includes the CKSRP, or bind to a CKSRP that mediates transport of compounds across such membranes, thereby preventing translocation from taking place.

Nucleic acid molecules corresponding to natural allelic variants and analogs, orthologs, and paralogs of a CKSRP cDNA can be isolated based on their identity to the *Physcomitrella patens, Saccharomyces cerevisiae*, or *Brassica napus* CKSRP nucleic acids described herein using CKSRP cDNAs, or a portion thereof, as a hybridization probe according to standard hybridization techniques under stringent hybridization conditions. In an alternative embodiment, homologs of the CKSRP can be identified by screening combinatorial libraries of mutants, e.g., truncation mutants, of the CKSRP for CKSRP agonist or antagonist activity. In one embodiment, a variegated library of CKSRP variants is generated by combinatorial mutagenesis at the nucleic acid level and is encoded by a variegated gene library. A variegated library of CKSRP variants can be produced by, for example, enzymatically ligating a mixture of synthetic oligonucleotides into gene sequences such that a degenerate set of potential CKSRP sequences is expressible as individual polypeptides, or alternatively, as a set of larger fusion polypeptides (e.g., for phage display) containing the set of CKSRP sequences therein. There are a variety of methods that can be used to produce libraries of potential CKSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential CKSRP sequences. Methods for synthesizing degenerate oligonucleotides are known in the art (See, e.g., Narang, S. A., 1983, Tetrahedron 39:3; Itakura et al., 1984, Annu. Rev. Biochem. 53:323; Itakura et al., 1984, Science 198:1056; Ike et al., 1983, Nucleic Acid Res. 11:477).

In addition, libraries of fragments of the CKSRP coding regions can be used to generate a variegated population of CKSRP fragments for screening and subsequent selection of homologs of a CKSRP. In one embodiment, a library of coding sequence fragments can be generated by treating a double stranded PCR fragment of a CKSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the CKSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CKSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify CKSRP homologs (Arkin and Yourvan, 1992, PNAS 89:7811-7815; Delgrave et al., 1993, Polypeptide Engineering 6(3):327-331). In another embodiment, cell based assays can be exploited to analyze a variegated CKSRP library, using methods well known in the art. The present invention further provides a method of identifying a novel CKSRP, comprising (a) raising a specific antibody response to a CKSRP, or a fragment thereof, as described herein; (b) screening putative CKSRP material with the antibody, wherein specific binding of the antibody to the material indicates the presence of a potentially novel CKSRP; and (c) analyzing the bound material in comparison to known CKSRP, to determine its novelty.

As stated above, the present invention includes CKSRPs and homologs thereof. To determine the percent sequence identity of two amino acid sequences (e.g., one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20) is occupied by the same amino acid residue as the corresponding position in the other sequence (e.g., a mutant form of the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to the amino acid sequence shown as residues 2-304 of SEQ ID NO:2, residues 77-368 of SEQ ID NO:4, residues 2-294 of SEQ ID NO:6, residues 77-368 of SEQ ID NO:8, residues 77-336 of SEQ ID NO:10, residues 1-296 of SEQ ID NO:12, residues 1-296 of SEQ ID NO:14, residues 5-300 of SEQ ID NO:16, residues 1-295 of SEQ ID NO:18, or residues 25-327 of SEQ ID NO:20. In another embodiment, the isolated amino acid homolog of the present invention is encoded by a nucleic acid as defined by nucleotides at positions 4 to 912 of SEQ ID NO:1, nucleotides at positions 229 to 1104 of SEQ ID NO:3, nucleotides at positions 4 to 882 of SEQ ID NO:5, nucleotides at positions 229 to 1104 of SEQ ID NO:7, nucleotides at positions 229 to 1008 of SEQ ID NO:9, nucleotides at positions 1 to 888 of SEQ ID NO:11, nucleotides at positions 1 to 888 of SEQ ID NO:13, nucleotides at positions 13 to 900 of SEQ ID NO:15, nucleotides at positions 1 to 885 of SEQ ID NO:17, or nucleotides at positions 73 to 981 of SEQ ID NO:19.

In another embodiment, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. In yet another embodiment, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence encoded by a nucleic acid sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. In other embodiments, the CKSRP amino acid homologs have sequence identity over at least 15 contiguous amino acid residues, more preferably at least 25 contiguous amino acid residues, and most preferably at least 35 contiguous amino acid residues of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20.

In another preferred embodiment, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, or to a portion comprising at least 60 consecutive nucleotides thereof. The preferable length of sequence comparison for nucleic acids is at least 75 nucleotides, more preferably at least 100 nucleotides, and most preferably the entire length of the coding region. It is even more preferable that the nucleic acid homologs encode proteins having homology with SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 over the central kinase domain shown in FIGS. 5 and 7.

It is further preferred that the isolated nucleic acid homolog of the invention encodes a CKSRP, or portion thereof, that is at least 70% identical to an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 and that functions as a modulator of an environmental stress response in a plant. In a more preferred embodiment, overexpression of the nucleic acid homolog in a plant increases the tolerance of the plant to an environmental stress. In a further preferred embodiment, the nucleic acid homolog encodes a CKSRP that functions as a casein kinase.

For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap-opening penalty of 15 and a gap extension penalty of 6.66 are used for determining the percent identity of two nucleic acids. A gap-opening penalty of 10 and a gap extension penalty of 0.1 are used for determining the percent identity of two polypeptides. All other parameters are set at the default settings. For purposes of a multiple alignment (Clustal W algorithm), the gap-opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 under stringent conditions. More particularly, an isolated nucleic acid molecule of the invention is at least 15 nucleotides in length and hybridizes under stringent conditions to the nucleic acid molecule comprising a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. In other embodiments, the nucleic acid is at least 30, 50, 100, 250, or more nucleotides in length. Preferably, an isolated nucleic acid homolog of the invention comprises a nucleotide sequence which hybridizes under highly stringent conditions to the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 and functions as a modulator of stress tolerance in a plant. In a further preferred embodiment, overexpression of the isolated nucleic acid homolog in a plant increases a plant's tolerance to an environmental stress. In an even further preferred embodiment, the isolated nucleic acid homolog encodes a CKSRP that functions as a casein kinase.

As used herein with regard to hybridization for DNA to a DNA blot, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in a preferred embodiment, the phrase "highly stringent conditions" refers to hybridization in a 6×SSC solution at 65° C. In another embodiment, "highly stringent conditions" refers to hybridization overnight at 65° C. in 10× Denharts solution, 6×SSC, 0.5% SDS, and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138:267-284; Current Protocols in Molecular Biology, Chapter 2, Ausubel et al. Eds., Greene Publishing and Wiley-Interscience, New York, 1995; and Tijssen, 1993, Laboratory Techniques in Biochemistry and Molecular Biology: Hybridization with Nucleic Acid Probes, Part I, Chapter 2, Elsevier, N.Y., 1993. Preferably, an isolated nucleic acid molecule of the invention that hybridizes under stringent or highly stringent conditions to a sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring Physcomitrella patens CKSRP, a Saccharomyces cerevisiae CKSRP or a Brassica napus CKSRP.

Using the above-described methods, and others known to those of skill in the art, one of ordinary skill in the art can isolate homologs of the CKSRPs comprising amino acid sequences shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. One subset of these homologs is allelic variants. As used herein, the term "allelic variant" refers to a nucleotide sequence containing polymorphisms that lead to changes in the amino acid sequences of a CKSRP and that exist within a natural population (e.g., a plant species or variety). Such natural allelic variations can typically result in 1-5% variance in a CKSRP nucleic acid. Allelic variants can be identified by sequencing the nucleic acid sequence of interest in a number of different plants, which can be readily carried out by using hybridization probes to identify the same CKSRP genetic locus in those plants. Any and all such nucleic acid variations and resulting amino acid polymorphisms or variations in a CKSRP that are the result of natural allelic variation and that do not alter the functional activity of a CKSRP, are intended to be within the scope of the invention.

Moreover, nucleic acid molecules encoding CKSRPs from the same or other species such as CKSRP analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al., 1997, Science 278(5338):631-637). Analogs, orthologs, and paralogs of a naturally occurring CKSRP can differ from the naturally occurring CKSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably, 85-90% or 90-95%, and most preferably 95%, 96%, 97%, 98%, or even 99% identity, or 100% sequence identity, with all or part of a naturally occurring CKSRP amino acid sequence, and will exhibit a function similar to a CKSRP. Preferably, a CKSRP ortholog of the present invention functions as a modulator of an environmental stress response in a plant and/or functions as a casein kinase. More preferably, a CKSRP ortholog increases the stress tolerance of a plant. In one embodiment, the CKSRP orthologs maintain the ability to participate in the metabolism of compounds necessary for the construction of cellular membranes in a plant, or in the transport of molecules across these membranes.

In addition to naturally-occurring variants of a CKSRP sequence that may exist in the population, the skilled artisan will further appreciate that changes can be introduced by mutation into a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, thereby leading to changes in the amino acid sequence of the encoded CKSRP, without altering the functional activity of the CKSRP. For example, nucleotide substitutions leading to amino acid substitutions at "non-essential" amino acid residues can be made in a sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. A "non-essential" amino acid residue is a residue that can be altered from the wild-type sequence of one of the CKSRPs without altering the activity of said CKSRP, whereas an "essential" amino acid residue is required for CKSRP activity. Other amino acid residues, however, (e.g., those that are not conserved or only semi-conserved in the domain having CKSRP activity) may not be essential for activity and thus are likely to be amenable to alteration without altering CKSRP activity.

Accordingly, another aspect of the invention pertains to nucleic acid molecules encoding CKSRPs that contain changes in amino acid residues that are not essential for CKSRP activity. Such CKSRPs differ in amino acid sequence from a sequence contained in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, yet retain at least one of the CKSRP activities described herein. In one embodiment, the isolated nucleic acid molecule comprises a nucleotide sequence encoding a polypeptide, wherein the polypeptide comprises an amino acid sequence at least about 50% identical to the central protein kinase region of an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. Preferably, the polypeptide encoded by the nucleic acid molecule is at least about 50-60% identical to the central protein kinase region of one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, more preferably at least about 60-70% identical to the central protein kinase region of one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, even more preferably at least about 70-75%, 75-80%, 80-85%, 85-90%, or 90-95% identical to the central protein kinase region of one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, and most preferably at least about 96%, 97%, 98%, or 99% identical to the central protein kinase region of one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. In another embodiment, the polypeptide encoded by the nucleic acid molecule is at least about 50-60% identical to one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, more preferably at least about 60-70% identical to one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, even more preferably at least about 70-75%, 75-80%, 80-85%, 85-90%, or 90-95% identical to one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, and most preferably at least about 96%, 97%, 98%, or 99% identical to one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. The preferred CKSRP homologs of the present invention preferably participate in a stress tolerance response in a plant, or more particularly, participate in the transcription of a polypeptide involved in a stress tolerance response in a plant, and/or function as a casein kinase.

An isolated nucleic acid molecule encoding a CKSRP having sequence identity with a polypeptide sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 can be created by introducing one or more nucleotide substitutions, additions or deletions into a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, respectively, such that one or more amino acid substitutions, additions, or deletions are introduced into the encoded polypeptide. Mutations can be introduced into one of the sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in a CKSRP is preferably replaced with another amino acid residue from the same side chain family. Alternatively, in another embodiment, mutations can be introduced randomly along all or part of a CKSRP coding sequence, such as by saturation mutagenesis, and the resultant mutants can be screened for a CKSRP activity described herein to identify mutants that retain CKSRP activity. Following mutagenesis of one of the sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, the encoded polypeptide can be expressed recombinantly and the activity of the polypeptide can be determined by analyzing the stress tolerance of a plant expressing the polypeptide as described in Example 7.

Additionally, optimized CKSRP nucleic acids can be created. Preferably, an optimized CKSRP nucleic acid encodes a CKSRP that binds to a phosphate group and/or modulates a plant's tolerance to an environmental stress, and more preferably increases a plant's tolerance to an environmental stress upon its overexpression in the plant. As used herein, "optimized" refers to a nucleic acid that is genetically engineered to increase its expression in a given plant or animal. To provide plant optimized CKSRP nucleic acids, the DNA sequence of the gene can be modified to 1) comprise codons preferred by highly expressed plant genes; 2) comprise an A+T content in nucleotide base composition to that substantially found in plants; 3) form a plant initiation sequence; or 4) to eliminate sequences that cause destabilization, inappropriate polyadenylation, degradation and termination of RNA, or that form secondary structure hairpins or RNA splice sites. Increased expression of CKSRP nucleic acids in plants can be achieved by utilizing the distribution frequency of codon usage in plants in general or in a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991, Proc. Natl. Acad. Sci. USA 88:3324-3328; and Murray et al., 1989, Nucleic Acids Res. 17:477-498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A = n = 1ZX_n - Y_nX_n$ times 100 Z where $X_n$=frequency of usage for codon n in the host cell; $Y_n$=frequency of usage for codon n in the synthetic gene; n represents an individual codon that specifies an amino acid; and the total number of codons is Z. The overall deviation of the frequency of codon usage, A, for all amino acids should preferably be less than about 25%, and more preferably less than about 10%.

Hence, a CKSRP nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized CKSRP nucleic acids of this invention also preferably have CG and TA doublet avoidance indices closely approximating those of the chosen host plant (e.g., *Physcomitrella patens, Brassica napus, Glycine max,* or *Oryza sativa*). More preferably these indices deviate from that of the host by no more than about 10-15%.

In addition to the nucleic acid molecules encoding the CKSRPs described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20.

The antisense nucleic acid can be complementary to an entire CKSRP coding strand, or to only a portion thereof. In one embodiment, an antisense nucleic acid molecule is antisense to a "coding region" of the coding strand of a nucleotide sequence encoding a CKSRP. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding a CKSRP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of CKSRP mRNA, but more preferably is an oligonucleotide that is antisense to only a portion of the coding or noncoding region of CKSRP mRNA. For example, the antisense oligonucleotide can be complementary to the region surrounding the translation start site of CKSRP mRNA. An antisense oligonucleotide can be, for example, about 5, 10, 15, 20, 25, 30, 35, 40, 45, or 50 nucleotides in length. Typically, the antisense molecules of the present invention comprise an RNA having 60-100% sequence identity with at least 14 consecutive nucleotides of SEQ ID NO:1, SEQ ID NO:3, SEQ ID NO:5, SEQ ID NO:7, SEQ ID NO:9, SEQ ID ////NO:11, SEQ ID NO:13, SEQ ID NO:15, SEQ ID NO:17, or SEQ ID NO:19, or a polynucleotide encoding a polypeptide of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. Preferably, the sequence identity will be at least 70%, more preferably at least 75%, 80%, 85%, 90%, 95%, or 98%, and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, Nucleic Acids. Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

The antisense nucleic acid molecules of the invention are typically administered to a cell or generated in situ such that they hybridize with or bind to cellular mRNA and/or genomic DNA encoding a CKSRP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of a CKSRP polypeptide. As used herein, the term "ribozyme" refers to a catalytic RNA-based enzyme with ribonuclease activity that is capable of cleaving a single-stranded nucleic acid, such as an mRNA, to which it has a complementary region. Ribozymes (e.g., hammerhead ribozymes described in Haselhoff and Gerlach, 1988, Nature 334:585-591) can be used to catalytically cleave CKSRP mRNA transcripts to thereby inhibit translation of CKSRP mRNA. A ribozyme having specificity for a CKSRP-encoding nucleic acid can be designed based upon the nucleotide sequence of a CKSRP cDNA, as disclosed herein (i.e., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a CKSRP-encoding mRNA. See, e.g., U.S. Pat. Nos. 4,987,071 and 5,116,742 to Cech et al. Alternatively, CKSRP mRNA can be used to select a catalytic RNA having a specific ribonuclease activity from a pool of RNA molecules. See, e.g., Bartel, D. and Szostak, J. W., 1993, Science 261:1411-1418. In preferred embodiments, the ribozyme will contain a portion having at least 7, 8, 9, 10, 12, 14, 16, 18, or 20 nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, or a polypeptide having at least 80% sequence identity with a polypeptide of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 over the central protein kinase domain. The hybridizing RNAs may be substantially or completely complementary. By "substantially complementary," is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides, ribonucleotide analogs such as 2'-O-methyl ribosyl residues, or combinations thereof. See, e.g., U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, e.g., U.S. Pat. No. 5,795,715. In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., 1987, Science 238:645-650 and Cooney et al., 1988, Science 241: 456-459) and co-suppression (Napoli et al., 1990, The Plant Cell 2:279-289) are known in the art. Partial and full-length cDNAs have been used for the co-suppression of endogenous plant genes. See, e.g., U.S. Pat. Nos. 4,801,340, 5,034,323, 5,231,020, and 5,283,184; Van der Kroll et al., 1990, The Plant Cell 2:291-299; Smith et al., 1990, Mol. Gen. Genetics 224:477-481; and Napoli et al., 1990, The Plant Cell 2:279-289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95%, or more. The introduced sense polynucleotide need not be full length relative to the target gene or transcript. Preferably, the sense polynucleotide will have at least 65% sequence identity with at least 100 consecutive nucleotides of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. The regions of identity can comprise introns and/or exons and untranslated regions. The introduced sense polynucleotide may be present in the plant cell transiently, or may be stably integrated into a plant chromosome or extrachromosomal replicon.

Alternatively, CKSRP gene expression can be inhibited by targeting nucleotide sequences complementary to the regulatory region of a CKSRP nucleotide sequence (e.g., a CKSRP promoter and/or enhancer) to form triple helical structures that prevent transcription of a CKSRP gene in target cells. See generally, Helene, C., 1991, Anticancer Drug Des. 6(6):569-84; Helene, C. et al., 1992, Ann. N.Y. Acad. Sci. 660:27-36; and Maher, L. J., 1992, Bioassays 14(12):807-15.

In addition to the CKSRP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of one of the sequences set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19;

an anti-sense sequence of one of the sequences set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19; or naturally occurring mutants thereof. Primers based on a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 can be used in PCR reactions to clone CKSRP homologs. Probes based on the CKSRP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a CKSRP, such as by measuring a level of a CKSRP-encoding nucleic acid, in a sample of cells, e.g., detecting CKSRP mRNA levels or determining whether a genomic CKSRP gene has been mutated or deleted.

In particular, a useful method to ascertain the level of transcription of the gene (an indicator of the amount of mRNA available for translation to the gene product) is to perform a Northern blot (For reference, see, for example, Ausubel et al., 1988, Current Protocols in Molecular Biology, Wiley: New York). The information from a Northern blot at least partially demonstrates the degree of transcription of the transformed gene. Total cellular RNA can be prepared from cells, tissues, or organs by several methods, all well-known in the art, such as that described in Bormann, E. R. et al., 1992, Mol. Microbiol. 6:317-326. To assess the presence or relative quantity of polypeptide translated from this mRNA, standard techniques, such as a Western blot, may be employed. These techniques are well known to one of ordinary skill in the art. (See, for example, Ausubel et al., 1988, Current Protocols in Molecular Biology, Wiley: New York).

The invention further provides an isolated recombinant expression vector comprising a CKSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., CKSRPs, mutant forms of CKSRPs, fusion polypeptides, etc.).

The recombinant expression vectors of the invention can be designed for expression of CKSRPs in prokaryotic or eukaryotic cells. For example, CKSRP genes can be expressed in bacterial cells such as *C. glutamicum*, insect cells (using baculovirus expression vectors), yeast and other fungal cells (See Romanos, M. A. et al., 1992, Foreign gene expression in yeast: a review, Yeast 8:423-488; van den Hondel, C.A.M.J.J. et al., 1991, Heterologous gene expression in filamentous fungi, in: More Gene Manipulations in Fungi, J. W. Bennet & L. L. Lasure, eds., p. 396-428: Academic Press: San Diego; and van den Hondel, C.A.M.J.J. & Punt, P. J., 1991, Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999, Marine Biotechnology 1(3): 239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in PCT Application No. WO 98/01572, and multicellular plant cells (See Schmidt, R. and Willmitzer, L., 1988, High efficiency *Agrobacterium tumefaciens*-mediated transformation of *Arabidopsis thaliana* leaf and cotyledon explants, Plant Cell Rep. 583-586; Plant Molecular Biology and Biotechnology, C Press, Boca Raton, Fla., chapter 6/7, S.71-119 (1993); F. F. White, B. Jenes et al., Techniques for Gene Transfer, in: Transgenic Plants, Vol. 1, Engineering and Utilization, eds. Kung und R. Wu, 128-43, Academic Press: 1993; Potrykus, 1991, Annu. Rev. Plant Physiol. Plant Molec. Biol. 42:205-225 and references cited therein), or mammalian cells. Suitable host cells are discussed further in Goeddel, Gene Expression Technology: Methods in Enzymology 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith, D. B. and Johnson, K. S., 1988, Gene 67:31-40), pMAL (New England Biolabs, Beverly, Mass.), and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the CKSRP is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant CKSRP unfused to GST can be recovered by cleavage of the fusion polypeptide with thrombin.

Examples of suitable inducible non-fusion E. coli expression vectors include pTrc (Amann et al., 1988, Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident γ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, S., Gene Expression Technology: Methods in Enzymology 185, Academic Press, San Diego, Calif. (1990) 119-128). Another strategy is to alter the sequence of the nucleic acid to be inserted into an expression vector so that the individual codons for each amino acid are those preferentially utilized in the bacterium chosen for expression, such as C. glutamicum (Wada et al., 1992, Nucleic Acids Res. 20:2111-2118). Such alteration of nucleic acid sequences of the invention can be carried out by standard DNA synthesis techniques.

In another embodiment, the CKSRP expression vector is a yeast expression vector. Examples of vectors for expression in yeast S. cerevisiae include pYepSec1 (Baldari, et al., 1987, EMBO J. 6:229-234), pMFa (Kurjan and Herskowitz, 1982, Cell 30:933-943), pJRY88 (Schultz et al., 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C.A.M.J.J. & Punt, P. J., 1991, "Gene transfer systems and vector development for filamentous fungi," in: Applied Molecular Genetics of Fungi, J. F. Peberdy, et al., eds., p. 1-28, Cambridge University Press: Cambridge.

Alternatively, the CKSRPs of the invention can be expressed in insect cells using baculovirus expression vectors. Baculovirus vectors available for expression of polypeptides in cultured insect cells (e.g., Sf 9 cells) include the pAc series (Smith et al., 1983, Mol. Cell Biol. 3:2156-2165) and the pVL series (Lucklow and Summers, 1989, Virology 170: 31-39).

In yet another embodiment, a CKSRP nucleic acid of the invention is expressed in mammalian cells using a mammalian expression vector. Examples of mammalian expression vectors include pCDM8 (Seed, B., 1987, Nature 329:840) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual. latest ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268-277), lymphoid-specific promoters (Calame and Eaton, 1988, Adv. Immunol. 43:235-275), in particular promoters of T cell receptors (Winoto and Baltimore, 1989, EMBO J. 8:729-733), and immunoglobulins (Banerji et al., 1983, Cell 33:729-740; Queen and Baltimore, 1983, Cell 33:741-748), neuron-specific promoters (e.g., the neurofilament promoter; Byrne and Ruddle, 1989, PNAS 86:5473-5477), pancreas-specific promoters (Edlund et al., 1985, Science 230:912-916), and mammary gland-specific promoters (e.g., milk whey promoter; U.S. Pat. No. 4,873,316 and European Application Publication No. 264, 166). Developmentally-regulated promoters are also encompassed, for example, the murine hox promoters (Kessel and Gruss, 1990, Science 249:374-379) and the fetopolypeptide promoter (Campes and Tilghman, 1989, Genes Dev. 3:537-546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics or herbicides) is generally introduced into the host cells along with the gene of interest. Preferred selectable markers include those that confer resistance to drugs, such as G418, hygromycin, and methotrexate, or in plants that confer resistance towards an herbicide such as glyphosate, glufosinate, or imidazolinone. Nucleic acid molecules encoding a selectable marker can be introduced into a host cell on the same vector as that encoding a CKSRP or can be introduced on a separate vector. Cells stably transfected with the introduced nucleic acid molecule can be identified by, for example, herbicide selection (e.g., cells that have incorporated the selectable marker gene will survive, while the other cells die).

In a preferred embodiment of the present invention, the CKSRPs are expressed in plants and plants cells such as unicellular plant cells (e.g. algae) (See Falciatore et al., 1999, Marine Biotechnology 1(3):239-251 and references therein) and plant cells from higher plants (e.g., the spermatophytes, such as crop plants). A CKSRP may be "introduced" into a plant cell by any means, including transfection, transformation or transduction, electroporation, particle bombardment, agroinfection, and the like. One transformation method known to those of skill in the art is the dipping of a flowering plant into an *Agrobacteria* solution, wherein the *Agrobacteria* contain the CKSRP nucleic acid, followed by breeding of the transformed gametes.

Other suitable methods for transforming or transfecting host cells including plant cells can be found in Sambrook, et al. (Molecular Cloning: A Laboratory Manual. latest ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses, and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a CKSRP into a plant is achieved by *Agrobacterium* mediated gene transfer. *Agrobacterium* mediated plant transformation can be performed using for example the GV3101(pMP90) (Koncz and Schell, 1986, Mol. Gen. Genet. 204:383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced CKSRP may be maintained in the plant cell stably if it is incorporated into a non-chromosomal autonomous replicon or integrated into the plant chromosomes. Alternatively, the introduced CKSRP may be present on an extra-chromosomal non-replicating vector and may be transiently expressed or transiently active.

In one embodiment, a homologous recombinant microorganism can be created wherein the CKSRP is integrated into a chromosome, a vector is prepared which contains at least a portion of a CKSRP gene into which a deletion, addition, or substitution has been introduced to thereby alter, e.g., functionally disrupt, the CKSRP gene. Preferably, the CKSRP gene is a *Physcomitrella patens, Brassica napus, Glycine max,* or *Oryza sativa* CKSRP gene, but it can be a homolog from a related plant or even from a mammalian, yeast, or insect source. In one embodiment, the vector is designed such that, upon homologous recombination, the endogenous CKSRP gene is functionally disrupted (i.e., no longer encodes a functional polypeptide; also referred to as a knockout vector). Alternatively, the vector can be designed such that, upon homologous recombination, the endogenous CKSRP gene is mutated or otherwise altered but still encodes a functional polypeptide (e.g., the upstream regulatory region can be altered to thereby alter the expression of the endogenous CKSRP). To create a point mutation via homologous recombination, DNA-RNA hybrids can be used in a technique known as chimeraplasty (Cole-Strauss et al., 1999, Nucleic Acids Research 27(5):1323-1330 and Kmiec, 1999, Gene Therapy American Scientist 87(3):240-247). Homologous recombination procedures in *Physcomitrella patens* are also well known in the art and are contemplated for use herein.

Whereas in the homologous recombination vector, the altered portion of the CKSRP gene is flanked at its 5' and 3' ends by an additional nucleic acid molecule of the CKSRP gene to allow for homologous recombination to occur between the exogenous CKSRP gene carried by the vector and an endogenous CKSRP gene, in a microorganism or plant. The additional flanking CKSRP nucleic acid molecule is of sufficient length for successful homologous recombination with the endogenous gene. Typically, several hundreds of base pairs up to kilobases of flanking DNA (both at the 5' and 3' ends) are included in the vector (See e.g., Thomas, K. R., and Capecchi, M. R., 1987, Cell 51:503 for a description of homologous recombination vectors or Strepp et al., 1998, PNAS, 95(8):4368-4373 for cDNA based recombination in *Physcomitrella patens*). The vector is introduced into a microorganism or plant cell (e.g., via polyethylene glycol mediated DNA), and cells in which the introduced CKSRP gene has homologously recombined with the endogenous CKSRP gene are selected using art-known techniques.

In another embodiment, recombinant microorganisms can be produced that contain selected systems that allow for regulated expression of the introduced gene. For example, inclusion of a CKSRP gene on a vector placing it under control of the lac operon permits expression of the CKSRP gene only in the presence of IPTG. Such regulatory systems are well known in the art.

Whether present in an extra-chromosomal non-replicating vector or a vector that is integrated into a chromosome, the CKSRP polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker, D., Kemper, E., Schell, J. and Masterson, R., 1992, New plant binary vectors with selectable markers located proximal to the left border, Plant Mol. Biol. 20: 1195-1197; and Bevan, M. W., 1984, Binary *Agrobacterium* vectors for plant transformation, Nucl. Acid. Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operatively linked to an appropriate promoter conferring gene expression in a timely, cell specific, or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35 S promoters (Odell et al., 1985, Nature 313:810-812), the sX CaMV $^{35}$S promoter (Kay et al., 1987, Science 236:1299-1302) the Sep1 promoter, the rice actin promoter (McElroy et al., 1990, Plant Cell 2:163-171), the *Arabidopsis* actin promoter, the ubiquitan promoter (Christensen et al., 1989, Plant Molec. Biol. 18:675-689), pEmu (Last et al., 1991, Theor. Appl. Genet. 81:581-588), the figwort mosaic virus 35S promoter, the Smas promoter (Velten et al., 1984, EMBO J 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are preferentially active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For review, see Gatz, 1997, Annu. Rev. Plant Physiol. Plant Mol. Biol. 48:89-108).

Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2:397-404), and an ethanol inducible promoter (PCT Application No. WO 93/21334).

In one preferred embodiment of the present invention, the inducible promoter is a stress-inducible promoter. For the purposes of the invention, stress inducible promoters are preferentially active under one or more of the following stresses: sub-optimal conditions associated with salinity, drought, temperature, metal, chemical, pathogenic, and oxidative stresses. Stress inducible promoters include, but are not limited to, Cor78 (Chak et al., 2000, Planta 210:875-883; Hovath et al., 1993, Plant Physiol. 103:1047-1053), Cor15a (Artus et al., 1996, PNAS 93(23):13404-09), Rci2A (Medina et al., 2001, Plant Physiol. 125:1655-66; Nylander et al., 2001, Plant Mol. Biol. 45:341-52; Navarre and Goffeau, 2000, EMBO J. 19:2515-24; Capel et al., 1997, Plant Physiol. 115: 569-76), Rd22 (Xiong et al., 2001, Plant Cell 13:2063-83; Abe et al., 1997, Plant Cell 9:1859-68; Iwasaki et al., 1995, Mol. Gen. Genet. 247:391-8), cDet6 (Lang and Palve, 1992, Plant Mol. Biol. 20:951-62), ADH1 (Hoeren et al., 1998, Genetics 149:479-90), KAT1 (Nakamura et al., 1995, Plant Physiol. 109:371-4), KST1 (Müller-Röber et al., 1995, EMBO 14:2409-16), Rhal (Terryn et al., 1993, Plant Cell 5:1761-9; Terryn et al., 1992, FEBS Lett. 299(3):287-90), ARSK1 (Atkinson et al., 1997, GenBank Accession # L22302, and PCT Application No. WO 97/20057), PtxA (Plesch et al., GenBank Accession # X67427), SbHRGP3 (Ahn et al., 1996, Plant Cell 8: 1477-90), GH3 (Liu et al., 1994, Plant Cell 6:645-57), the pathogen inducible PRP1-gene promoter (Ward et al., 1993, Plant. Mol. Biol. 22:361-366), the heat inducible hsp80-promoter from tomato (U.S. Pat. No. 5,187, 267), cold inducible alpha-amylase promoter from potato (PCT Application No. WO 96/12814), or the wound-inducible pinII-promoter (European Patent No. 375091). For other examples of drought, cold, and salt-inducible promoters, such as the RD29A promoter, see Yamaguchi-Shinozalei et al., 1993, Mol. Gen. Genet. 236:331-340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., 1989, BioEssays 10:108. Examples of seed preferred promoters include, but are not limited to, cellulose synthase (celA), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991, Mol. Gen. Genet. 225(3):459-67), the oleosin-promoter from *Arabidopsis* (PCT Application No. WO 98/45461), the phaseolin-promoter from *Phaseolus vulgaris*

(U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2): 233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729-736).

The invention further provides a recombinant expression vector comprising a CKSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a CKSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type, into which the vector is introduced. For a discussion of the regulation of gene expression using antisense genes, see Weintraub, H. et al., 1986, Antisense RNA as a molecular tool for genetic analysis, Reviews—Trends in Genetics, Vol. 1(1), and Mol et al., 1990, FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a CKSRP can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Other suitable host cells are known to those skilled in the art.

A host cell of the invention, such as a prokaryotic or eukaryotic host cell in culture, can be used to produce (i.e., express) a CKSRP. Accordingly, the invention further provides methods for producing CKSRPs using the host cells of the invention. In one embodiment, the method comprises culturing the host cell of invention (into which a recombinant expression vector encoding a CKSRP has been introduced, or into which genome has been introduced a gene encoding a wild-type or altered CKSRP) in a suitable medium until the CKSRP is produced. In another embodiment, the method further comprises isolating CKSRPs from the medium or the host cell.

Another aspect of the invention pertains to isolated CKSRPs, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of CKSRP in which the polypeptide is separated from some of the cellular components of the cells in which it is naturally or recombinantly produced. In one embodiment, the language "substantially free of cellular material" includes preparations of a CKSRP having less than about 30% (by dry weight) of non-CKSRP material (also referred to herein as a "contaminating polypeptide"), more preferably less than about 20% of non-CKSRP material, still more preferably less than about 10% of non-CKSRP material, and most preferably less than about 5% non-CKSRP material.

When the CKSRP or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of CKSRP in which the polypeptide is separated from chemical precursors or other chemicals that are involved in the synthesis of the polypeptide. In one embodiment, the language "substantially free of chemical precursors or other chemicals" includes preparations of a CKSRP having less than about 30% (by dry weight) of chemical precursors or non-CKSRP chemicals, more preferably less than about 20% chemical precursors or non-CKSRP chemicals, still more preferably less than about 10% chemical precursors or non-CKSRP chemicals, and most preferably less than about 5% chemical precursors or non-CKSRP chemicals. In preferred embodiments, isolated polypeptides, or biologically active portions thereof, lack contaminating polypeptides from the same organism from which the CKSRP is derived. Typically, such polypeptides are produced by recombinant expression of, for example, a *Physcomitrella patens* or *Brassica napus* CKSRP in plants other than *Physcomitrella patens* or *Brassica napus*, or microorganisms such as *C. glutamicum*, ciliates, algae, or fungi.

The nucleic acid molecules, polypeptides, polypeptide homologs, fusion polypeptides, primers, vectors, and host cells described herein can be used in one or more of the following methods: identification of *Physcomitrella patens*, *Saccharomyces cerevisiae* or *Brassica napus* and related organisms; mapping of genomes of organisms related to *Physcomitrella patens*, *Saccharomyces cerevisiae* or *Brassica napus*; identification and localization of *Physcomitrella pat-* ens, *Saccharomyces cerevisiae* or *Brassica napus* sequences of interest; evolutionary studies; determination of CKSRP regions required for function; modulation of a CKSRP activity; modulation of the metabolism of one or more cell functions; modulation of the transmembrane transport of one or more compounds; modulation of stress resistance; and modulation of expression of CKSRP nucleic acids. In one embodiment of these methods, the CKSRP functions as an active potassium transport protein. In another embodiment of these methods, the CKSRP functions as a zinc transporter.

The moss *Physcomitrella patens* is related to other mosses, such as *Ceratodon purpureus*, that are capable of growth in the absence of light. Mosses like *Ceratodon* and *Physcomitrella* share a high degree of sequence identity on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The CKSRP nucleic acid molecules of the invention have a variety of uses. Most importantly, the nucleic acid and amino acid sequences of the present invention can be used to transform plants, thereby inducing tolerance to stresses such as drought, high salinity, and cold. The present invention therefore provides a transgenic plant transformed by a CKSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and forage crops, for example.

In particular, the present invention describes using the expression of PpCk-1, PpCK-2, PpCK-4, and PpPK-4 of *Physcomitrella patens*; ScCK-1 of *Saccharomyces cerevisiae*; and BnCK-1, BnCK-2, BnCK-3, BnCK-4, and BnCK-5 of *Brassica napus* to engineer drought-tolerant, salt-tolerant, and/or cold-tolerant plants. This strategy has herein been demonstrated for *Arabidopsis thaliana*, Rapeseed/Canola, soybeans, corn, and wheat, but its application is not restricted to these plants. Accordingly, the invention provides a transgenic plant containing a CKSRP such as the PpCK-1 as defined in SEQ ID NO:4, PpCK-2 as defined in SEQ ID NO:6, PpCK-4 as defined in SEQ ID NO:2, PpPK-4 as defined in SEQ ID NO:8, ScCK-1 as defined in SEQ ID NO:10, BnCK-1 as defined in SEQ ID NO:12, BnCK-2 as defined in SEQ ID NO:14, BnCK-3 as defined in SEQ ID NO:16, BnCK-4 as defined in SEQ ID NO:18, and BnCK-5 as defined in SEQ ID NO:20, wherein the plant has an increased tolerance to an environmental stress selected from one or more of the group consisting of drought, increased salt, or decreased or increased temperature. In preferred embodiments, the environmental stress is drought or decreased temperature.

Accordingly, the invention provides a method of producing a transgenic plant with a CKSRP coding nucleic acid, wherein expression of the nucleic acid(s) in the plant results in increased tolerance to environmental stress as compared to a wild type variety of the plant comprising: (a) introducing into a plant cell an expression vector comprising a CKSRP nucleic acid, and (b) generating from the plant cell a transgenic plant with a increased tolerance to environmental stress as compared to a wild type variety of the plant. The plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. In preferred embodiments, the CKSRP nucleic acid encodes a protein comprising the polypeptide of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20.

The present invention also provides a method of modulating a plant's tolerance to an environmental stress comprising, modifying the expression of a CKSRP coding nucleic acid in the plant. The plant's tolerance to the environmental stress can be increased or decreased as achieved by increasing or decreasing the expression of a CKSRP, respectively. Preferably, the plant's tolerance to the environmental stress is increased by increasing expression of a CKSRP. Expression of a CKSRP can be modified by any method known to those of skill in the art. The methods of increasing expression of CKSRPs can be used wherein the plant is either transgenic or not transgenic. In cases when the plant is transgenic, the plant can be transformed with a vector containing any of the above described CKSRP coding nucleic acids, or the plant can be transformed with a promoter that directs expression of native CKSRP in the plant, for example. The invention provides that such a promoter can be tissue preferred, developmentally regulated, stress inducible, or a combination thereof. Alternatively, non-transgenic plants can have native CKSRP expression modified by inducing a native promoter. The expression of PpCK-1 as defined in SEQ ID NO:4, PpCK-2 as defined in SEQ ID NO:6, PpCK-4 as defined in SEQ ID NO:2, PpPK-4 as defined in SEQ ID NO:8, ScCK-1 as defined in SEQ ID NO:10, BnCK-1 as defined in SEQ ID NO:12, BnCK-2 as defined in SEQ ID NO:14, BnCK-3 as defined in SEQ ID NO:16, BnCK-4 as defined in SEQ ID NO:18, or BnCK-5 as defined in SEQ ID NO:20 in target plants can be accomplished by, but is not limited to, one of the following examples: (a) constitutive promoter, (b) stress-inducible promoter, (c) chemical-induced promoter, and (d) engineered promoter overexpression with, for example, zinc-finger derived transcription factors (Greisman and Pabo, 1997, Science 275:657).

In a preferred embodiment, transcription of the CKSRP is modulated using zinc-finger derived transcription factors (ZFPs) as described in Greisman and Pabo, 1997, Science 275:657 and manufactured by Sangamo Biosciences, Inc. These ZFPs comprise both a DNA recognition domain and a functional domain that causes activation or repression of a target nucleic acid such as a CKSRP nucleic acid. Therefore, activating and repressing ZFPs can be created that specifically recognize the CKSRP promoters described above and used to increase or decrease CKSRP expression in a plant, thereby modulating the stress tolerance of the plant. The present invention also includes identification of the homologs of PpCK-1 as defined in SEQ ID NO:4, PpCK-2 as defined in SEQ ID NO:6, PpCK-4 as defined in SEQ ID NO:2, PpPK-4 as defined in SEQ ID NO:8, ScCK-1 as defined in SEQ ID NO:10, BnCK-1 as defined in SEQ ID NO:12, BnCK-2 as defined in SEQ ID NO:14, BnCK-3 as defined in SEQ ID NO:16, BnCK-4 as defined in SEQ ID NO:18, and BnCK-5 as defined in SEQ ID NO:20 in a target plant, as well as the homolog's promoter. The invention also provides a method of increasing expression of a gene of interest within a host cell as compared to a wild type variety of the host cell, wherein the gene of interest is transcribed in response to a CKSRP, comprising: (a) transforming the host cell with an expression vector comprising a CKSRP coding nucleic acid, and (b) expressing the CKSRP within the host cell, thereby increasing the expression of the gene transcribed in response to the CKSRP, as compared to a wild type variety of the host cell.

In addition to introducing the CKSRP nucleic acid sequences into transgenic plants, these sequences can also be used to identify an organism as being *Physcomitrella patens*, *Brassica napus*, *Saccharomyces cerevisiae*, or a close relative thereof. Also, they may be used to identify the presence of *Physcomitrella patens*, *Brassica napus*, *Saccharomyces cerevisiae*, or a relative thereof in a mixed population of microorganisms. The invention provides the nucleic acid sequences of a number of *Physcomitrella patens*, *Brassica napus*, and *Saccharomyces cerevisiae* genes; by probing the extracted genomic DNA of a culture of a unique or mixed population of microorganisms under stringent conditions with a probe spanning a region of a *Physcomitrella patens*, *Brassica napus*, or *Saccharomyces cerevisiae* gene that is unique to this organism, one can ascertain whether this organism is present.

Further, the nucleic acid and polypeptide molecules of the invention may serve as markers for specific regions of the genome. This has utility not only in the mapping of the genome, but also in functional studies of *Physcomitrella patens*, *Brassica napus*, or *Saccharomyces cerevisiae* polypeptides. For example, to identify the region of the genome to which a particular *Physcomitrella patens* DNA-binding polypeptide binds, the *Physcomitrella patens* genome could be digested, and the fragments incubated with the DNA-binding polypeptide. Those fragments that bind the polypeptide may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the polypeptide binds. Further, the nucleic acid molecules of the invention may be sufficiently identical to the sequences of related species such that these nucleic acid molecules may serve as markers for the construction of a genomic map in related mosses.

The CKSRP nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the CKSRP nucleic acid molecules of the invention may result in the production of CKSRPs having functional differences from the wild-type CKSRPs. These polypeptides may be improved in efficiency or activity, may be present in greater numbers in the cell than is usual, or may be decreased in efficiency or activity.

There are a number of mechanisms by which the alteration of a CKSRP of the invention may directly affect stress response and/or stress tolerance. In the case of plants expressing CKSRPs, increased transport can lead to improved salt and/or solute partitioning within the plant tissue and organs. By either increasing the number or the activity of transporter molecules that export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim; Belter, P. A. et al., 1988, Bioseparations: downstream processing for biotechnology, John Wiley and Sons; Kennedy, J. F. and Cabral, J. M. S., 1992, Recovery processes for biological materials, John Wiley and Sons; Shaeiwitz, J. A. and Henry, J. D., 1988, Biochemical separations, in: Ulmann's Encyclopedia of Industrial Chemistry, vol. B3, Chapter 11, page 1-27, VCH: Weinheim; and Dechow, F. J., 1989, Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stresses. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their tolerance to drought, salt, and temperature stresses.

The engineering of one or more CKSRP genes of the invention may also result in CKSRPs having altered activities, which indirectly impact the stress response and/or stress tolerance of algae, plants, ciliates, or fungi, or other microorganisms like *C. glutamicum*. For example, the normal biochemical processes of metabolism result in the production of a variety of products (e.g., hydrogen peroxide and other reactive oxygen species), which may actively interfere with these same metabolic processes. For example, peroxynitrite is known to nitrate tyrosine side chains, thereby inactivating some enzymes having tyrosine in the active site (Groves, J. T., 1999, Curr. Opin. Chem. Biol. 3(2):226-235). While these products are typically excreted, cells can be genetically altered to transport more products than is typical for a wild-type cell. By optimizing the activity of one or more CKSRPs of the invention that are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998, The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation, see U.S. Pat. No. 6,004, 804 "Non-Chimeric Mutational Vectors" and Puttaraju et al., 1999, Spliceosome-mediated RNA trans-splicing as a tool for gene therapy, Nature Biotechnology 17:246-252.

The aforementioned mutagenesis strategies for CKSRPs resulting in increased stress resistance are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi, or other microorganisms like C. glutamicum expressing mutated CKSRP nucleic acid and polypeptide molecules such that the stress tolerance is improved.

The present invention also provides antibodies that specifically bind to a CKSRP, or a portion thereof, as encoded by a nucleic acid described herein. Antibodies can be made by many well-known methods (See, e.g., Harlow and Lane, "Antibodies; A Laboratory Manual," Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992, Bio/Technology 10:163-167; Bebbington et al., 1992, Bio/Technology 10:169-175).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York, 1988.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of Physcomitrella patens Cultures

For this study, plants of the species Physcomitrella patens (Hedw.) B.S.G. from the collection of the genetic studies section of the University of Hamburg were used. They originate from the strain 16/14 collected by H.L.K. Whitehouse in Gransden Wood, Huntingdonshire (England), which was subcultured from a spore by Engel (1968, Am. J. Bot. 55, 438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromols m$^{-2}$ s$^{-1}$ (white light; Philips TL 65W/25 fluorescent tube) and a light/dark change of 16/8 hours. The moss was either modified in liquid culture using Knop medium according to Reski and Abel (1985, Planta 165:354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; and 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol, and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 μl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 μl of H$_2$O+RNAse (50 mg/ml final concentration). The DNA was dissolved overnight at 4° C., and the RNAse digestion was subsequently carried out at 37° C. for 1 hour. Storage of the DNA took place at 4° C.

Example 3

Isolation of Total RNA and poly-(A)$^+$ RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al., 1994, Mol. Gen. Genet., 244:352-359). The Poly(A)$^+$ RNA was isolated using Dyna Beads® (Dynal, Oslo, Norway) following the instructions of the manufacturer's protocol. After determination of the concentration of the RNA or of the poly(A)$^+$ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour), and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany), and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (See Sambrook et al., 1989, Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'      SEQ ID NO:21

5'-CTAAAGGGAACAAAAGCTG-3'     SEQ ID NO:22

5'-TGTAAAACGACGGCCAGT-3'      SEQ ID NO:23
```

Sequences were processed and annotated using the software package EST-MAX commercially provided by Bio-Max (Munich, Germany). The program incorporates practically all bioinformatics methods important for functional and structural characterization of protein sequences. For reference, see the website at pedant.mips.biochem.mpg.de. The most important algorithms incorporated in EST-MAX are: FASTA (Very sensitive sequence database searches with estimates of statistical significance; Pearson W. R., 1990, Rapid and sensitive sequence comparison with FASTP and FASTA. Methods Enzymol. 183:63-98); BLAST (Very sensitive sequence database searches with estimates of statistical significance. Altschul S. F. et al., Basic local alignment search tool, Journal of Molecular Biology 215:403-10); PREDATOR (High-accuracy secondary structure prediction from single and multiple sequences. Frishman, D. and Argos, P., 1997, 75% accuracy in protein secondary structure prediction. Proteins, 27:329-335); CLUSTALW: Multiple sequence alignment. Thompson, J. D. et al., 1994, CLUSTAL W (improving the sensitivity of progressive multiple sequence alignment through sequence weighting, positions-specific gap penalties and weight matrix choice, Nucleic Acids Research, 22:4673-4680); TMAP (Transmembrane region prediction from multiply aligned sequences. Persson, B. and Argos, P., 1994, Prediction of transmembrane segments in proteins utilizing multiple sequence alignments. J. Mol. Biol. 237:182-192); ALOM2 (Transmembrane region prediction from single sequences. Klein, P. et al., Prediction of protein function from sequence properties: A discriminate analysis of a database. Biochim. Biophys. Acta 787:221-226 (1984). Version 2 by Dr. K. Nakai); PROSEARCH (Detection of PROSITE protein sequence patterns. Kolakowski L. F. Jr., Leunissen J. A. M., Smith J. E., 1992, ProSearch: fast searching of protein sequences with regular expression patterns related to protein structure and function. Biotechniques 13, 919-921); BLIMPS (Similarity searches against a database of ungapped blocks, J. C. Wallace and Henikoff S., 1992); PATMAT (a searching and extraction program for sequence, pattern and block queries and databases, CABIOS 8:249-254. Written by Bill Alford).

Example 5

Identification of *Physcomitrella patens* ORFs corresponding to PpCK-1, PpCK-2, PpCK-4, and PpPK-4

The *Physcomitrella patens* partial cDNAs (ESTs) for partial PpCK-1, PpCK-2, PpCK-4, and PpPK-4 were identified in the *Physcomitrella patens* EST sequencing program using the program EST-MAX through BLAST analysis. These particular clones, which were found to encode Protein Kinases, were chosen for further analyses.

TABLE 2

Degree of Amino Acid Identity and Similarity of PpCK-1 and Other Kinases (Pairwise Comparison was used: gap penalty: 10; gap extension penalty: 0.1; score matrix: blosum62)

| | Swiss-Prot # | | | | |
|---|---|---|---|---|---|
| | Q8LR51 | T04265 | Q8VYK9 | B84577 | H96751 |
| Polypeptide name | Putative Casein Kinase I- | Probable Kasein Kinase | Putatitive Col-0 Casein Kinase I | Probable Casein Kinase I | Probable Casein Kinase I |
| Species | Oryza sativa | Arabidopsis thaliana | Arabidopsis thaliana | Arabidopsis thaliana | Arabidopsis thaliana |
| Identity % | 32.9 | 34.3 | 34.3 | 34.4 | 31.4 |
| Similarity % | 42.4 | 43.2 | 43.2 | 43.9 | 40.9 |

TABLE 3

Degree of Amino Acid Identity and Similarity of PpCK-2 and Other Kinases (Pairwise Comparison was used: gap penalty: 10; gap extension penalty: 0.1; score matrix: blosum62)

| | Swiss-Prot # | | | | |
|---|---|---|---|---|---|
| | Q8LR51 | T04265 | Q8VYK9 | Q8S1A8 | H96751 |
| Polypeptide name | Putative Casein Kinase I- | Probable Kasein Kinase | Putatitive Col-0 Casein Kinase I | Putative Casein Kinase | Probable Casein Kinase I |
| Species | Oryza sativa | Arabidopsis thaliana | Arabidopsis thaliana | Oryza sativa | Arabidopsis thaliana |
| Identity % | 67.6 | 63.9 | 63.9 | 61.7 | 64.3 |
| Similarity % | 76.6 | 73.3 | 73.3 | 71.0 | 73.8 |

TABLE 4

Degree of Amino Acid Identity and Similarity of PpCK-4 and Other Kinases (Pairwise Comparison was used: gap penalty: 10; gap extension penalty: 0.1; score matrix: blosum62)

| | Swiss-Prot # | | | | |
|---|---|---|---|---|---|
| | Q8LR51 | T04265 | Q8S1A8 | Q8VYK9 | H96751 |
| Polypeptide name | Putative Casein Kinase I- | Probable Kasein Kinase | Putative Casein Kinase | Putatitive Col-0 Casein Kinase I | Probable Casein Kinase I |
| Species | Oryza sativa | Arabidopsis thaliana | Oryza sativa | Arabidopsis thaliana | Arabidopsis thaliana |
| Identity % | 62.8 | 62.1 | 59.4 | 62.1 | 62.6 |
| Similarity % | 72.9 | 71.7 | 68.3 | 71.7 | 71.5 |

TABLE 5

Degree of Amino Acid Identity and Similarity of PpPK-4 and Other Kinases (Pairwise Comparison was used: gap penalty: 10; gap extension penalty: 0.1; score matrix: blosum62)

| | Swiss-Prot # | | | | |
|---|---|---|---|---|---|
| | Q9SZI1 | Q9ZUP4 | P42158 | Q39050 | Q9LW62 |
| Polypeptide name | COL-0 Casein Kinase I-Like Protein | Putative Casein Kinase I | Casein Kinase I, Delta Isoform Like | Casein Kinase I | Casein Kinase |
| Species | Arabidopsis thaliana | Arabidopsis thaliana | Arabidopsis thaliana | Arabidopsis thaliana | Arabidopsis thaliana |
| Identity % | 35% | 35% | 37% | 35% | 35% |
| Similarity % | 46% | 44% | 47% | 45% | 44% |

Example 6

Cloning of the Full-Length *Physcomitrella patens* cDNA Encoding for PpCK-1, PpCK-2, PpCK-4, and PpPK-4

To isolate the clones encoding PpCK-1 (SEQ ID NO:3), PpCK-2 (SEQ ID NO:5), PpCK-4 (SEQ ID NO:1), and PpPK-4 (SEQ ID NO:7) from *Physcomitrella patens*, cDNA libraries were created with SMART RACE cDNA Amplification kit (Clontech Laboratories) following the manufacturer's instructions. Total RNA isolated as described in Example 3 was used as the template. The cultures were treated prior to RNA isolation as follows: Salt Stress: 2, 6, 12, 24, 48 hours with 1-M NaCl-supplemented medium; Cold Stress: 4° C. for the same time points as for salt; Drought Stress: cultures were incubated on dry filter paper for the same time points as for salt.

5' RACE Protocol. The EST sequences of PpCK-1, PpCK-2, PpCK-4, and PpPK-4 identified from the database search as described in Example 5 were used to design oligos for RACE (See Table 6). The extended sequence for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions. The sequences obtained from the RACE reactions corresponded to full-length coding region of PpCK-1, PpCK-2, PpCK-4, and PpPK-4 were used to design oligos for full-length cloning of the respective gene (See below Full-Length Amplification).

Full-length Amplification. Full-length clones corresponding to PpCK-1, PpCK-2, and PpCK-4 were obtained by performing polymerase chain reaction (PCR) with gene-specific primers (See Table 6) and the original EST as the template. The conditions for the reaction were standard conditions with PWO DNA polymerase (Roche). PCR was performed according to standard conditions and to manufacturer's protocols (Sambrook et al., 1989, Molecular Cloning, A Laboratory Manual, 2nd Edition, Cold Spring Harbor Laboratory Press, Cold Spring Harbor, N.Y., Biometra T3 Thermocycler). The parameters for the reaction were: five minutes at 94° C. followed by five cycles of one minute at 94° C., one minute at 50° C., and 1.5 minutes at 72° C. This was followed by 25 cycles of one minute at 94° C., one minute at 65° C., and 1.5 minutes at 72° C.

Full-length clones for PpPK-4 (SEQ ID NO:7) were isolated by repeating the RACE method but using the gene-specific primers as given in Table 6.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top 10 cells (Invitrogen) using standard conditions (Sambrook et al., 1989, Molecular Cloning, A Laboratory Manual. 2nd Edition, Cold Spring Harbor Laboratory Press, Cold Spring Harbor, N.Y.). Transformed cells were selected for on LB agar containing 100 mg/ml carbenicillin, 0.8 mg X-gal (5-bromo-4-chloro-3-indolyl-β-D-galactoside), and 0.8 mg IPTG (isopropylthio-b-D-galactoside) grown overnight at 37° C. White colonies were selected and used to inoculate 3 ml of liquid LB containing 100 mg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989, Molecular Cloning, A Laboratory Manual, 2nd Edition, Cold Spring Harbor Laboratory Press, Cold Spring Harbor, N.Y.).

TABLE 6

Scheme and primers used for cloning of full-length clones

| Gene | Final product Sites | Isolation Method | Primers Race | Primers RT-PCR |
|---|---|---|---|---|
| PpCK-1 | XmaI/HpaI | 5' RACE and RT-PCR for Full-length clone | NVT: (SEQ ID NO:24) CGACCGCAGCCCA TGAGGAAGTTAT | RC614: (SEQ ID NO:25) ATCCCGGGCTCACG TAGTGCACTGAACT CTGTC RC615: (SEQ ID NO:26) GCGTTAACATGCCC ATCTTCTCATACTC AGACC |
| PpCK-2 | XmaI/HpaI | 5' RACE and RT-PCR for Full-length clone | NVT: (SEQ ID NO:27) CTCGCCTACCAAG CCCCATTAGAAA | RC1012: (SEQ ID NO:28) ATCCCGGGTTGTCG AGGACGGAGAGAG AAGAG RC1015: (SEQ ID NO:29) GCGTTAACCTTAGG AATCGTATGGCAG AGAGCT |
| PpCK-4 | XmaI/HpaI | 5' RACE and RT-PCR for Full-length clone | NVT: (SEQ ID NO:44) GCCTGCCTAGCCC CATCAAGAAATT | RC598: (SEQ ID NO:45) ATCCCGGGCGCAG CATGTGACTCGTCA CCTG RC599: (SEQ ID NO:46) GCGTTAACAGCTAC TACTTGCTCTAGGA AGCTG |
| PpPK-4 | XmaI/EcoRV | 5' RACE and RT-PCR for Full-length clone | RC072: 5'TGTGTCTACG TGTCGCGGGTC GAT3' (SEQ ID NO:30) | RC133N: 5'ATCCCGGGAGGC ATTGAACTACCTGG AGTGAG3' (SEQ ID NO:31) RC134N: 5'GCGATATCGTTG AACTAGTAATCTGT GTTAACTT3' (SEQ ID NO:32) |

Example 7

Identification of *Saccharomyces cerevisiae* ORF Corresponding to ScCK-1

The ORF 760 gene from *Saccharamyces cerevisiae*, encoding a casein kinase I, was first described in European Patent Application No. 03022225.1 by Metanomics, Inc. filed Sep. 30, 2003. The Metanomics patent application is hereby incorporated by reference in its entirety. The ORF 760 gene was isolated using the standard protocol of Pfu DNA polymerase or a PfuITaq DNA polymerase mix (Herculase) for the amplification procedure. Amplified ORF fragments were analyzed by gel electrophoresis. Each primer consists of a universal 5' end and ORF specific 3' end whereby the universal sequences differ for the forward and reverse primers (Forward primer sequence contained an EcoRI for yeast or SmaI for *E. coli* and the reverse primer sequence a SmaI for yeast or SacI for *E. coli* allowing a unidirectional cloning. PCR reactions for the amplification included: 1×PCR buffer, 0.2 mM dNTP, 100 ng *Saccharomyces cerevisiae* genomic DNA (S288C) or 60 ng genomic DNA *Escherichia coli* K-12 (MG1655), 25 pmol reverse primer, 2.5 u Pfu or Herculase DNA polymerase. The conditions consisted of: 1 cycle for 3' at 94° C.; followed by 25 cycles of 30" at 94° C., 30" at 55° C., and 5-6' at 72° C.; followed by 1 cycle for 610' at 72° C., then at 4° C. indefinitely. The forward sequence for ScCK-1 (ORF 760) is 5'-GGAATTCCAGCTGACCACCA TGTCCCAAC-GATCTTCACAACAC-3' (SEQ ID NO:33). The reverse sequence for ScCK-1 (ORF 760) is 5'-GATCCCCGGGAAT-TGCCATGTCAAAAAAAAAAAGGAAAAA GAGAAAAG-3' (SEQ ID NO:34).

Example 8

Identification of *Brassica napus* ORFs Corresponding to BnCK-1, BnCK-2, BnCK-3, BnCK-4, and BnCK-5

Tissue harvest, RNA isolation, and cDNA library construction

Canola plants were grown under a variety of conditions and treatments, and different tissues were harvested at various developmental stages. Plant growth and harvesting were done in a strategic manner such that the probability of harvesting all expressible genes in at least one or more of the resulting libraries is maximized. The mRNA was isolated as described in Example 3 from each of the collected samples, and cDNA libraries were constructed. No amplification steps were used in the library production process in order to minimize redundancy of genes within the sample and to retain expression information. All libraries were 3' generated from mRNA purified on oligo dT columns. Colonies from the transformation of the cDNA library into *E. coli* were randomly picked and placed into microtiter plates.

Probe Hybridization. Plasmid DNA was isolated from the *E. coli* colonies and then spotted on membranes. A battery of 288 $^{33}$P radiolabeled 7-mer oligonucleotides were sequentially hybridized to these membranes. To increase throughput, duplicate membranes were processed. After each hybridization, a blot image was captured during a phosphorimage scan to generate a hybridization profile for each oligonucleotide. This raw data image was automatically transferred via LIMS to a computer. Absolute identity was maintained by barcoding for the image cassette, filter, and orientation within the cassette. The filters were then treated using relatively mild conditions to strip the bound probes and returned to the hybridization chambers for another round of hybridization. The hybridization and imaging cycle was repeated until the set of 288 oligomers was completed.

After completion of the hybridizations, a profile was generated for each spot (representing a cDNA insert), as to which of the 288 $^{33}$P radiolabeled 7-mer oligonucleotides bound to that particular spot (cDNA insert), and to what degree. This profile is defined as the signature generated from that clone. Each clone's signature was compared with all other signatures generated from the same organism to identify clusters of related signatures. This process "sorts" all of the clones from an organism into clusters before sequencing.

Gene Isolation. The clones were sorted into various clusters based on their having identical or similar hybridization signatures. A cluster should be indicative of the expression of an individual gene or gene family. A by-product of this analysis is an expression profile for the abundance of each gene in a particular library. One-path sequencing from the 5' end was used to predict the function of the particular clones by similarity and motif searches in sequence databases.

The full-length DNA sequence of the *Saccharomyces cerevisiae* ScCK-1 (SEQ ID NO:9) was blasted against proprietary contig databases of canola at E value of E-10. (Altschul, Stephen et al., Gapped BLAST and PSI_BLAST: a new generation of protein database search program, Nucleic Acids Res. 25: 3389-3402). All the contig hits were analyzed for the putative full-length sequences, and the longest clones representing the putative full-length contigs were fully sequenced. Five such contigs isolated from the proprietary contig databases are BnCK-1, BnCK-2, BnCK-3, BnCK-4, and BnCK-5. The homology of the BnCK-1, BnCK-2, BnCK-3, BnCK-4, and BnCK-5 amino acid sequences to the closest known prior art is indicated in Tables 8-12.

TABLE 8

Degree of Amino Acid Identity and Similarity of BnCK-1 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnCK-1 | Q93Z18 | Ser/Thr protein kinase | *Arabidopsis thaliana* | 53.9 | 65.1 |

TABLE 9

Degree of Amino Acid Identity and Similarity of BnCK-2 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnCK-2 | NP_680447 | Putative casein kinase | *Arabidopsis thaliana* | 91.3 | 94.7 |

TABLE 10

Degree of Amino Acid Identity and Similarity of BnCK-3 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnCK-3 | NP_567812 | Putative casein kinase | *Arabidopsis thaliana* | 92.5 | 95.6 |

TABLE 11

Degree of Amino Acid Identity and Similarity of BnCK-4 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnCK-4 | Q9SE85 | Casein kinase I like protein | *Brassica oleracea* | 91.2 | 91.4 |

TABLE 12

Degree of Amino Acid Identity and Similarity of BnCK-5 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnCK-5 | NP_197320 | Protein kinase family protein | Arabidopsis thaliana | 70.2 | 73.5 |

Example 9

Engineering Stress-Tolerant *Arabidopsis* Plants by Overexpressing the Genes PpCK-1, PpCK-2, PpCK-4, PpPK-4, ScCK-1, BnCK-1, BnCK-2, BnCK-3, BnCK-4, and BnCK-5

Binary vector construction: pBPS-JH001

The plasmid construct pLMNC53 (Mankin, 2000, Ph.D. thesis, University of North Carolina) was digested with HindIII (Roche) and blunt-end filled with Klenow enzyme and 0.1 mM dNTPs according to manufacturer's instructions. This fragment was purified by agarose gel and extracted via the QIAquick Gel Extraction kit (Qiagen) according to manufacturer's instructions. The purified fragment was then digested with EcoRI (Roche), purified by agarose gel, and extracted via the QIAquick Gel Extraction kit (Qiagen) according to manufacturer's instructions. The resulting 1.4 kilobase fragment, the gentamycin cassette, included the nos promoter, aacCI gene, and the g7 terminator.

The vector pBlueScript was digested with EcoRI and SmaI (Roche) according to manufacturer's instructions, and the resulting fragment was extracted from agarose gel with a QIAquick Gel Extraction Kit (Qiagen) according to manufacturer's instructions. The digested pBlueScript vector and the gentamycin cassette fragments were ligated with T4 DNA Ligase (Roche) according to manufacturer's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping were performed according to standard molecular biology techniques (Sambrook et al., 1989, Molecular Cloning, A Laboratory Manual. 2nd Edition, Cold Spring Harbor Laboratory Press, Cold Spring Harbor, N.Y.).

Both the pGMBS vector and p1bxSuperGUS vector were digested with XbaI and KpnI (Roche) according to manufacturer's instructions, excising the gentamycin cassette from pGMBS and producing the backbone from the p1bxSuperGUS vector. The resulting fragments were extracted from agarose gel with a QIAquick Gel Extraction Kit (Qiagen) according to manufacturer's instructions. These two fragments were ligated with T4 DNA ligase (Roche) according to manufacturer's instructions.

The resulting recombinant vector (pBPS-JH001) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping were performed according to standard molecular biology techniques (Sambrook et al., 1989, Molecular Cloning, A Laboratory Manual, 2nd Edition, Cold Spring Harbor Laboratory Press, Cold Spring Harbor, N.Y.).

Binary vector construction: pBPS-SC022. The plasmid construct pACGH101 was digested with PstI (Roche) and FseI (NEB) according to manufacturers' instructions. The fragment was purified by agarose gel and extracted via the Qiaex II DNA Extraction kit (Qiagen). This resulted in a vector fragment with the *Arabidopsis* Actin2 promoter with internal intron and the OCS3 terminator.

Primers for PCR amplification of the NPTII gene were designed [5'NPT-Pst: GCG-CTG-CAG-ATT-TCA-TTT-GGA-GAG-GAC-ACG (SEQ ID NO:35); 3'NPT-Fse: CGC-GGC-CGG-CCT-CAG-AAG-AAC-TCG-TCA-AGA-AGG-CG (SEQ ID NO:36)]. The 0.9 kilobase NPTII gene was amplified via PCR from pCambia 2301 plasmid DNA using the following parameters: 94° C. 60 sec, {94° C. 60 sec, 61° C. (−0.1° C. per cycle) 60 sec, 72° C. 2 min}×25 cycles, 72° C. 10 min on Biometra T-Gradient machine. The amplified product was purified via the Qiaquick PCR Extraction kit (Qiagen) following manufacturer's instructions. The PCR DNA was then subcloned into the pCR-BluntII TOPO vector (Invitrogen) following manufacturer's instructions (NPT-Topo construct). These ligations were transformed into Top10 cells (Invitrogen) and grown on LB plates with 50 µg/ml kanamycin sulfate overnight at 37° C. Colonies were then used to inoculate 2 ml LB media with 50 µg/ml kanamycin sulfate and grown overnight at 37° C. Plasmid DNA was recovered using the Qiaprep Spin Miniprep kit (Qiagen) and sequenced in both the 5' and 3' directions using standard conditions. Subsequent analysis of the sequence data using Vector NTI software revealed that there were not any PCR errors introduced in the NPTII gene sequence.

The NPT-Topo construct was then digested with PstI (Roche) and FseI (NEB) according to manufacturers' instructions. The 0.9 kilobase fragment was purified on agarose gel and extracted by Qiaex II DNA Extraction kit (Qiagen). The Pst/Fse insert fragment from NPT-Topo and the Pst/Fse vector fragment from pACGH101 were then ligated together using T4 DNA Ligase (Roche) following manufacturer's instructions. The ligation reaction was then transformed into Top10 cells (Invitrogen) under standard conditions, creating pBPS-sc019 construct. Colonies were selected on LB plates with 50 µg/ml kanamycin sulfate and grown overnight at 37° C. These colonies were then used to inoculate 2 ml LB media with 50 µg/ml kanamycin sulfate and grown overnight at 37° C. Plasmid DNA was recovered using the Qiaprep Spin Miniprep kit (Qiagen) following the manufacturer's instructions.

The pBPS-SC019 construct was digested with KpnI and BsaI (Roche) according to manufacturer's instructions. The fragment was purified via agarose gel and then extracted via the Qiaex II DNA Extraction kit (Qiagen) as per its instructions, resulting in a 3 kilobase Act-NPT cassette, which included the *Arabidopsis* Actin2 promoter with internal intron, the NPTII gene, and the OCS3 terminator.

The pBPS-JH001 vector was digested with SpeI and ApaI (Roche) and blunt-end filled with Klenow enzyme and 0.1 mM dNTPs (Roche) according to manufacturer's instructions. This produced a 10.1 kilobase vector fragment minus the Gentamycin cassette, which was recircularized by self-ligating with T4 DNA Ligase (Roche), and transformed into Top10 cells (Invitrogen) via standard conditions. Transformed cells were selected for on LB agar containing 50 µg/ml kanmycin sulfate and grown overnight at 37° C. Colonies were then used to inoculate 2 ml of liquid LB containing 50 µg/ml kanamycin sulfate and grown overnight at 37° C. Plasmid DNA was extracted using the QIAprep Spin Miniprep Kit (Qiagen) following manufacturer's instructions. The recircularized plasmid was then digested with KpnI (Roche) and extracted from agarose gel via the Qiaex II DNA Extraction kit (Qiagen) according to manufacturers' instructions.

The Act-NPT Kpn-cut insert and the Kpn-cut pBPS-JH001 recircularized vector were then ligated together using T4 DNA Ligase (Roche) and transformed into Top 10 cells (Invitrogen) according to manufacturers' instructions. The resulting construct, pBPS-SC022, now contained the Super Promoter, the GUS gene, the NOS terminator, and the Act-NPT cassette. Transformed cells were selected for on LB agar containing 50 µg/ml kanmycin sulfate and grown overnight at 37° C. Colonies were then used to inoculate 2 ml of liquid LB containing 50 µg/ml kanamycin sulfate and grown overnight at 37° C. Plasmid DNA was extracted using the QIAprep Spin Miniprep Kit (Qiagen) following manufacturer's instructions. After confirmation of ligation success via restriction digests, pBPS-sc022 plasmid DNA was further propagated and recovered using the Plasmid Midiprep Kit (Qiagen) following the manufacturer's instructions.

Analyses of clones by restriction mapping was performed according to standard molecular biology techniques (Sambrook et al., 1989, Molecular Cloning, A Laboratory Manual, 2nd Edition, Cold Spring Harbor Laboratory).

Subcloning of PpCK-1, PpCK-2, PpCK-4, PpPK-4, ScCK-1, BnCK-1, BnCK-2, BnCK-3, BnCK-4, and BnCK-5 into the binary vector. The fragments containing the different *Physcomitrella patens* casein kinases were excised from the recombinant PCR2.1 TOPO vectors by double digestion with restriction enzymes (See Table 13) according to manufacturer's instructions. The subsequent fragments were excised from agarose gel with a QIAquick Gel Extraction Kit (Qiagen) according to manufacturer's instructions, ligated into binary vectors, cleaved with appropriate enzymes (See Table 13), and dephosphorylated prior to ligation. The resulting recombinant vectors contained the corresponding casein kinase in the sense orientation under the control of the constitutive superpromoter.

TABLE 13

Listed are the names of the constructs of the *Physcomitrella patens* casein kinases used for plant transformation.

| Gene | Binary Vector | Enzymes used to generate gene fragment | Enzymes used to restrict binary vector | Recombinant binary vector construct |
|---|---|---|---|---|
| PpCK-1 | pBPS-SC022 | XmaI/HpaI | XmaI/Ecl136 | pBPS-SY012 |
| PpCK-2 | pBPS-SC022 | XmaI/HpaI | XmaI/Ecl136 | pBPS-JYW034 |
| PpCK-4 | pBPS-SC022 | XmaI/HpaI | XmaI/Ecl136 | pBPS-SY018 |
| PpPK-4 | pBPS-JH001 | Xma/EcoRV | XmaI/Ecl136 | pBPS-LVM015 |

Subcloning of ScCK-1 into the binary vector. The ScCK-1 gene was subcloned into a binary vector 1bxbigResgen that is based on a modified pPZP binary vector backbone. The vector comprised the kanamycin gene for bacterial selection (Hajukeiwicz et al., 1994, Plant Mol. Biol. 25:989-994) and the bar gene driven by the mas1 promoter on its T-DNA (Velten et al., 1984, EMBO J. 3: 2723-2730; Mengiste, et al., 1997, Plant J., 12: 945-948). In addition, the T-DNA contained the strong double 35S promoter (Kay et al., 1987, Science 236: 1299-1302) in front of a cloning cassette which was followed by the nos terminator (Depicker et al., J. Mol. Appl. Gen. 1(6):561-573). The cloning cassette consisted of the sequence: 5'-GGAATTCCAGCTGACCACCATGGC AAT-TCCCGGGGATC-3' (SEQ ID NO:37). Other selection systems and promoters are known in the art and are similarly capable of use in the present invention (e.g. AHAS marker, ubiquitin promoter (Callis et al., J. Biol. Chem. 1990, 265: 12486-12493; U.S. Pat. No. 5,510,474; U.S. Pat. No. 6,020, 190; Kawalleck et al., 1993, Plant Mol. Biol. 21:673-684), 34S promoter (GenBank Accession Numbers M59930 and X16673).

The binary vector and the ORF 760 gene (100 ng) were digested with EcoRI and SmaI using the standard protocol provided by the supplier (MBI Fermentas, Germany). The ORF 760 gene was purified using a Qiagen column (Qiagen, Hilden, Germany), and was ligated with the restriction digested binary vector (30 ng) using standard procedures (Maniatis et al.).

*Agrobacterium* Transformation. The recombinant vectors were transformed into *Agrobacterium tumefaciens* C58C1 and PMP90 according to standard conditions (Hoefgen and Willmitzer, 1990; Koncz and Schell, 1986, Mol. Gen. Genet. 204:383-396).

Plant Transformation. *Arabidopsis thaliana* ecotype C24 were grown and transformed according to standard conditions (Bechtold, 1993, Acad. Sci. Paris. 316:1194-1199; Bent et al., 1994, Science 265:1856-1860).

Screening of Transformed Plants Comprising *Physcomitrella* Genes. T1 seeds were sterilized according to standard protocols (Xiong et al., 1999, Plant Molecular Biology Reporter 17: 159-170). Seeds were selected on ½ Murashige and Skoog media (MS) (Sigma-Aldrich), 0.6% agar and supplemented with 1% sucrose, and 2 µg/ml benomyl (Sigma-Aldrich). Seeds on plates were vernalized for four days at 4° C. The seeds were germinated in a climatic chamber at an air temperature of 22° C. and light intensity of 40 micromols $m^{-2}s^{-1}$ (white light; Philips TL 65W/25 fluorescent tube) and 16 hours light and 8 hours dark day length cycle. Transformed seedlings were selected after 14 days and transferred to ½ MS media supplemented with 0.6% agar, 1% sucrose, and allowed to recover for five to seven days.

Drought Tolerance Screening of Transformed Plants Comprising *Physcomitrella* Genes. T1 seedlings were transferred to dry, sterile filter paper in a petri dish and allowed to desiccate for two hours at 80% RH (relative humidity) in a Sanyo Growth Cabinet MLR-350H, micromols $m^{-2}s^{-1}$ (white light; Philips TL 65W/25 fluorescent tube). The RH was then decreased to 60%, and the seedlings were desiccated further for eight hours. Seedlings were then removed and placed on ½ MS 0.6% agar plates supplemented with 2 µg/ml benomyl (Sigma-Aldrich) and scored after five days. The transgenic plants were then screened for their improved drought tolerance.

Under drought stress conditions, PpCK-1-overexpressing *Arabidopsis thaliana* plants showed a 50% survival rate to the drought stress (5 survivors from 10 stressed plants), PpCK-2-overexpressing *Arabidopsis thaliana* plants showed a 52% survival rate to the drought stress (16 survivors from 31 stressed plants), and PpCK-4-overexpression *Arabidopsis* thaliana plants showed a 14% survival rate to the drought stress (1 survivors from 7 stressed plants), as compared to the 11% survival rate that was demonstrated by the untransformed control plants (1 survivor from 9 stressed plants).

Transgenic *Arabidopsis* plants comprising the ScCK-1 gene were screened for their tolerance to drought in three separate experiments. In the first experiment, the plants were subjected to a period of twelve days of drought conditions. After the twelve days, the transgenic plants were screened for their improved drought tolerance. Transgenic plants containing the ScCK-1 transgene (11 plants) retained viability, as shown by their turgid appearance and maintenance of green color, for an average of 2.2 days beyond the untransformed wild type control plant.

In the second experiment, one plant from several independent transgenic lines was used. Three-week-old transgenic plants containing the ScCK-1 transgene were subjected to drought stress conditions. Transgenic plants containing the ScCK-1 transgene (6 plants) retained viability, as shown by their turgid appearance and maintenance of green color, for an average of 0.3 days beyond the untransformed wild type control plant.

In the third experiment, several plants from one independent transgenic line were used. Three-week-old transgenic plants containing the ScCK-1 transgene were subjected to drought stress conditions. The results are shown in Table 14. Transgenic plants containing the ScCK-1 transgene retained a significantly higher photosynthetic yield than the untransformed wild type control plant. For ScCK-1, the average result of 5 replicate plants is listed; for the wild type plants, the average result of 20-25 plants is listed.

TABLE 14

|  | Photosynthetic yield (6 days after final watering) | Photosynthetic yield (10 days after final watering) | Photosynthetic yield (14 days after final watering) |
| --- | --- | --- | --- |
| ScCK-1 | 767 | 780 | 147 |
| Wild type | 757 | 610 | 16 |

Freezing Tolerance Screening of Transformed Plants Comprising *Physcomitrella* Genes. Seedlings were moved to petri dishes containing ½ MS 0.6% agar supplemented with 2% sucrose and 2 µg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C., and decreasing −1° C. each hour. The seedlings were then incubated at −5.0° C. for 24 hours and then allowed to thaw at 5° C. for 12 hours. The water was poured off, and the seedlings were scored after 5 days.

The transgenic plants are screened for their improved cold tolerance, demonstrating that transgene expression confers cold tolerance. Under freezing stress conditions, PpCK-1-overexpressing *Arabidopsis thaliana* plants showed a 100% survival rate to the freeze stress (14 survivors from 14 stressed plants), as compared to the 2% survival rate that was demonstrated by the untransformed control plants (1 survivor from 48 stressed plants).

Salt Tolerance Screening. Seedlings are transferred to filter paper soaked in ½ MS and placed on ½ MS 0.6% agar supplemented with 2 µg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 µg/ml benomyl. The seedlings were scored after 5 days.

Transgenic plants overexpressing the transgene are screened for their improved salt tolerance demonstrating that transgene expression confers salt tolerance. Under freezing stress conditions, PpCK-1-overexpressing *Arabidopsis thaliana* plants showed a 0% survival rate to the freeze stress (0 survivors from 20 stressed plants), PpCK-2-overexpressing *Arabidopsis thaliana* plants showed a 10% survival rate to the freeze stress (1 survivors from 10 stressed plants), and PpCK-4-overexpressing *Arabidopsis thaliana* plants showed a 0% survival rate to the freeze stress (0 survivors from 6 stressed plants), as compared to the 13% survival rate that was demonstrated by the untransformed control plants (3 survivor from 23 stressed plants).

Growth screen under water-limited conditions. The PpCK-1, PpCK-2, PpCK-4, and PpPK-4 genes were overexpressed in *Arabidopsis thaliana* under the control of a constitutive promoter. The transgenic lines were assayed for water use efficiency (WUE), and some of the lines were also assayed for biomass after drought cycling (See Table 15). SC024 represents the empty vector control, and BPS C24 represents the *Arabidopsis* ecotype used for transformation. DW indicates dry weight, and E denotes plant water use. The letters under the Assay column represent independent experiments.

With a constitutive promoter driving expression and for the transgenic lines assayed, EST 289 (PpCK-4) transgenic lines had significant increases in dry weight. EST 142 (PpPK-4) transgenic lines had significant increases in WUE and biomass under drought cycling conditions. For all of the transgenes, the mean versus both of the controls for each parameter was increased, 5-8% for WUE, 11-19% for DW, and 6-9% for E. The variation in phenotype from gene to gene may be explained by variation in the level of transgene expression and the site of transgene insertion.

Table 15

ScCK-1 (ORF 760) was overexpressed in *Arabidopsis thaliana* under the control of a constitutive promoter. The transgenic lines were assayed for dessication tolerance, measuring the average number of days of survival after the wild type control was dead (Table 7).* Please see drawing at FIG. 8.

TABLE 16

| Line | Experiment | Average # days transgenic/WT |
| --- | --- | --- |
| 760-3 | 1 | 0.75 |
|  | 2 | 0.33 |
| 760-4 | 1 | 0.5 |
|  | 2 | 2.2 |
|  | 3 | 1.053 |
| Mean |  | 0.97 |

Example 10

Detection of the Transgenes in the Transgenic *Arabidopsis* Lines

To check for the presence of the transgenes in transgenic *Arabidopsis* lines, PCR was performed on genomic DNA which contaminates the RNA samples taken as exemplified below. Two and one half microliters of the RNA sample was used in a 50 µl PCR reaction using Taq DNA polymerase (Roche Molecular Biochemicals) according to the manufacturer's instructions.

Binary vector plasmid with each gene cloned in was used as positive control, and the wild-type C24 genomic DNA was used as negative control in the PCR reactions. Ten µl of the PCR reaction was analyzed on 0.8% agarose-ethidium bromide gel.

PpCK-1: The primers used in the reactions are:

GCTGACACGCCAAGCCTCGCTAGTC           (SEQ ID NO:38)

GCGTTAACATGCCCATCTTCTCATACTCAGACC   (SEQ ID NO:39)

The PCR program was as following: 30 cycles of 1 minute at 94° C., 1 minute at 62° C. and 4 minutes at 72° C., followed by 10 minutes at 72° C. A 1.7 kb fragment was produced from the positive control and the transgenic plants.

PpCK-2: The primers used in the reactions are:

GCTGACACGCCAAGCCTCGCTAGTC           (SEQ ID NO:40)

GCGTTAACCTTAGGAATCGTATGGCAGAGAGCT   (SEQ ID NO:41)

The PCR program was as following: 30 cycles of 1 minute at 94° C., 1 minute at 62° C. and 4 minutes at 72° C., followed by 10 minutes at 72° C. A 1.9 kb fragment was produced from the positive control and the transgenic plants.

PpPK-4: The primers used in the reactions were:

```
                                    (SEQ ID NO:42)
5'ATCCCGGGAGGCATTGAACTACCTGGAGTGAG3'

(SEQ ID NO:43)
5'GCGATATCGTTGAACTAGTAATCTGTGTTAACTTTATC3'
```

The PCR program was as following: 30 cycles of 1 minute at 94° C., 1 minute at 62° C., and 4 minutes at 72° C., followed by 10 minutes at 72° C. A 1.7 kilobase fragment was produced from the positive control and the transgenic plants.

The transgenes were successfully amplified from the T1 transgenic lines, but not from the wild type C24. This result indicates that the T1 transgenic plants contain at least one copy of the transgenes. There was no indication of existence of either identical or very similar genes in the untransformed *Arabidopsis thaliana* control, which could be amplified by this method from the wild-type plants.

Example 11

Engineering Stress-Tolerant Soybean Plants by Over-Expressing the PpCK-1, PpCK-2, PpCK-4, PpPK-4, ScCK-1, BnCK-1, BnCK-2, BnCK-3, BnCK-4, or BnCK-5 Gene Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate selection agents followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 µM acetosyringone. Bacteria cultures are incubated in this pre-induction medium for 2 hours at room temperature before use. The axis of soybean zygotic seed embryos at approximately 15% moisture content are imbibed for 2 hours at room temperature with the pre-induced *Agrobacterium* suspension culture. The embryos are removed from the imbibition culture and are transferred to Petri dishes containing solid MS medium supplemented with 2% sucrose and incubated for 2 days in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the *Agrobacteria*. The liquid medium is used to moisten the sterile filter paper. The embryos are incubated during 4 weeks at 25° C., under 150 µmol m$^{-2}$sec$^{-1}$ and 12 hours photoperiod. Once the seedlings produce roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 µmol m$^{-2}$sec$^{-1}$ light intensity and 12 hours photoperiod for about 80 days.

The transgenic plants are screened for their improved drought, salt, and/or cold tolerance according to the screening method described in Example 9, demonstrating that transgene expression confers stress tolerance and/or increased water use efficiency.

Example 12

Engineering Stress-Tolerant Rapeseed/Canola Plants by Overexpressing the PpCK-1, PpCK-2, PpCK-4, PpPK-4, ScCK-1, BnCK-1, BnCK-2, BnCK-3, BnCK-4, or BnCK-5 Gene The method of plant transformation described herein is also applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed, and the seeds are air dried overnight in a half-open sterile Petri dish. During this period, the seeds lose approximately 85% of their water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are screened for their improved stress tolerance according to the screening method described in Example 9, demonstrating that transgene expression confers stress tolerance and/or increased water use efficiency.

Example 13

Engineering Stress-Tolerant Corn Plants by over-expressing the PpCK-1, PpCK-2, PpCK-4, PpPK-4, ScCK-1, BnCK-1, BnCK-2, BnCK-3, BnCK-4, or BnCK-5 Gene Transformation of maize (*Zea Mays* L.) with the gene of interest is performed with the method described by Ishida et al., 1996, Nature Biotech. 14745-50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are screened for their improved drought, salt, and/or cold tolerance according to the screening method described in Example 9, demonstrating that transgene expression confers stress tolerance and/or increased water use efficiency.

Example 14

Engineering Stress-Tolerant Wheat Plants by Over-Expressing the PpCK-1, PpCK-2, PpCK-4, PpPK-4, ScCK-1, BnCK-1, BnCK-2, BnCK-3, BnCK-4, or BnCK-5 Gene Transformation of wheat with the gene of interest is performed with the method described by Ishida et al., 1996, Nature Biotech. 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are screened for their improved stress tolerance according to the screening method described in Example 9, demonstrating that transgene expression confers stress tolerance and/or increased water use efficiency.

Example 15

Identification of Homologous and Heterologous Genes

Gene sequences can be used to identify homologous or heterologous genes from cDNA or genomic libraries. Homologous genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by, e.g., UV cross linking. Hybridization is carried out at high stringency conditions. In aqueous solution, hybridization and washing is performed at an ionic strength of 1 M NaCl and a temperature of 68° C. Hybridization probes are generated by, e.g., radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10-20 amino acids) can be carried out by using synthetic radio labeled oligonucleotide probes. Radiolabeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are then radiolabeled by, for example, nick transcription. Hybridization is normally performed at low stringency conditions using high oligonucleotide concentrations.

Oligonucleotide Hybridization Solution:
6×SSC
0.01 M sodium phosphate
1 mM EDTA (pH 8)
0.5% SDS
100 μg/ml denatured salmon sperm DNA
0.1% nonfat dried milk During hybridization, the temperature is lowered stepwise to 5-10° C. below the estimated oligonucleotide $T_m$, or down to room temperature, followed by washing steps and autoradiography. Washing is performed with low stringency, such as 3 washing steps using 4×SSC. Further details are described by Sambrook, J. et al., 1989, "Molecular Cloning: A Laboratory Manual," Cold Spring Harbor Laboratory Press or Ausubel, F. M. et al., 1994, "Current Protocols in Molecular Biology", John Wiley & Sons.

Example 16

Identification of Homologous Genes by Screening Expression Libraries with Antibodies c-DNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994, BioTechniques 17:257-262. The antibody can be used to screen expression cDNA libraries to identify homologous or heterologous genes via an immunological screening (Sambrook, J. et al., 1989, "Molecular Cloning: A Laboratory Manual", Cold Spring Harbor Laboratory Press or Ausubel, F. M. et al., 1994, "Current Protocols in Molecular Biology", John Wiley & Sons).

Example 17

In vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*), which are impaired in their capabilities to maintain the integrity of their genetic information. Typical mutator strains have mutations in the genes for the DNA repair system (e.g., mutHLS, mutD, mutT, etc.; for reference, see Rupp, W. D., 1996, DNA repair mechanisms, in: *Escherichia coli* and *Salmonella*, p. 2277-2294, ASM: Washington.) Such strains are well known to those skilled in the art. The use of such strains is illustrated, for example, in Greener, A. and Callahan, M., 1994, Strategies 7:32-34. Transfer of mutated DNA molecules into plants is preferably done after selection and testing in microorganisms. Transgenic plants are generated according to various examples within the exemplification of this document.

Example 18

In Vitro Analysis of the Function of *Physcomitrella* Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications, and examples for the determination of many enzyme activities may be found, for example, in the following references: Dixon, M., and Webb, E. C., 1979, Enzymes. Longmans: London; Fersht, 1985, Enzyme Structure and Mechanism. Freeman: New York; Walsh, 1979, Enzymatic Reaction Mechanisms. Freeman: San Francisco; Price, N. C., Stevens, L., 1982, Fundamentals of Enzymology. Oxford Univ. Press: Oxford; Boyer, P. D., ed., 1983, The Enzymes, 3rd ed. Academic Press: New York; Bisswanger, H., 1994, Enzymkinetik, $2^{nd}$ ed. VCH: Weinheim (ISBN 3527300325); Bergmeyer, H. U., Bergmeyer, J., Graβl, M., eds., 1983-1986, Methods of Enzymatic Analysis, $3^{rd}$ ed., vol. I-XII, Verlag Chemie: Weinheim; and Ullmann's Encyclopedia of Industrial Chemistry, 1987, vol. A9, Enzymes. VCH: Weinheim, p. 352-363.

The activity of proteins, which bind to DNA, can be measured by several well-established methods, such as DNA band-shift assays (also called gel retardation assays). The effect of such proteins on the expression of other molecules can be measured using reporter gene assays (such as that described in Kolmar, H. et al., 1995, EMBO J. 14: 3895-3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B., 1989, Pores, Channels and Transporters, in Biomembranes, Molecular Structure and Function, pp. 85-137, 199-234 and 270-322, Springer: Heidelberg.

Example 19

Purification of the Desired Product from Transformed Organisms

Recovery of the desired product from plant material (i.e., *Physcomitrella patens* or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, the cells can be harvested from the culture by low-speed centrifugation, and the cells can be lysed by standard techniques, such as mechanical force or sonification. Organs of plants can be separated mechanically from other tissue or organs. Following homogenization, cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin, while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, 1986, D.F. Biochemical Engineering Fundamentals, McGraw-Hill: New York. Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994, Appl. Environ. Microbiol. 60:133-140; Malakhova et al., 1996, Biotekhnologiya 11:27-32; and Schmidt et al., 1998, Bioprocess Engineer. 19:67-70; Ulmann's Encyclopedia of Industrial Chemistry, 1996, vol. A27, VCH: Weinheim, p. 89-90, p. 521-540, p. 540-547, p. 559-566, 575-581, and p. 581-587; Michal, G., 1999, Biochemical Pathways: An Atlas of Biochemistry and Molecular Biology, John Wiley and Sons; Fallon, A. et al., 1987, Applications of HPLC in Biochemistry in: Laboratory Techniques in Biochemistry and Molecular Biology, vol. 17.

The invention claimed is:

1. An isolated polynucleotide selected from the group consisting of:
   a) a polynucleotide having a sequence as set forth in nucleotides 1 to 2276 of SEQ ID NO:19; and
   b) a polynucleotide encoding a polypeptide having a sequence as set forth in amino acids 1 to 526 of SEQ ID NO:20.

2. The isolated polynucleotide of claim 1, having the sequence as set forth in nucleotides 1 to 2276 of SEQ ID NO:19.

3. The isolated polynucleotide of claim 1, encoding the polypeptide having the sequence as set forth in amino acids 1 to 526 of SEQ ID NO:20.

4. A vector comprising an isolated polynucleotide selected from the group consisting of:
   a) a polynucleotide having a sequence as set forth in nucleotides 1 to 2276 of SEQ ID NO:19; and
   b) a polynucleotide encoding a polypeptide having a sequence as set forth in amino acids 1 to 526 of SEQ ID NO:20.

5. The vector of claim 4, wherein the isolated polynucleotide has the sequence as set forth in nucleotides 1 to 2276 of SEQ ID NO:19.

6. The vector of claim 4, wherein the isolated polynucleotide encodes the polypeptide having the sequence as set forth in amino acids 1 to 526 of SEQ ID NO:20.

7. A transgenic plant cell transformed with an isolated polynucleotide selected from the group consisting of:
   a) a polynucleotide having a sequence as set forth in nucleotides 1 to 2276 of SEQ ID NO:19; and
   b) a polynucleotide encoding a polypeptide having a sequence as set forth in amino acids 1 to 526 of SEQ ID NO:20.

8. The transgenic plant cell of claim 7, wherein the isolated polynucleotide has the sequence as set forth in nucleotides 1 to 2276 of SEQ ID NO:19.

9. The transgenic plant cell of claim 7, wherein the isolated polynucleotide encodes the polypeptide having the sequence as set forth in amino acids 1 to 526 of SEQ ID NO:20.

10. A transgenic plant transformed with an isolated polynucleotide selected from the group consisting of:
    a) a polynucleotide having a sequence as set forth in nucleotides 1 to 2276 of SEQ ID NO:19; and
    b) a polynucleotide encoding a polypeptide having a sequence as set forth in amino acids 1 to 526 of SEQ ID NO:20.

11. The transgenic plant of claim 10, wherein the isolated polynucleotide has the sequence as set forth in nucleotides 1 to 2276 of SEQ ID NO:19.

12. The transgenic plant of claim 10, wherein the isolated polynucleotide encodes the polypeptide having the sequence as set forth in amino acids 1 to 526 of SEQ ID NO:20.

13. The transgenic plant of claim 10, wherein the plant is a monocot.

14. The transgenic plant of claim 10, wherein the plant is a dicot.

15. The transgenic plant of claim 10, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and a forage crop.

16. The transgenic plant of claim 10, wherein the plant is maize.

17. The transgenic plant of claim 10, wherein the plant is soybean.

18. The transgenic plant of claim 10, wherein the plant is rapeseed or canola.

19. The transgenic plant of claim 10, wherein the plant is cotton.

20. A transgenic plant seed which is true breeding for a transgene comprising a polynucleotide selected from the group consisting of:

a) a polynucleotide having a sequence as set forth in nucleotides 1 to 2276 of SEQ ID NO:19; and b) a polynucleotide encoding a polypeptide having a sequence as set forth in amino acids 1 to 526 of SEQ ID NO:20.

21. The transgenic plant seed of claim 20, wherein the polynucleotide has the sequence as set forth in nucleotides 1 to 2276 of SEQ ID NO:19.

22. The transgenic plant seed of claim 20, wherein the polynucleotide encodes the polypeptide having the sequence as set forth in amino acids 1 to 526 of SEQ ID NO:20.

* * * * *

```
                        SEQUENCE LISTING

<160> NUMBER OF SEQ ID NOS: 53

<210> SEQ ID NO 1
<211> LENGTH: 1942
<212> TYPE: DNA
<213> ORGANISM: Physcomitrella patens

<400> SEQUENCE: 1
atcccgggcg cagcatgtga ctcgtcacct gcagtttatt gaagaagaaa tccgtacaga      60
ataaaaggaa tacaacggcg tcgtcttcga tggaaccccg cgtcggcaac aagtatcgcc     120
ttggccggaa aattgggagt ggttcctttg gtgagatcta cctggggacc aatctcgtga     180
```

-continued

```
ctcatgagga ggtcggcatc aagctggaga gcatcaaggc caagcatcca caattgcttt    240
atgagtccaa gttgtaccgt attcttcaag gaggaactgg gattcccaac atcagatggt    300
acggaattga aggagactat aatgtgatgg ttcttgatct tctgggaccc agtcttgaag    360
atcttttcaa tttctgcagc cggaaattct ctttgaagac agttctcatg cttgccgacc    420
agctgatcaa tcgagtggag tatgtgcatg ccaagagttt cctccacagg gacataaagc    480
ctgacaattt cttgatgggg ctaggcaggc gagcaaatca ggtctatatg attgactttg    540
gtcttgcaaa gaagtatcgc gatcccacta ctcatcagca cattccttat agagagaaca    600
aaaatcttac tggaaccgct cgatatgcaa gtatcaacac tcatcttggt attgaacaaa    660
gcaggagaga tgatctggag tctcttggat atgttctcat gtatttcttg agaggcagcc    720
tgccttggca aggaatgaaa gcaggaacca agaagcagaa gtatgaaaaa atcagtgaga    780
aaaagatgtc caccctata gagttccttt gtaaagctta cccgtctgag tttgcttcat    840
acttccacta ctgtcggtct cttcggttcg atgacaaacc ggactatgct tacctgaaga    900
gaattttccg agatctcttc attcgtgagg gttttcagtt tgattatgtt ttcgactgga    960
cgattttgaa gtatcagcaa acacattttt ctggtggtcc tctccgtcca gcggctgcgg   1020
cgggaggttc aagtggagca gcagcagcag cggcagcagg aattggtaca gtcccaagag   1080
acgcccagcg agcaattgag cctactgatg ttgccgctcg aactcgaatg gttggtgcga   1140
ctcgctctag tggattaaat ccactggacg cgtcaaagca taagagtact agcccagatg   1200
aagccgcttc taaggacata gcccttagcg gtcttgcaga accagagcgc acgcatgctt   1260
cttcgtttgt gcgggggagc tcatcatcaa ggagagctgt tgttggatgt gctaggccag   1320
cagggtcaac agaggcggga gatggaacgc gggtgttggc tggcaaaatg ggccccacta   1380
gcctgcgcac atcagcagga atgcagagga gctctccggt ggcatctacg gatcccaagc   1440
ggacgggacg agattcttat gctggaaact ccggaagaaa tcctagttcc tctcgaaatt   1500
cgaaagagtg agcacattgg ttgaactggg tcctgcatct tgttcgaaga gcattacaac   1560
tgtatctggc cttggtatct gctgtggttt aggaatttgg ccttgtactt gatttgaaga   1620
acaggttcgt aagaaattga tcaaatttca atgtcgtggg cgtccagttc aggatatggt   1680
tggtggcttg tgatggatat attatctgtt tctatctttg aaggtgttgc ccccagccgt   1740
atagttttca tctttcatag cttgtagttg gcaaagccca ttgccatctg tcaatattca   1800
gagtgtggtt gagggagctg tttagccttc tagataagag atctggattg cgttctggat   1860
tgctgcacag accttgaaga tttgtggctg ttcgagatta tgaaatgaac agcttcctag   1920
agcaagtagt agctgttaac gc                                            1942
```

<210> SEQ ID NO 2
<211> LENGTH: 473
<212> TYPE: PRT
<213> ORGANISM: Physcomitrella patens

<400> SEQUENCE: 2

```
Met Glu Pro Arg Val Gly Asn Lys Tyr Arg Leu Gly Arg Lys Ile Gly
  1               5                  10                  15

Ser Gly Ser Phe Gly Glu Ile Tyr Leu Gly Thr Asn Leu Val Thr His
             20                  25                  30

Glu Glu Val Gly Ile Lys Leu Glu Ser Ile Lys Ala Lys His Pro Gln
         35                  40                  45

Leu Leu Tyr Glu Ser Lys Leu Tyr Arg Ile Leu Gln Gly Gly Thr Gly
     50                  55                  60
```

-continued

```
Ile Pro Asn Ile Arg Trp Tyr Gly Ile Glu Gly Asp Tyr Asn Val Met
 65                  70                  75                  80

Val Leu Asp Leu Leu Gly Pro Ser Leu Glu Asp Leu Phe Asn Phe Cys
                 85                  90                  95

Ser Arg Lys Phe Ser Leu Lys Thr Val Leu Met Leu Ala Asp Gln Leu
            100                 105                 110

Ile Asn Arg Val Glu Tyr Val His Ala Lys Ser Phe Leu His Arg Asp
        115                 120                 125

Ile Lys Pro Asp Asn Phe Leu Met Gly Leu Gly Arg Arg Ala Asn Gln
    130                 135                 140

Val Tyr Met Ile Asp Phe Gly Leu Ala Lys Lys Tyr Arg Asp Pro Thr
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Leu Arg
        195                 200                 205

Gly Ser Leu Pro Trp Gln Gly Met Lys Ala Gly Thr Lys Lys Gln Lys
    210                 215                 220

Tyr Glu Lys Ile Ser Glu Lys Lys Met Ser Thr Pro Ile Glu Phe Leu
225                 230                 235                 240

Cys Lys Ala Tyr Pro Ser Glu Phe Ala Ser Tyr Phe His Tyr Cys Arg
                245                 250                 255

Ser Leu Arg Phe Asp Asp Lys Pro Asp Tyr Ala Tyr Leu Lys Arg Ile
            260                 265                 270

Phe Arg Asp Leu Phe Ile Arg Glu Gly Phe Gln Phe Asp Tyr Val Phe
        275                 280                 285

Asp Trp Thr Ile Leu Lys Tyr Gln Gln Thr His Phe Ser Gly Gly Pro
    290                 295                 300

Leu Arg Pro Ala Ala Ala Gly Gly Ser Gly Ala Ala Ala Ala
305                 310                 315                 320

Ala Ala Ala Gly Ile Gly Thr Val Pro Arg Asp Ala Gln Arg Ala Ile
                325                 330                 335

Glu Pro Thr Asp Val Ala Ala Arg Thr Arg Met Val Gly Ala Thr Arg
            340                 345                 350

Ser Ser Gly Leu Asn Pro Leu Asp Ala Ser Lys His Lys Ser Thr Ser
        355                 360                 365

Pro Asp Glu Ala Ala Ser Lys Asp Ile Ala Leu Ser Gly Leu Ala Glu
    370                 375                 380

Pro Glu Arg Thr His Ala Ser Ser Phe Val Arg Gly Ser Ser Ser Ser
385                 390                 395                 400

Arg Arg Ala Val Val Gly Cys Ala Arg Pro Ala Gly Ser Thr Glu Ala
                405                 410                 415

Gly Asp Gly Thr Arg Val Leu Ala Gly Lys Met Gly Pro Thr Ser Leu
            420                 425                 430

Arg Thr Ser Ala Gly Met Gln Arg Ser Ser Pro Val Ala Ser Thr Asp
        435                 440                 445

Pro Lys Arg Thr Gly Arg Asp Ser Tyr Ala Gly Asn Ser Gly Arg Asn
    450                 455                 460

Pro Ser Ser Ser Arg Asn Ser Lys Glu
465                 470
```

<210> SEQ ID NO 3
<211> LENGTH: 1736
<212> TYPE: DNA
<213> ORGANISM: Physcomitrella patens

<400> SEQUENCE: 3

```
atcccgggct cacgtagtgc actgaactct gtctgaattt tagggatga gaggtagatt    60
tgaagaatac tggtgtctaa ttttctgtta attttcacc cttgaggtag ctcatggatt   120
tgggaggtga tcgcatgaga gctcctcaga ggcagtctcg agaatatcaa tatagatcat   180
tggacgtctt cacagagcag cacgagcagt tgcaaaagca gcagcagcaa gatgagtatc   240
agagaacaga attgaagctc gagacactgc caaaaatgtt aagcaatgcg accgtgtcat   300
cttcccctcg aagcagtccg gatggacgta gactacgtac agtcgcgaat aagtatgctg   360
tggaaggtat ggttgggagt ggcgcattct gcaaggtgta tcagggctcc gatttgacga   420
accacgaggt tgtgggcatc aagctggagg atacgagaac tgagcacgct cagttaatgc   480
acgagtcgcg cttgtacaac atattgcggg gtgggaaggg agtgcccaac atgagatggt   540
tcggaaaaga gcaagactac aatgtgatgg tgctagacct attggggccg aacctgttgc   600
acctctttaa ggtgtgtggg ctaaggtttt cgttgaagac cgtgattatg ctcggttacc   660
aaatgattga ccgggtggaa tacgtgcatt ctcgagggc cgttcaccgt gacctgaagc   720
cggataactt cctcatgggc tgcggtcggc aaggaaacca agtgttcatt atagattttg   780
gcttggcaaa ggagtacatg gacccggcaa cacgaaggca tatcccttac cgagatagga   840
agagcttcac agggacggca cggtacgcta gtaggaatca gcacagagga atcgagcaca   900
gtagaagaga tgacatagaa tcacttggtt acattcttat gtactttcta agaggcaatt   960
tgccatggca agggaagggc gggcaacgcc tcactgacca gaagcaacac gagtacatgc  1020
acaacaaaat caagatgaac accactgtgg aggagctttg tgatgggtat cccagtcaat  1080
ttgccgactt tttgcaccac gcgcgaagtc taggtttcta cgagcagcct gactactgtt  1140
acctccgaag cttgttccgt gatcttttca ttcagaaaaa attccagctc gaccatgtgt  1200
acgactggac tgtgtatact caactccccc agaatggctc tctgcaatca gtgcgcagcc  1260
agaattccgc tgcttcgtcc catttgcaaa atcgaccttc gaatgtatca tattgtccac  1320
ccttgaccaa gtcggagttc cgtcgtgagg ttgttgcggc gaattagggc ttacgttggg  1380
aggactagtg gttcatcctc tgctctggta ctaaaatagc acaaggttgc ttactgtttc  1440
cctctctcaa gtcttacatg attgtgaatg ggggtttatg gagttgagga tgaggcaact  1500
aagcagagtg taggaaaaga gttgtagact ctctagtgtg tagtgtgtaa atcaaggctt  1560
ctagcattgt gtcggtagct tgtatggatc agactagaaa tgactttatc cattacaaga  1620
atttttactc ggaaagccca tgacggtgat gatttcaata cgttgcacaa gcaactttct  1680
tctgtaattg aaatagagga tctggtctga gtatgagaag atgggcatgt taacgc      1736
```

<210> SEQ ID NO 4
<211> LENGTH: 417
<212> TYPE: PRT
<213> ORGANISM: Physcomitrella patens

<400> SEQUENCE: 4

Met Asp Leu Gly Gly Asp Arg Met Arg Ala Pro Gln Arg Gln Ser Arg
1               5                   10                  15

Glu Tyr Gln Tyr Arg Ser Leu Asp Val Phe Thr Glu Gln His Glu Gln
            20                  25                  30

```
Leu Gln Lys Gln Gln Gln Asp Glu Tyr Gln Arg Thr Glu Leu Lys
        35                  40                  45

Leu Glu Thr Leu Pro Lys Met Leu Ser Asn Ala Thr Val Ser Ser Ser
 50                  55                  60

Pro Arg Ser Ser Pro Asp Gly Arg Arg Leu Arg Thr Val Ala Asn Lys
 65                  70                  75                  80

Tyr Ala Val Glu Gly Met Val Gly Ser Gly Ala Phe Cys Lys Val Tyr
                 85                  90                  95

Gln Gly Ser Asp Leu Thr Asn His Glu Val Val Gly Ile Lys Leu Glu
            100                 105                 110

Asp Thr Arg Thr Glu His Ala Gln Leu Met His Glu Ser Arg Leu Tyr
            115                 120                 125

Asn Ile Leu Arg Gly Gly Lys Gly Val Pro Asn Met Arg Trp Phe Gly
130                 135                 140

Lys Glu Gln Asp Tyr Asn Val Met Val Leu Asp Leu Leu Gly Pro Asn
145                 150                 155                 160

Leu Leu His Leu Phe Lys Val Cys Gly Leu Arg Phe Ser Leu Lys Thr
                165                 170                 175

Val Ile Met Leu Gly Tyr Gln Met Ile Asp Arg Val Glu Tyr Val His
                180                 185                 190

Ser Arg Gly Leu Val His Arg Asp Leu Lys Pro Asp Asn Phe Leu Met
            195                 200                 205

Gly Cys Gly Arg Gln Gly Asn Gln Val Phe Ile Ile Asp Phe Gly Leu
            210                 215                 220

Ala Lys Glu Tyr Met Asp Pro Ala Thr Arg Arg His Ile Pro Tyr Arg
225                 230                 235                 240

Asp Arg Lys Ser Phe Thr Gly Thr Ala Arg Tyr Ala Ser Arg Asn Gln
                245                 250                 255

His Arg Gly Ile Glu His Ser Arg Arg Asp Asp Ile Glu Ser Leu Gly
            260                 265                 270

Tyr Ile Leu Met Tyr Phe Leu Arg Gly Asn Leu Pro Trp Gln Gly Lys
            275                 280                 285

Gly Gly Gln Arg Leu Thr Asp Gln Lys Gln His Glu Tyr Met His Asn
            290                 295                 300

Lys Ile Lys Met Asn Thr Val Glu Glu Leu Cys Asp Gly Tyr Pro
305                 310                 315                 320

Ser Gln Phe Ala Asp Phe Leu His His Ala Arg Ser Leu Gly Phe Tyr
                325                 330                 335

Glu Gln Pro Asp Tyr Cys Tyr Leu Arg Ser Leu Phe Arg Asp Leu Phe
            340                 345                 350

Ile Gln Lys Lys Phe Gln Leu Asp His Val Tyr Asp Trp Thr Val Tyr
            355                 360                 365

Thr Gln Leu Pro Gln Asn Gly Ser Leu Gln Ser Val Arg Ser Gln Asn
370                 375                 380

Ser Ala Ala Ser Ser His Leu Gln Asn Arg Pro Ser Asn Val Ser Tyr
385                 390                 395                 400

Cys Pro Pro Leu Thr Lys Ser Glu Phe Arg Arg Glu Val Val Ala Ala
                405                 410                 415

Asn

<210> SEQ ID NO 5
<211> LENGTH: 1900
<212> TYPE: DNA
```

<210> ORGANISM: Physcomitrella patens

<400> SEQUENCE: 5

```
atcccgggtt gtcgaggacg gagagagaag agagagagag agagagagag aggtgttgtt      60
tagggggaggc atgcgggagc aggattggtg ttaagttcgt aaggagaagg gagtacatgc    120
aagtgcgtgc ttgtcggata tcggacagct ggatttgtaa ataagcggag aggagggtcg    180
gtaatcaggg gcgtacatcg atggagccgc gtgtgggaaa caagtatcgg ctgggacgga    240
aaattgggag cggttccttt ggggagatct atcttgggac caatgttcag accaatgagg    300
aggtcggaat aaagctggaa agcatcaaga cgaagcatcc acaattgctg tacgagtcca    360
agctctaccg gatactacaa ggaggaactg ggattcccaa tatcagatgg ttcgggatag    420
aaggagacta caatgtcttg gttctggatc tgttggggcc aagtctcgaa gacctttca    480
acttctgcag ccggaagttc tctttaaaga ctgttctcat gcttgctgac agctgatca    540
acagagtgga gtatgtgcat gcgaaaagct tccttcatag acatcaag cctgataatt    600
ttctaatggg gcttggtagg cgagcaaacc aggtctacat tattgatttt ggtcttgcca    660
agaagtaccg cgacccttcc acgcatcagc atattcccta cagggagaac aaaatctga    720
cagggactgc tcggtatgca agcatcaaca ctcatcttgg tattgagcaa agcagacgag    780
atgatttgga atctcttgga tatgtgctca tgtacttcct gagaggcagt cttccatggc    840
aaggactgaa agcgggaacc aagaagcaga agtacgagaa gatcagtgag aaaaaaatgt    900
ccacgcccat tgaggtcctt tgtaaaaatt atccttcaga attcgcctcg tacttccact    960
actgccggtc cttgcgtttt gatgacaaac ccgactatgc atatttgaaa agaatcttcc   1020
gtgacctctt tattcgtgag ggtttttcaat ttgactacg ttttgactgg acaattctga   1080
agtaccagca gtcacaaatt tccggtggca gttcaactcg actgggtgct tctgcagggc   1140
aaaccagtgg tgcacttgga actggggcta caggaagccg agacctgcag cggcccaccg   1200
aaccaatgga tccttctcgg cgcaggcttc ctggaggagc aaatggctcc ggggtcgcaa   1260
atgctttgga ctcatctaag cacaaaagtc ctggacttga tgaatctgct aaggattctg   1320
ctcttgctgt tgtgtcagaa ccagagcgca tgcatacatc ttcgtatgca actcggggg   1380
gttcttcctc caggcgagct gtcctatcta gcagcaggcc ctcagggca tcagcagaag   1440
tcgtagattc ctctcgaaca gggagcagta agcttggtcc caccagctta cggtcgtcag   1500
cagggatgca gaggagctct ccagttactt cggacccaaa gcggatatct agccgccatc   1560
cacaaccgcc atctgccaac ttgaggattt acgaagccgc tatcaaggga ttgaatcac   1620
tttctgttga ggtggatcaa agccgttata agtaggccca ggcttgtggt tatatagccg   1680
ggctctgtct tctatcaaac cctcttgtta tgtagatgag agttgctcta catttggcaa   1740
cagcctgatt gagggaaaa cggtggttct gtcctacaat ggtgctaaga ctacaggtct   1800
ctcatactta ggaatgaatg gatctctatc ttgttaccat caaaccattg tcagtgcttt   1860
gtgtggtagc tctctgccat acgattccta aggttaacgc                          1900
```

<210> SEQ ID NO 6
<211> LENGTH: 484
<212> TYPE: PRT
<213> ORGANISM: Physcomitrella patens

<400> SEQUENCE: 6

```
Met Glu Pro Arg Val Gly Asn Lys Tyr Arg Leu Gly Arg Lys Ile Gly
  1               5                  10                  15
```

```
Ser Gly Ser Phe Gly Glu Ile Tyr Leu Gly Thr Asn Val Gln Thr Asn
            20                  25                  30
Glu Glu Val Gly Ile Lys Leu Glu Ser Ile Lys Thr Lys His Pro Gln
        35                  40                  45
Leu Leu Tyr Glu Ser Lys Leu Tyr Arg Ile Leu Gln Gly Gly Thr Gly
    50                  55                  60
Ile Pro Asn Ile Arg Trp Phe Gly Ile Glu Gly Asp Tyr Asn Val Leu
65                  70                  75                  80
Val Leu Asp Leu Leu Gly Pro Ser Leu Glu Asp Leu Phe Asn Phe Cys
                85                  90                  95
Ser Arg Lys Phe Ser Leu Lys Thr Val Leu Met Leu Ala Asp Gln Leu
            100                 105                 110
Ile Asn Arg Val Glu Tyr Val His Ala Lys Ser Phe Leu His Arg Asp
        115                 120                 125
Ile Lys Pro Asp Asn Phe Leu Met Gly Leu Gly Arg Arg Ala Asn Gln
    130                 135                 140
Val Tyr Ile Ile Asp Phe Gly Leu Ala Lys Lys Tyr Arg Asp Pro Ser
145                 150                 155                 160
Thr His Gln His Ile Pro Tyr Arg Glu Asn Lys Asn Leu Thr Gly Thr
                165                 170                 175
Ala Arg Tyr Ala Ser Ile Asn Thr His Leu Gly Ile Glu Gln Ser Arg
            180                 185                 190
Arg Asp Asp Leu Glu Ser Leu Gly Tyr Val Leu Met Tyr Phe Leu Arg
        195                 200                 205
Gly Ser Leu Pro Trp Gln Gly Leu Lys Ala Gly Thr Lys Lys Gln Lys
    210                 215                 220
Tyr Glu Lys Ile Ser Glu Lys Lys Met Ser Thr Pro Ile Glu Val Leu
225                 230                 235                 240
Cys Lys Asn Tyr Pro Ser Glu Phe Ala Ser Tyr Phe His Tyr Cys Arg
                245                 250                 255
Ser Leu Arg Phe Asp Asp Lys Pro Asp Tyr Ala Tyr Leu Lys Arg Ile
            260                 265                 270
Phe Arg Asp Leu Phe Ile Arg Glu Gly Phe Gln Phe Asp Tyr Val Phe
        275                 280                 285
Asp Trp Thr Ile Leu Lys Tyr Gln Gln Ser Gln Ile Ser Gly Gly Ser
    290                 295                 300
Ser Thr Arg Leu Gly Ala Ser Ala Gly Gln Thr Ser Gly Ala Leu Gly
305                 310                 315                 320
Thr Gly Ala Thr Gly Ser Arg Asp Leu Gln Arg Pro Thr Glu Pro Met
                325                 330                 335
Asp Pro Ser Arg Arg Arg Leu Pro Gly Gly Ala Asn Gly Ser Gly Val
            340                 345                 350
Ala Asn Ala Leu Asp Ser Ser Lys His Lys Ser Pro Gly Leu Asp Glu
        355                 360                 365
Ser Ala Lys Asp Ser Ala Leu Ala Val Val Ser Glu Pro Glu Arg Met
    370                 375                 380
His Thr Ser Ser Tyr Ala Thr Arg Gly Gly Ser Ser Arg Arg Ala
385                 390                 395                 400
Val Leu Ser Ser Arg Pro Ser Gly Ala Ser Ala Glu Val Val Asp
                405                 410                 415
Ser Ser Arg Thr Gly Ser Ser Lys Leu Gly Pro Thr Ser Leu Arg Ser
            420                 425                 430
Ser Ala Gly Met Gln Arg Ser Ser Pro Val Thr Ser Asp Pro Lys Arg
```

435                 440                    445
Ile Ser Ser Arg His Pro Gln Pro Pro Ser Ala Asn Leu Arg Ile Tyr
    450                 455                 460

Glu Ala Ala Ile Lys Gly Val Glu Ser Leu Ser Val Glu Val Asp Gln
465                 470                 475                 480

Ser Arg Tyr Lys

<210> SEQ ID NO 7
<211> LENGTH: 1795
<212> TYPE: DNA
<213> ORGANISM: Physcomitrella patens

<400> SEQUENCE: 7

| | | | | |
|---|---|---|---|---|
| gcccttatcc | cgggaggcat | tgaactacct | ggagtgagat | ttttttggga atttgaaaga | 60 |
| gaattacata | tatacaaggt | tgaggctcac | cgagaacaag | tctgctgata gcttcttcac | 120 |
| tcttgaaata | gatagttcat | catggattca | ggaggtgacc | gcgtgcgagc tcctcagaag | 180 |
| cagtctcgcg | aggaggatca | gtaccgttca | ttgaacattg | ctacagagca tcgtcagcat | 240 |
| atacagaagc | accaacaaca | ccaacagcag | ccggggactg | gattggttgt tgaaacgctt | 300 |
| caaaaacac | tatgtaacgt | gactgtgacc | tcacctacaa | gcagtccgga gggggtaga | 360 |
| ttacgtactg | ttgcgaacaa | gtatgcagtg | aaggaatgg | tcggcagtgg cgcattttgc | 420 |
| aaggtgtacc | agggttctga | cttaaccaac | catgaggttg | tgggcatcaa gctcgaggat | 480 |
| acaagaacag | agcacgcaca | attgatgcac | gagtcgcgat | tatacaacat tttgcggggt | 540 |
| ggaaagggag | tgcccaacat | gagatggttt | gggaagagc | aagactacaa tgtgatggtg | 600 |
| ctagatttgc | tggggcctaa | cctactgcac | cttttcaagg | tgtgtgggca agattttcg | 660 |
| ttgaagacgg | tgatcatgtt | ggggtaccaa | atgatcgacc | gggtggagta cgtgcactcg | 720 |
| cgaggtctag | ttcatcgtga | cttgaaacca | gataatttcc | tcatgggctg cggccggcaa | 780 |
| gggaaccaag | tgttcattat | tgactttggc | ttggcaaaag | agtacatcga ccccgcgaca | 840 |
| cgtagacaca | ttccttaccg | agatagaaag | agctttacag | aacagcgcg gtatgctagt | 900 |
| aggaatcagc | acaaaggaat | cgaacacagc | aggagagatg | acatagaatc acttggttac | 960 |
| attcttatgt | actttcttag | ggggaattta | ccatggcaag | gtcaaggggg gcaacgtttc | 1020 |
| accgatcaga | agcaacatga | gtacatgcac | aacaaaatta | gatggagac taccatcgag | 1080 |
| gatctctgcg | atgggtaccc | cagacaattt | gccgactttt | tacaccacgc gcgcgagttg | 1140 |
| ggattctatg | agcagcctga | ctactcgtac | cttcgcagcc | tgttccgtga tcttttcatt | 1200 |
| cagaagaaat | tccagcttga | ccatgtctac | gactggacag | tgtacactca acctcctcag | 1260 |
| aatggctctg | cacaaacagt | tcgaagcccg | gctgccggtc | cacagactca cttacaaagt | 1320 |
| cgcccttcca | atgtatcata | ttgtccacct | ctgactaaac | cagagttccg gcgtgaggta | 1380 |
| gttgcggcga | attagggttt | acacaggaag | agatgtggta | aagcatctca tcttcttcgt | 1440 |
| tctggtgcca | aaatggtaca | aggtcgtctg | ctgtctcttt | tcgcaagcc ctcacatata | 1500 |
| gatgaaggtt | tgtgaagtta | gagatgcaac | taccaagcaa | aggctaggaa aagagctgta | 1560 |
| gactttctag | tgtgtagtgt | gtaaatcaag | gcttctggca | tggtatcggc agtcaggtgc | 1620 |
| atggagcaga | atagaaatta | cttcgtgcat | gacaagattt | tttttcttgc agagctctcg | 1680 |
| acggttctgc | gatctcactt | ctctacacaa | ccagcgctcc | tttaattgaa agaggatct | 1740 |
| ggtacgagta | tgataaagtt | aacacagatt | actagttcaa | cgatatcgca aggc | 1795 |

<210> SEQ ID NO 8
<211> LENGTH: 417
<212> TYPE: PRT
<213> ORGANISM: Physcomitrella patens

<400> SEQUENCE: 8

```
Met Asp Ser Gly Gly Asp Arg Val Arg Ala Pro Gln Lys Gln Ser Arg
  1               5                  10                  15

Glu Glu Asp Gln Tyr Arg Ser Leu Asn Ile Ala Thr Glu His Arg Gln
             20                  25                  30

His Ile Gln Lys His Gln His Gln Gln Pro Gly Thr Gly Leu
         35                  40                  45

Val Val Glu Thr Leu Gln Lys Thr Leu Cys Asn Val Thr Val Ser
     50                  55                  60

Pro Thr Ser Ser Pro Glu Gly Gly Arg Leu Arg Thr Val Ala Asn Lys
 65                  70                  75                  80

Tyr Ala Val Glu Gly Met Val Gly Ser Gly Ala Phe Cys Lys Val Tyr
                 85                  90                  95

Gln Gly Ser Asp Leu Thr Asn His Glu Val Val Gly Ile Lys Leu Glu
            100                 105                 110

Asp Thr Arg Thr Glu His Ala Gln Leu Met His Glu Ser Arg Leu Tyr
        115                 120                 125

Asn Ile Leu Arg Gly Gly Lys Gly Val Pro Asn Met Arg Trp Phe Gly
    130                 135                 140

Lys Glu Gln Asp Tyr Asn Val Met Val Leu Asp Leu Leu Gly Pro Asn
145                 150                 155                 160

Leu Leu His Leu Phe Lys Val Cys Gly Gln Arg Phe Ser Leu Lys Thr
                165                 170                 175

Val Ile Met Leu Gly Tyr Gln Met Ile Asp Arg Val Glu Tyr Val His
            180                 185                 190

Ser Arg Gly Leu Val His Arg Asp Leu Lys Pro Asp Asn Phe Leu Met
        195                 200                 205

Gly Cys Gly Arg Gln Gly Asn Gln Val Phe Ile Ile Asp Phe Gly Leu
    210                 215                 220

Ala Lys Glu Tyr Ile Asp Pro Ala Thr Arg Arg His Ile Pro Tyr Arg
225                 230                 235                 240

Asp Arg Lys Ser Phe Thr Gly Thr Ala Arg Tyr Ala Ser Arg Asn Gln
                245                 250                 255

His Lys Gly Ile Glu His Ser Arg Arg Asp Ile Glu Ser Leu Gly
            260                 265                 270

Tyr Ile Leu Met Tyr Phe Leu Arg Gly Asn Leu Pro Trp Gln Gly Gln
        275                 280                 285

Gly Gly Gln Arg Phe Thr Asp Gln Lys Gln His Glu Tyr Met His Asn
    290                 295                 300

Lys Ile Lys Met Glu Thr Thr Ile Glu Asp Leu Cys Asp Gly Tyr Pro
305                 310                 315                 320

Arg Gln Phe Ala Asp Phe Leu His His Ala Arg Glu Leu Gly Phe Tyr
                325                 330                 335

Glu Gln Pro Asp Tyr Ser Tyr Leu Arg Ser Leu Phe Arg Asp Leu Phe
            340                 345                 350

Ile Gln Lys Lys Phe Gln Leu Asp His Val Tyr Asp Trp Thr Val Tyr
        355                 360                 365

Thr Gln Pro Pro Gln Asn Gly Ser Ala Gln Thr Val Arg Ser Pro Ala
    370                 375                 380
```

Ala Gly Pro Gln Thr His Leu Gln Ser Arg Pro Ser Asn Val Ser Tyr
385                 390                 395                 400

Cys Pro Pro Leu Thr Lys Pro Glu Phe Arg Arg Glu Val Val Ala Ala
                405                 410                 415

Asn

<210> SEQ ID NO 9
<211> LENGTH: 1575
<212> TYPE: DNA
<213> ORGANISM: Saccharomyces cerevisiae

<400> SEQUENCE: 9

```
atgtcccaac gatcttcaca acacattgta ggtattcatt atgctgtagg acctaagatt      60
ggcgaagggt ctttcggagt aatatttgag ggagagaaca ttcttcattc ttgtcaagcg     120
cagaccggta gcaagaggga ctctagtata ataatggcga acgagccagt cgcaattaaa     180
ttcgaaccgc gacattcgga cgcaccccag ttgcgtgacg aatttagagc ctataggata     240
ttgaatggct gcgttggaat tccccatgct tattattttg gtcaagaagg tatgcacaac     300
atcttgatta tcgatttact agggccatca ttggaagatc tctttgagtg gtgtggtaga     360
aaattttcag tgaaaacaac ctgtatggtt gccaagcaaa tgattgatag agttagagca     420
attcatgatc acgacttaat ctatcgcgat attaaacccg ataactttt aatttctcaa      480
tatcaaagaa tttcacctga aggaaaagtc attaaatcat gtgcctcctc ttctaataat     540
gatcccaatt aatatacat ggttgacttt ggtatggcaa acaatatag agatccaaga       600
acgaaacaac atataccata ccgtgaacga aaatcattga gcggtaccgc cagatatatg     660
tctattaata ctcattttgg aagagaacag tcacgtaggg atgatttaga atcgctaggt     720
cacgtttttt tttatttctt gaggggatcc ttgccatggc aaggtttgaa agcaccaaac     780
aacaaactga agtatgaaaa gattggtatg actaaacaga aattgaatcc tgatgatctt     840
ttattgaata atgctattcc ttatcagttt gccacatatt aaaatatgc acgttccttg      900
aagttcgacg aagatccgga ttatgactat ttaatctcgt taatggatga cgctttgaga     960
ttaaacgact taaggatga tggacactat gactggatgg atttgaatgg tggtaaaggc     1020
tggaatatca agattaatag aagagctaac ttgcatggtt acggaaatcc aaatccaaga    1080
gtcaatggca atactgcaag aaacaatgtg aatacgaatt caaagacacg aaatacaacg    1140
ccagttgcga cacctaagca acaagctcaa aacagttata caaggacaa ttcgaaatcc     1200
agaatttctt cgaacccgca gagctttact aaacaacaac acgtcttgaa aaaaatcgaa    1260
cccaatagta aatatattcc tgaaacacat tcaaatcttc aacggccaat taaaagtcaa    1320
agtcaaacgt acgactccat cagtcataca caaaattcac catttgtacc atattcaagt    1380
tctaaagcta accctaaaag aagtaataat gagcacaact taccaaacca ctacacaaac    1440
cttgcaaata gaatatcaa ttatcaaagt caacgaaatt acgaacaaga aatgatgct     1500
tattctgatg acgagaatga tacattttgt tctaaaatat acaaatattg ttgttgctgt    1560
ttttgttgct gttga                                                     1575
```

<210> SEQ ID NO 10
<211> LENGTH: 524
<212> TYPE: PRT
<213> ORGANISM: Saccharomyces cerevisiae

<400> SEQUENCE: 10

Met Ser Gln Arg Ser Ser Gln His Ile Val Gly Ile His Tyr Ala Val

-continued

```
  1               5                   10                  15

Gly Pro Lys Ile Gly Glu Gly Ser Phe Gly Val Ile Phe Glu Gly Glu
            20                  25                  30

Asn Ile Leu His Ser Cys Gln Ala Gln Thr Gly Ser Lys Arg Asp Ser
            35                  40                  45

Ser Ile Ile Met Ala Asn Glu Pro Val Ala Ile Lys Phe Glu Pro Arg
50                  55                  60

His Ser Asp Ala Pro Gln Leu Arg Asp Glu Phe Arg Ala Tyr Arg Ile
65                  70                  75                  80

Leu Asn Gly Cys Val Gly Ile Pro His Ala Tyr Tyr Phe Gly Gln Glu
            85                  90                  95

Gly Met His Asn Ile Leu Ile Ile Asp Leu Leu Gly Pro Ser Leu Glu
            100                 105                 110

Asp Leu Phe Glu Trp Cys Gly Arg Lys Phe Ser Val Lys Thr Thr Cys
            115                 120                 125

Met Val Ala Lys Gln Met Ile Asp Arg Val Arg Ala Ile His Asp His
            130                 135                 140

Asp Leu Ile Tyr Arg Asp Ile Lys Pro Asp Asn Phe Leu Ile Ser Gln
145                 150                 155                 160

Tyr Gln Arg Ile Ser Pro Glu Gly Lys Val Ile Lys Ser Cys Ala Ser
            165                 170                 175

Ser Ser Asn Asn Asp Pro Asn Leu Ile Tyr Met Val Asp Phe Gly Met
            180                 185                 190

Ala Lys Gln Tyr Arg Asp Pro Arg Thr Lys Gln His Ile Pro Tyr Arg
            195                 200                 205

Glu Arg Lys Ser Leu Ser Gly Thr Ala Arg Tyr Met Ser Ile Asn Thr
            210                 215                 220

His Phe Gly Arg Glu Gln Ser Arg Arg Asp Asp Leu Glu Ser Leu Gly
225                 230                 235                 240

His Val Phe Phe Tyr Phe Leu Arg Gly Ser Leu Pro Trp Gln Gly Leu
            245                 250                 255

Lys Ala Pro Asn Asn Lys Leu Lys Tyr Glu Lys Ile Gly Met Thr Lys
            260                 265                 270

Gln Lys Leu Asn Pro Asp Asp Leu Leu Leu Asn Asn Ala Ile Pro Tyr
            275                 280                 285

Gln Phe Ala Thr Tyr Leu Lys Tyr Ala Arg Ser Leu Lys Phe Asp Glu
            290                 295                 300

Asp Pro Asp Tyr Asp Tyr Leu Ile Ser Leu Met Asp Asp Ala Leu Arg
305                 310                 315                 320

Leu Asn Asp Leu Lys Asp Asp Gly His Tyr Asp Trp Met Asp Leu Asn
            325                 330                 335

Gly Gly Lys Gly Trp Asn Ile Lys Ile Asn Arg Arg Ala Asn Leu His
            340                 345                 350

Gly Tyr Gly Asn Pro Asn Pro Arg Val Asn Gly Asn Thr Ala Arg Asn
            355                 360                 365

Asn Val Asn Thr Asn Ser Lys Thr Arg Asn Thr Thr Pro Val Ala Thr
            370                 375                 380

Pro Lys Gln Gln Ala Gln Asn Ser Tyr Asn Lys Asp Asn Ser Lys Ser
385                 390                 395                 400

Arg Ile Ser Ser Asn Pro Gln Ser Phe Thr Lys Gln Gln His Val Leu
            405                 410                 415

Lys Lys Ile Glu Pro Asn Ser Lys Tyr Ile Pro Glu Thr His Ser Asn
            420                 425                 430
```

```
Leu Gln Arg Pro Ile Lys Ser Gln Ser Gln Thr Tyr Asp Ser Ile Ser
            435                 440                 445

His Thr Gln Asn Ser Pro Phe Val Pro Tyr Ser Ser Lys Ala Asn
        450                 455                 460

Pro Lys Arg Ser Asn Asn Glu His Asn Leu Pro Asn His Tyr Thr Asn
465                 470                 475                 480

Leu Ala Asn Lys Asn Ile Asn Tyr Gln Ser Gln Arg Asn Tyr Glu Gln
                485                 490                 495

Glu Asn Asp Ala Tyr Ser Asp Asp Glu Asn Asp Thr Phe Cys Ser Lys
            500                 505                 510

Ile Tyr Lys Tyr Cys Cys Cys Cys Phe Cys Cys Cys
            515                 520

<210> SEQ ID NO 11
<211> LENGTH: 1525
<212> TYPE: DNA
<213> ORGANISM: Brassica napus

<400> SEQUENCE: 11
agttgtctga atttgagaaa aaaagtctga gactttgttt tagagagaaa tcaatggatc      60
ttgtgattgg tgggaaattc aaacttggca gaaaaattgg cagtggatca tttggagagc     120
tctatcttgg tgtaaatgtc caaaccggag aagaagttgc tgttaagctg aatctgtca     180 agaccaagca tcctcagcta cactatgagt ccaaattgta tacgttgctt caaggaggaa     240
gtggtattcc taacatcaag tggtatggag ttgatggaga atacaatgtt atggttattg     300
accttctagg tccaagtctt gaagacttgt tcaactactg caaccgaaaa ctctctttga     360
aaaccgttct catgcttgct gatcaactta ttaacagagt tgagtatatg cacactagag     420
gtttccttca ccgtgatatt aagcctgaca acttcttaat gggcctcggc cgcaaagcaa     480
accaggttta taattgat tttggattgg ggaagaaata cagagacctt cagactcaca     540
ggcacattcc ttacagagaa aacaaaaacc tcactggaac agctcggtat gcaagtgtca     600
acacacacct tggagtagaa caaagtcgaa gggacgattt ggaagcagtt ggttatgtgc     660
ttatgtactt cctcaaagga agcttaccat ggcagggatt aaaagctggg acaaggaagc     720
agaagtatga cagaataagt gagaagaaag tctcaactcc tatagaggtc ttatgtagaa     780
accaaccgtc tgagtttgtt tcttacttcc gctactgccg gtctctacgg tttgatgaca     840
aacctgatta ctcttacctc aagaggctat tccgagactt gtttattaga gaaggttatc     900
agtttgatta tgtatttgac tggaccgtct tgaagcatcc gcaaactggt tccagctcca     960
gttctagttc aagaacacgg gatcatacaa ctggaaaacc ggagttaact gctggaaaaac    1020 cggagaggac tgctggcaat aggttatcag gtgcggttga agcttttttca agaaggcatg    1080 caacaccacg tgatcggtct gcatcaagaa actctgatga tgtccctgtt ggtggtggtg    1140
agtcagaaag aagaggcagt tcgtcaagaa acggaagctc ttcaaggaga gcaatcgcct    1200
cgagctcacg tccaagttca gctgggggtc tagtgatag cagatcctct agccgtttgg    1260
tgacttcaag cggcggtggt ggaatgggat caacgagcca gagaatggga ccaggaggat    1320
atgagtcaaa agagagttcg actctttccc gtggtgctag aaacactcgg ggagatccgt    1380
taaggaggag cttcgagctt ctttctcttc gtaaatcatg agaaacatac aaagaaagag    1440
attttataca aacgaaaatc tatatatata tatataagat atacaataca aacgattcat    1500
atacttcaaa aaaaaaaaaa aaaaa                                           1525
```

```
<210> SEQ ID NO 12
<211> LENGTH: 455
<212> TYPE: PRT
<213> ORGANISM: Brassica napus

<400> SEQUENCE: 12

Met Asp Leu Val Ile Gly Gly Lys Phe Lys Leu Gly Arg Lys Ile Gly
  1               5                  10                  15

Ser Gly Ser Phe Gly Glu Leu Tyr Leu Gly Val Asn Val Gln Thr Gly
                 20                  25                  30

Glu Glu Val Ala Val Lys Leu Glu Ser Val Lys Thr Lys His Pro Gln
             35                  40                  45

Leu His Tyr Glu Ser Lys Leu Tyr Thr Leu Leu Gln Gly Gly Ser Gly
         50                  55                  60

Ile Pro Asn Ile Lys Trp Tyr Gly Val Asp Gly Glu Tyr Asn Val Met
 65                  70                  75                  80

Val Ile Asp Leu Leu Gly Pro Ser Leu Glu Asp Leu Phe Asn Tyr Cys
                 85                  90                  95

Asn Arg Lys Leu Ser Leu Lys Thr Val Leu Met Leu Ala Asp Gln Leu
            100                 105                 110

Ile Asn Arg Val Glu Tyr Met His Thr Arg Gly Phe Leu His Arg Asp
        115                 120                 125

Ile Lys Pro Asp Asn Phe Leu Met Gly Leu Gly Arg Lys Ala Asn Gln
130                 135                 140

Val Tyr Ile Ile Asp Phe Gly Leu Gly Lys Lys Tyr Arg Asp Leu Gln
145                 150                 155                 160

Thr His Arg His Ile Pro Tyr Arg Glu Asn Lys Asn Leu Thr Gly Thr
                165                 170                 175

Ala Arg Tyr Ala Ser Val Asn Thr His Leu Gly Val Glu Gln Ser Arg
            180                 185                 190

Arg Asp Asp Leu Glu Ala Val Gly Tyr Val Leu Met Tyr Phe Leu Lys
        195                 200                 205

Gly Ser Leu Pro Trp Gln Gly Leu Lys Ala Gly Thr Arg Lys Gln Lys
    210                 215                 220

Tyr Asp Arg Ile Ser Glu Lys Lys Val Ser Thr Pro Ile Glu Val Leu
225                 230                 235                 240

Cys Arg Asn Gln Pro Ser Glu Phe Val Ser Tyr Phe Arg Tyr Cys Arg
                245                 250                 255

Ser Leu Arg Phe Asp Asp Lys Pro Asp Tyr Ser Tyr Leu Lys Arg Leu
            260                 265                 270

Phe Arg Asp Leu Phe Ile Arg Glu Gly Tyr Gln Phe Asp Tyr Val Phe
        275                 280                 285

Asp Trp Thr Val Leu Lys His Pro Gln Thr Gly Ser Ser Ser Ser Ser
    290                 295                 300

Ser Ser Arg Thr Arg Asp His Thr Thr Gly Lys Pro Glu Leu Thr Ala
305                 310                 315                 320

Gly Lys Pro Glu Arg Thr Ala Gly Asn Arg Leu Ser Gly Ala Val Glu
                325                 330                 335

Ala Phe Ser Arg Arg His Ala Thr Pro Arg Asp Arg Ser Ala Ser Arg
            340                 345                 350

Asn Ser Asp Asp Val Pro Val Gly Gly Gly Glu Ser Glu Arg Arg Gly
        355                 360                 365

Ser Ser Arg Asn Gly Ser Ser Arg Arg Ala Ile Ala Ser Ser
    370                 375                 380
```

```
Ser Arg Pro Ser Ser Ala Gly Gly Pro Ser Asp Ser Arg Ser Ser
385                 390                 395                 400

Arg Leu Val Thr Ser Ser Gly Gly Gly Met Gly Ser Thr Ser Gln
            405                 410                 415

Arg Met Gly Pro Gly Gly Tyr Glu Ser Lys Lys Ser Ser Thr Leu Ser
                420                 425                 430

Arg Gly Ala Arg Asn Thr Arg Gly Asp Pro Leu Arg Arg Ser Phe Glu
        435                 440                 445

Leu Leu Ser Leu Arg Lys Ser
    450                 455

<210> SEQ ID NO 13
<211> LENGTH: 1716
<212> TYPE: DNA
<213> ORGANISM: Brassica napus

<400> SEQUENCE: 13
gaaagagaga gataaagcaa aggagacaat ctacattcct ttttgttgtt cccccagatc      60
acgagaagaa ggagtctaga gagaaggtga ctatcgggtt cctctgtttt ccctgtttc     120 atcaaccta attccccaga aaattcaatc tttccttgct tctttccctg agacaatcct     180
gggtttgcgg ctctgactcc gttggattaa aaggtttctt caaagacgca ttttgctttc     240
gatagaggat aaaagtttcc tcttttaagt cggctttggg gttgatggag gctcgtgtgg     300
ggaacaagtt tcgtctcgga cgcaaaatcg ggagcggttc ttttggagag atccatctcg     360
gtactcatct tcaaacgaat gaagaagtcg ccatcaagct tgaaaatgcc aagacaaaac     420
atccacagct gctttatgaa tccaagttat acagacttct acagggagga actggtgttc     480
caaatctcaa gtggtttggt gttgaaggcg actacaatgt tctggtcatg gatttacttg     540
gacctagtct tgaagacttg ttcaatttct gtagcaggaa acttttctctc aagtccgtcc     600 tcatgcttgc tgatcaaatg ataaaccgtg ttgagtattt ccattcgaaa tctttcctcc     660
accgagatct caagcctgac aacttcctca tgggggttagg gagacgcgcc aaccaggtat     720
acatcatcga ctttggtctt gcaaagaagt acagagataa cactactcat cagcacattc     780
cttaccgaga aaacaagaat ctcactggaa ctgcaagata tgctagtatg aacactcact     840
tgggaattga acaaagcaga agggatgact tagaatctct tggttacatt tcatgtatt     900 tccttaaagg aagtcttcca tggcaagggc ttaaagctgg aaccaagaaa caaaatatg     960 agagaatcag cgaaaagaaa gtctctacat ccattgagtc cttatgccgt ggctacccat    1020
ctgagttcgc atcctacttc cattactgcc gctccctccg gtttgatgat aaaccagatt    1080
acggttacct caaaagaata ttcagagatc tcttcatccg cgaagggttt caattcgatt    1140
atgtctttga ctggaccata ctgaagtacc aacagtcaca gctaacagct cctccaacac    1200
gtggccctgc ggctggaacc agttcgggtt tgtctccagg attgaccagc actgatagat    1260
acggagagga agatggaggg agaccaccga tggattcatc aagaaggaga acatcaggag    1320
ctctcgagaa ctcatcagct gctgttagag ctccaatgat gccaagctcg tcgctgttcg    1380
gacaatcagc aggatcatcg aggagagtaa cgtctgagga gctgcagaga agccgtacgg    1440
gcagtggatt gagaaactct gggatggttt caacgtcgga gaggaagaga tcttcttcca    1500
ctaggaaaca atatgattct gctatcaaag gcattgagac tctccatgtc tctgacgaaa    1560
ggtatcacca ccattgatct atcggttaga aagagaaaaa acatgtcatg tttgtattaa    1620
tcatataaag attcgactct atatattaga gaaaccagta tttttttgtgt tgtttttaat    1680
```
cttctcattt tttacgtgaa aaaaaaaaaa aaaaaa    1716

<210> SEQ ID NO 14
<211> LENGTH: 430
<212> TYPE: PRT
<213> ORGANISM: Brassica napus

<400> SEQUENCE: 14

```
Met Glu Ala Arg Val Gly Asn Lys Phe Arg Leu Gly Arg Lys Ile Gly
  1               5                  10                  15

Ser Gly Ser Phe Gly Glu Ile His Leu Gly Thr His Leu Gln Thr Asn
             20                  25                  30

Glu Glu Val Ala Ile Lys Leu Glu Asn Ala Lys Thr Lys His Pro Gln
         35                  40                  45

Leu Leu Tyr Glu Ser Lys Leu Tyr Arg Leu Leu Gln Gly Gly Thr Gly
     50                  55                  60

Val Pro Asn Leu Lys Trp Phe Gly Val Glu Gly Asp Tyr Asn Val Leu
 65                  70                  75                  80

Val Met Asp Leu Leu Gly Pro Ser Leu Glu Asp Leu Phe Asn Phe Cys
                 85                  90                  95

Ser Arg Lys Leu Ser Leu Lys Ser Val Leu Met Leu Ala Asp Gln Met
            100                 105                 110

Ile Asn Arg Val Glu Tyr Phe His Ser Lys Ser Phe Leu His Arg Asp
        115                 120                 125

Leu Lys Pro Asp Asn Phe Leu Met Gly Leu Gly Arg Arg Ala Asn Gln
    130                 135                 140

Val Tyr Ile Ile Asp Phe Gly Leu Ala Lys Lys Tyr Arg Asp Asn Thr
145                 150                 155                 160

Thr His Gln His Ile Pro Tyr Arg Glu Asn Lys Asn Leu Thr Gly Thr
                165                 170                 175

Ala Arg Tyr Ala Ser Met Asn Thr His Leu Gly Ile Glu Gln Ser Arg
            180                 185                 190

Arg Asp Asp Leu Glu Ser Leu Gly Tyr Ile Leu Met Tyr Phe Leu Lys
        195                 200                 205

Gly Ser Leu Pro Trp Gln Gly Leu Lys Ala Gly Thr Lys Lys Gln Lys
    210                 215                 220

Tyr Glu Arg Ile Ser Glu Lys Lys Val Ser Thr Ser Ile Glu Ser Leu
225                 230                 235                 240

Cys Arg Gly Tyr Pro Ser Glu Phe Ala Ser Tyr Phe His Tyr Cys Arg
                245                 250                 255

Ser Leu Arg Phe Asp Asp Lys Pro Asp Tyr Gly Tyr Leu Lys Arg Ile
            260                 265                 270

Phe Arg Asp Leu Phe Ile Arg Glu Gly Phe Gln Phe Asp Tyr Val Phe
        275                 280                 285

Asp Trp Thr Ile Leu Lys Tyr Gln Gln Ser Gln Leu Thr Ala Pro Pro
    290                 295                 300

Thr Arg Gly Pro Ala Ala Gly Thr Ser Ser Gly Leu Ser Pro Gly Leu
305                 310                 315                 320

Thr Ser Thr Asp Arg Tyr Gly Glu Glu Asp Gly Gly Arg Pro Pro Met
                325                 330                 335

Asp Ser Ser Arg Arg Arg Thr Ser Gly Ala Leu Glu Asn Ser Ser Ala
            340                 345                 350

Ala Val Arg Ala Pro Met Met Pro Ser Ser Ser Leu Phe Gly Gln Ser
        355                 360                 365
```

Ala Gly Ser Ser Arg Arg Val Thr Ser Glu Glu Leu Gln Arg Ser Arg
        370                 375                 380

Thr Gly Ser Gly Leu Arg Asn Ser Gly Met Val Ser Thr Ser Glu Arg
385                 390                 395                 400

Lys Arg Ser Ser Thr Arg Lys Gln Tyr Asp Ser Ala Ile Lys Gly
                405                 410                 415

Ile Glu Thr Leu His Val Ser Asp Glu Arg Tyr His His His
            420                 425                 430

<210> SEQ ID NO 15
<211> LENGTH: 1830
<212> TYPE: DNA
<213> ORGANISM: Brassica napus

<400> SEQUENCE: 15

| | | | | | |
|---|---|---|---|---|---|
| cggcgattca | actcttcttc | cacggcggca | ttggatggtt | ccttctctga | cgcaggagag | 60 |
| aaagagagaa | agaattttga | acaggtgtt | tagggttctt | gtctgaatgg | acttgaaaat | 120 |
| ggataatgta | atcggtggca | agtttaagct | tggtcggaag | atcggcggtg | gctcttttgg | 180 |
| agagctttt | cttggagtaa | gtgtgcaaac | cggagaagag | gtcgctgtaa | agctggagcc | 240 |
| tgcgaaaact | aagcatccac | aacttcatta | tgagtccaag | atttatatgc | ttctacaagg | 300 |
| aggaactggc | atccccagcc | tcaagtggtt | tggggttcag | ggagactaca | atgcgatggt | 360 |
| cattgatctc | cttggtccga | gtttggaaga | tttgttcaac | tattgtaata | gaaagctcac | 420 |
| tttgaaggca | gttctgatgc | ttgcggatca | actgattagc | agagttgagt | atatgcattc | 480 |
| aagaggattt | ctacaccgag | acataaaacc | agacaatttc | ttgatgggac | ttggtcgcaa | 540 |
| agcaaaccag | gtgtatgtca | ttgattttgg | ccttgcaaag | aagtataggg | atctccaaac | 600 |
| acatagacac | atcccctaca | gagaaaacaa | gaaccttacg | ggcacagctc | ggtatgctag | 660 |
| cgtcaacact | caccttggtg | ttgagcaaag | tcgaagggat | gatctggagt | ctcttggtta | 720 |
| cgtgctcatg | tatttcctca | gaggaagcct | gccatggcag | ggactaaaag | ctggcacaaa | 780 |
| gaagcagaag | tatgacagaa | tcagtgagaa | gaaagtttca | actcctatag | aggtcttgtg | 840 |
| caagtcctat | ccacaagaat | tcgtatcata | ctttcaatac | tgcaggtcct | gcgattcga | 900 |
| agacaaacca | gactactcgt | atctaaagag | gctattccgg | gatttgttta | ccgcgaagg | 960 |
| ctatcagttt | gactatgtat | ttgactggac | tgcactgaaa | caccctcaga | gtagttctag | 1020 |
| ctcccggtcc | agctcacacg | gaaggcatcg | tacgggtaaa | ccagttgcgg | ccgcaggacc | 1080 |
| gtctgctgag | aaacctgaaa | ggatctcagt | tgggagggaa | atccgcgaca | gattctctgg | 1140 |
| tgcagttgaa | gcattcgcga | gaaggaacgc | tacaggagcc | actccccatc | aaaaccaaac | 1200 |
| caagcatcga | actcttgacg | atgttcctcc | accaatgaaa | cctgctgtga | atatggtatc | 1260 |
| tgagaaagga | agaaacactt | ccggatacgg | cagtgcttca | aggagagcgg | tggcctcagg | 1320 |
| gagtagacca | agctcatcag | gtgaacaagg | ggacagccgc | ggttcaagcc | gtgtggcctc | 1380 |
| tagtggaggt | ggtgttcgac | cttctgtttt | ccagagagct | caagcggcag | ctggtgtgag | 1440 |
| tggatatgag | tcgaagacag | cctctgcctt | taaccgcaac | agagtggctg | cttctaggac | 1500 |
| tgcacgtgac | gatgctctca | gaagctttga | gcttctttct | atccgcaaat | gagaaagtta | 1560 |
| gtaagaacaa | acgaaagtta | ctatcaactc | ttttctgta | aattggattc | ttctttacac | 1620 |
| gtgtgttgtt | tggtcctcac | gtttccacga | aactaccaaa | ttttccatgt | attatgaatg | 1680 |
| taacgtttct | ctggatttttt | gtattaaatt | gttacgctct | tgtactgtaa | tcacgacaag | 1740 |

```
ttgttactcg tatatcttaa tttttgtgta aaaaaaaaaa aaaaaaaaaa aaaaaaaaaa    1800
aaaaaaaaaa ataaaaaaaa aaaaaaaaaa                                    1830
```

<210> SEQ ID NO 16
<211> LENGTH: 481
<212> TYPE: PRT
<213> ORGANISM: Brassica napus

<400> SEQUENCE: 16

```
Met Asp Leu Lys Met Asp Asn Val Ile Gly Gly Lys Phe Lys Leu Gly
  1               5                  10                  15

Arg Lys Ile Gly Gly Ser Phe Gly Glu Leu Phe Leu Gly Val Ser
                 20                  25                  30

Val Gln Thr Gly Glu Glu Val Ala Val Lys Leu Glu Pro Ala Lys Thr
             35                  40                  45

Lys His Pro Gln Leu His Tyr Glu Ser Lys Ile Tyr Met Leu Leu Gln
         50                  55                  60

Gly Gly Thr Gly Ile Pro Ser Leu Lys Trp Phe Gly Val Gln Gly Asp
 65                  70                  75                  80

Tyr Asn Ala Met Val Ile Asp Leu Leu Gly Pro Ser Leu Glu Asp Leu
                 85                  90                  95

Phe Asn Tyr Cys Asn Arg Lys Leu Thr Leu Lys Ala Val Leu Met Leu
            100                 105                 110

Ala Asp Gln Leu Ile Ser Arg Val Glu Tyr Met His Ser Arg Gly Phe
        115                 120                 125

Leu His Arg Asp Ile Lys Pro Asp Asn Phe Leu Met Gly Leu Gly Arg
130                 135                 140

Lys Ala Asn Gln Val Tyr Val Ile Asp Phe Gly Leu Ala Lys Lys Tyr
145                 150                 155                 160

Arg Asp Leu Gln Thr His Arg His Ile Pro Tyr Arg Glu Asn Lys Asn
                165                 170                 175

Leu Thr Gly Thr Ala Arg Tyr Ala Ser Val Asn Thr His Leu Gly Val
            180                 185                 190

Glu Gln Ser Arg Arg Asp Asp Leu Glu Ser Leu Gly Tyr Val Leu Met
        195                 200                 205

Tyr Phe Leu Arg Gly Ser Leu Pro Trp Gln Gly Leu Lys Ala Gly Thr
210                 215                 220

Lys Lys Gln Lys Tyr Asp Arg Ile Ser Glu Lys Lys Val Ser Thr Pro
225                 230                 235                 240

Ile Glu Val Leu Cys Lys Ser Tyr Pro Gln Glu Phe Val Ser Tyr Phe
                245                 250                 255

Gln Tyr Cys Arg Ser Leu Arg Phe Glu Asp Lys Pro Tyr Ser Tyr
            260                 265                 270

Leu Lys Arg Leu Phe Arg Asp Leu Phe Ile Arg Glu Gly Tyr Gln Phe
        275                 280                 285

Asp Tyr Val Phe Asp Trp Thr Ala Leu Lys His Pro Gln Ser Ser Ser
290                 295                 300

Ser Ser Arg Ser Ser Ser His Gly Arg His Arg Thr Gly Lys Pro Val
305                 310                 315                 320

Ala Ala Ala Gly Pro Ser Ala Glu Lys Pro Glu Arg Ile Ser Val Gly
                325                 330                 335

Arg Glu Ile Arg Asp Arg Phe Ser Gly Ala Val Glu Ala Phe Ala Arg
            340                 345                 350

Arg Asn Ala Thr Gly Ala Thr Pro His Gln Asn Gln Thr Lys His Arg
```

```
                355              360              365
Thr Leu Asp Asp Val Pro Pro Met Lys Pro Ala Val Asn Met Val
    370              375              380

Ser Glu Lys Gly Arg Asn Thr Ser Gly Tyr Gly Ser Ala Ser Arg Arg
385              390              395              400

Ala Val Ala Ser Gly Ser Arg Pro Ser Ser Ser Gly Glu Gln Gly Asp
                405              410              415

Ser Arg Gly Ser Ser Arg Val Ala Ser Ser Gly Gly Val Arg Pro
                420              425              430

Ser Val Phe Gln Arg Ala Gln Ala Ala Ala Gly Val Ser Gly Tyr Glu
                435              440              445

Ser Lys Thr Ala Ser Ala Phe Asn Arg Asn Arg Val Ala Ala Ser Arg
    450              455              460

Thr Ala Arg Asp Asp Ala Leu Arg Ser Phe Glu Leu Leu Ser Ile Arg
465              470              475              480

Lys

<210> SEQ ID NO 17
<211> LENGTH: 1887
<212> TYPE: DNA
<213> ORGANISM: Brassica napus

<400> SEQUENCE: 17
```

| | | | | | |
|---|---|---|---|---|---|
| ttcgccgagg | ctatttcacc | ggaagtcaaa | cgaaatccac | cgctactcct | accttcaatc | 60 |
| cgattgattc | ccttccgctg | tagctatctc | atacgcctta | agtacgctgc | tccagtagct | 120 |
| tcttgtggtg | gctagtagta | tagaggtagt | tctagggttt | cgatttgatg | gagccgcgag | 180 |
| tcggaaacaa | gtttcggctg | gggcggaaga | tcggaagtgg | atcattcgga | gagatctatc | 240 |
| ttggtactga | tatacagact | aatgaagaag | ttgccattaa | actcgaaaat | gtgaaaacta | 300 |
| agcatcctca | gttactgtat | gaatcaaaat | tatataaagt | attacaagga | ggaaccggcg | 360 |
| ttccaaacat | taaatggtat | ggtgttgaag | gggaatataa | cgtccttgtg | atagacttgt | 420 |
| tgggcctag | ccttgaagat | ctattcaatt | tctgtagtag | gaaactctca | ctaaagactg | 480 |
| tactgatgct | tgccgatcaa | atgatcaatc | gcattgaatt | tgttcatcag | aggtcatttc | 540 |
| tacaccggga | catcaagcct | gacaactttc | tgatgggtct | cgggaggcgc | gcaaatcagg | 600 |
| tatacatcat | cgactttggt | ctagcgaaga | agtacagaga | ctcgaatcat | cagcatattc | 660 |
| cgtacaggga | aaacaaaaac | ttaactggaa | ctgctagata | cgccagcatg | aacactcacc | 720 |
| ttggcattga | acaaagccgt | agggatgatt | tggagtcact | tggatttgtt | ctcatgtact | 780 |
| ttttaaaagg | aagtcttcct | tggcaaggac | tgaaagctgg | taataagaag | caaaagtatg | 840 |
| agaggattag | tgaaaagaaa | gtatcgacat | ctattgagtc | tttatgccga | ggatatccat | 900 |
| ctgaatttgc | ttcttacttc | cattattgcc | ggtccctgag | attcgatgac | aagccagact | 960 |
| atgcctacct | gaaacggctt | ttccgtgacc | tgtttattcg | cgaaggcttc | cagtttgatt | 1020 |
| atgtatttga | ctggactatc | ttgaagtatc | agcaatcaca | gctttctact | cctccccgtc | 1080 |
| ccaatgtccc | tggagttggg | caaagctctg | gccttccccc | tgctattgct | agtgctgaga | 1140 |
| ggccatcagg | tggcgaggaa | gctagaactt | ctggctggcc | atcaggaaac | gctaggcgga | 1200 |
| tttctggaca | aatatttaat | tcaggcaact | tagctaaaca | aaaagcacca | gtttcaagtg | 1260 |
| atcctgcaat | ctctaaaaat | gtaatgttat | ctagctctag | cttttctccgc | gcaactgggt | 1320 |
| catcaagacg | tgctgctgtc | tccggtagtc | gcgaggctgc | agttcctgga | actgattctg | 1380 |

-continued

```
agccatcaaa ccctcaaatc attgaagctg aacaagctc caacccaaag attcatggtg    1440
gtcgaagctc acctatagtc tcatctgaga acaagaagct atcatctcca tcaaggggaa   1500
atacttcagt tatgaagaac tatgagtcca atcttaataa agggatcgag ggtctgcact   1560
tttagccgct gggtacccac tgaccagtga atgatgtttg taaatttaaa gaccaaagaa   1620
aacctttctt aggccctccc caggttttag agggagggag actttgattg tgcttgtaag   1680
cactctcaaa taacagaaga taaagtaaag actctggaag aagtgattcc agaggaatac   1740
aaactcagaa gtgagtcaag gagtcaaaag actgttgtgt atgtctcgtt tggtactgca   1800
aagttaattt cgagtctcaa agggatttga agtgtaagcg ataattgtac tgttttttt    1860 aaaaaaaaaa aaaaaaaaaa aaaaaaa                                      1887
```

```
<210> SEQ ID NO 18
<211> LENGTH: 465
<212> TYPE: PRT
<213> ORGANISM: Brassica napus

<400> SEQUENCE: 18

Met Glu Pro Arg Val Gly Asn Lys Phe Arg Leu Gly Arg Lys Ile Gly
 1               5                  10                  15

Ser Gly Ser Phe Gly Glu Ile Tyr Leu Gly Thr Asp Ile Gln Thr Asn
                20                  25                  30

Glu Glu Val Ala Ile Lys Leu Glu Asn Val Lys Thr Lys His Pro Gln
            35                  40                  45

Leu Leu Tyr Glu Ser Lys Leu Tyr Lys Val Leu Gln Gly Gly Thr Gly
        50                  55                  60

Val Pro Asn Ile Lys Trp Tyr Gly Val Glu Gly Glu Tyr Asn Val Leu
    65                  70                  75                  80

Val Ile Asp Leu Phe Gly Pro Ser Leu Glu Asp Leu Phe Asn Phe Cys
                85                  90                  95

Ser Arg Lys Leu Ser Leu Lys Thr Val Leu Met Leu Ala Asp Gln Met
               100                 105                 110

Ile Asn Arg Ile Glu Phe Val His Gln Arg Ser Phe Leu His Arg Asp
           115                 120                 125

Ile Lys Pro Asp Asn Phe Leu Met Gly Leu Gly Arg Arg Ala Asn Gln
       130                 135                 140

Val Tyr Ile Ile Asp Phe Gly Leu Ala Lys Lys Tyr Arg Asp Ser Asn
145                 150                 155                 160

His Gln His Ile Pro Tyr Arg Glu Asn Lys Asn Leu Thr Gly Thr Ala
               165                 170                 175

Arg Tyr Ala Ser Met Asn Thr His Leu Gly Ile Glu Gln Ser Arg Arg
           180                 185                 190

Asp Asp Leu Glu Ser Leu Gly Phe Val Leu Met Tyr Phe Leu Lys Gly
       195                 200                 205

Ser Leu Pro Trp Gln Gly Leu Lys Ala Gly Asn Lys Lys Gln Lys Tyr
   210                 215                 220

Glu Arg Ile Ser Glu Lys Lys Val Ser Thr Ser Ile Glu Ser Leu Cys
225                 230                 235                 240

Arg Gly Tyr Pro Ser Glu Phe Ala Ser Tyr Phe His Tyr Cys Arg Ser
               245                 250                 255

Leu Arg Phe Asp Asp Lys Pro Asp Tyr Ala Tyr Leu Lys Arg Leu Phe
           260                 265                 270

Arg Asp Leu Phe Ile Arg Glu Gly Phe Gln Phe Asp Tyr Val Phe Asp
       275                 280                 285
```

-continued

```
Trp Thr Ile Leu Lys Tyr Gln Gln Ser Gln Leu Ser Thr Pro Pro Arg
    290                 295                 300

Pro Asn Val Pro Gly Val Gly Gln Ser Ser Gly Leu Pro Pro Ala Ile
305                 310                 315                 320

Ala Ser Ala Glu Arg Pro Ser Gly Gly Glu Glu Ala Arg Thr Ser Gly
                325                 330                 335

Trp Pro Ser Gly Asn Ala Arg Arg Ile Ser Gly Gln Ile Phe Asn Ser
            340                 345                 350

Gly Asn Leu Ala Lys Gln Lys Ala Pro Val Ser Ser Asp Pro Ala Ile
        355                 360                 365

Ser Lys Asn Val Met Leu Ser Ser Ser Phe Leu Arg Ala Thr Gly
    370                 375                 380

Ser Ser Arg Arg Ala Ala Val Ser Gly Ser Arg Glu Ala Ala Val Pro
385                 390                 395                 400

Gly Thr Asp Ser Glu Pro Ser Asn Pro Gln Ile Ile Glu Ala Gly Thr
                405                 410                 415

Ser Ser Asn Pro Lys Ile His Gly Gly Arg Ser Ser Pro Ile Val Ser
            420                 425                 430

Ser Glu Asn Lys Lys Leu Ser Ser Pro Ser Arg Gly Asn Thr Ser Val
        435                 440                 445

Met Lys Asn Tyr Glu Ser Asn Leu Asn Lys Gly Ile Glu Gly Leu His
    450                 455                 460

Phe
465

<210> SEQ ID NO 19
<211> LENGTH: 2276
<212> TYPE: DNA
<213> ORGANISM: Brassica napus

<400> SEQUENCE: 19
ggagaagagg tggtggtggt ggtagaggaa gaggaaccgc tgcagcttta gccaaagccg      60
ccgcacctcc aagaccgact ggtgctaccg gtagggtcg aggcatcagg ttaatagatt     120
tagaagcaga gcctataggt gagcctgctt ttaatcaagt ccaaggggta gctgataagg     180
gtatcgccat ggaaggtggt agcccggaga agatagttgg tgtgggagaa gatccaagca     240
cagctccagt ccctgaaagg gtacaagttg gaagctctcc tgtttataag actgagagga     300
aactcggtaa aggaggcttt ggtcaagttt ttgttggtag aagggtgagt ggtggcagcg     360
ataggattgg ccctgatgca gttgaggtgg ctctgaaatt tgagcacaaa aatagcaaag     420
gatgcaattt tggtccacct tacgagtggc aagtgtacag taatctcaac ggttgctatg     480
gagttcctgc ggtacattat aagggtcgtc aaggagattt ttacatcctt gtcatggaca     540
tgcttggtcc gagtctctgg gatgtttgga actcttcagg gcaatcgatg tcaccaaaca     600
tggtagcgtg cattgcagtt gagtctatat ctattcttga gaacttcac atgaaagggt     660 ttgtccatgg agatgtgaag cctgaaaact ttttactcgg tcaacccgga acagcagatg     720
agaaaaaact ctaccttatc gatcttggtc tagcatcaaa atggaaagaa gctcactcag     780
gcctgcatgt tgaatatgat caaagacctg atgttcag ggggactgta aggtatgcaa     840
gtgttcatgc acatctagga cgtactggaa gtcgaagaga tgatcttgag tcattggctt     900
atactctaat ttttctattg aaaggaagat tgccatggca aggttaccag ggtgataaca     960
agagctttct tgtttgcaag aaaaagatgt caacttctcc tgaagtgatg tgctgttct    1020
```

-continued

```
gtccaccacc gtttaagcta ttccttgagg cagttactaa tctgaagttt gacgaggagc    1080
ctaattatgc aaagcttatt tcgattttcg atactttaat tgagccgtgc gctctatcta    1140
gaccagttag aatcgatggg gctctcaagg ttggacaaaa gcgtggaaga ctggttctca    1200
atttggaaga ggatgaacaa ccgaagaaga agatcagaat aggcactcct gccactcaat    1260
ggatttcagt ttataatgct cgtcgtccca tgaaacagag atatcactac aatgttgcag    1320
agacaagact gagccagcat gtacagaagg gtaatgaaga tggtcttttg attagctgtg    1380
tagcatcagc agcgaatctc tgggcccttta ttatggatgc tggaactgga tttacctctc    1440
aagtttatga attgtcaaag gtcttcctgc acaaggattg gattatggaa caatgggaaa    1500
agaactacta tataagttcc atagctggtg cagataacgg gagctcctta gttgttatgt    1560
caaaaggaac tacttatact cagcagtcat acaaagtgag cgactcgttt ccattcaagt    1620
ggataaacaa gaaatggaaa gaagattttc atgtgacgtc catgacaact gctggtaatc    1680
gttggggtgt ggtaatgtcg aggaactctg gcttctctga tcaggtggtg gagcttggac    1740
tttttgtacc caagcgatgg aatacatagg acctgggaga gtgggtatag aatcacatca    1800
atggcagcaa ctgcagatca agcagccttc atattaagca taccaaaacg taaaatgatg    1860
gatgaaactc aggagactct tcggaccacc gcctttccaa gtactcatgt caaggagaaa    1920
tgggcgaaaa atctgcacat tgcatcagta tgctatggca ggacagtgtg ctgaactgct    1980
gatactacat ttaacatcat atgttcagtt agaaagccaa agacaattag agctgcttat    2040
ggatcgtcat aataccccaa tcaaaagagg taaaaacgag acgcagcctg tttggctggt    2100
tgaatgtaat gaatagatgt cttggtaatg tatgtaacaa gttacaaaag cgaagatgga    2160
attaggaatt agagaaaaga tttgagggct tttgaagcct taagtgtgtg cttacttatt    2220
gttatcgttt tacttgcttg aaataatgtg agaaacgcaa aaaaaaaaaa aaaaaa        2276
```

<210> SEQ ID NO 20
<211> LENGTH: 526
<212> TYPE: PRT
<213> ORGANISM: Brassica napus

<400> SEQUENCE: 20

```
Met Glu Gly Gly Ser Pro Glu Lys Ile Val Gly Val Gly Glu Asp Pro
 1               5                  10                  15

Ser Thr Ala Pro Val Pro Glu Arg Val Gln Val Gly Ser Ser Pro Val
            20                  25                  30

Tyr Lys Thr Glu Arg Lys Leu Gly Lys Gly Gly Phe Gly Gln Val Phe
        35                  40                  45

Val Gly Arg Arg Val Ser Gly Gly Ser Asp Arg Ile Gly Pro Asp Ala
    50                  55                  60

Val Glu Val Ala Leu Lys Phe Glu His Lys Asn Ser Lys Gly Cys Asn
65                  70                  75                  80

Phe Gly Pro Pro Tyr Glu Trp Gln Val Tyr Ser Asn Leu Asn Gly Cys
                85                  90                  95

Tyr Gly Val Pro Ala Val His Tyr Lys Gly Arg Gln Gly Asp Phe Tyr
            100                 105                 110

Ile Leu Val Met Asp Met Leu Gly Pro Ser Leu Trp Asp Val Trp Asn
        115                 120                 125

Ser Ser Gly Gln Ser Met Ser Pro Asn Met Val Ala Cys Ile Ala Val
    130                 135                 140

Glu Ser Ile Ser Ile Leu Glu Lys Leu His Met Lys Gly Phe Val His
145                 150                 155                 160
```

```
Gly Asp Val Lys Pro Glu Asn Phe Leu Leu Gly Gln Pro Gly Thr Ala
                165                 170                 175

Asp Glu Lys Lys Leu Tyr Leu Ile Asp Leu Gly Leu Ala Ser Lys Trp
                180                 185                 190

Lys Glu Ala His Ser Gly Leu His Val Glu Tyr Asp Gln Arg Pro Asp
                195                 200                 205

Val Phe Arg Gly Thr Val Arg Tyr Ala Ser Val His Ala His Leu Gly
                210                 215                 220

Arg Thr Gly Ser Arg Arg Asp Asp Leu Glu Ser Leu Ala Tyr Thr Leu
225                 230                 235                 240

Ile Phe Leu Leu Lys Gly Arg Leu Pro Trp Gln Gly Tyr Gln Gly Asp
                245                 250                 255

Asn Lys Ser Phe Leu Val Cys Lys Lys Met Ser Thr Ser Pro Glu
                260                 265                 270

Val Met Cys Cys Phe Cys Pro Pro Phe Lys Leu Phe Leu Glu Ala
                275                 280                 285

Val Thr Asn Leu Lys Phe Asp Glu Glu Pro Asn Tyr Ala Lys Leu Ile
                290                 295                 300

Ser Ile Phe Asp Thr Leu Ile Glu Pro Cys Ala Leu Ser Arg Pro Val
305                 310                 315                 320

Arg Ile Asp Gly Ala Leu Lys Val Gly Gln Lys Arg Gly Arg Leu Val
                325                 330                 335

Leu Asn Leu Glu Glu Asp Glu Gln Pro Lys Lys Ile Arg Ile Gly
                340                 345                 350

Thr Pro Ala Thr Gln Trp Ile Ser Val Tyr Asn Ala Arg Arg Pro Met
                355                 360                 365

Lys Gln Arg Tyr His Tyr Asn Val Ala Glu Thr Arg Leu Ser Gln His
                370                 375                 380

Val Gln Lys Gly Asn Glu Asp Gly Leu Leu Ile Ser Cys Val Ala Ser
385                 390                 395                 400

Ala Ala Asn Leu Trp Ala Leu Ile Met Asp Ala Gly Thr Gly Phe Thr
                405                 410                 415

Ser Gln Val Tyr Glu Leu Ser Lys Val Phe Leu His Lys Asp Trp Ile
                420                 425                 430

Met Glu Gln Trp Glu Lys Asn Tyr Tyr Ile Ser Ser Ile Ala Gly Ala
                435                 440                 445

Asp Asn Gly Ser Ser Leu Val Val Met Ser Lys Gly Thr Thr Tyr Thr
450                 455                 460

Gln Gln Ser Tyr Lys Val Ser Asp Ser Phe Pro Phe Lys Trp Ile Asn
465                 470                 475                 480

Lys Lys Trp Lys Glu Asp Phe His Val Thr Ser Met Thr Thr Ala Gly
                485                 490                 495

Asn Arg Trp Gly Val Val Met Ser Arg Asn Ser Gly Phe Ser Asp Gln
                500                 505                 510

Val Val Glu Leu Gly Leu Phe Val Pro Lys Arg Trp Asn Thr
                515                 520                 525

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 21
caggaaacag ctatgacc                                                    18

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctaaagggaa caaaagctg                                                   19

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgtaaaacga cggccagt                                                    18

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgaccgcagc ccatgaggaa gttat                                            25

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atcccgggct cacgtagtgc actgaactct gtc                                   33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcgttaacat gcccatcttc tcatactcag acc                                   33

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
```
ctcgcctacc aagccccatt agaaa                                        25

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atcccgggtt gtcgaggacg gagagagaag ag                                32

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcgttaacct taggaatcgt atggcagaga gct                               33

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgtgtctacg tgtcgcgggg tcgat                                        25

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atcccgggag gcattgaact acctggagtg ag                                32

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcgatatcgt tgaactagta atctgtgtta actt                              34

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
ggaattccag ctgaccacca tgtcccaacg atcttcacaa cac                    43
```

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
gatccccggg aattgccatg tcaaaaaaaa aaaggaaaaa gagaaaag               48
```

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

```
gcgctgcaga tttcatttgg agaggacacg                                   30
```

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
cgcggccggc ctcagaagaa ctcgtcaaga aggcg                             35
```

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
ggaattccag ctgaccacca tggcaattcc cggggatc                          38
```

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

```
gctgacacgc caagcctcgc tagtc                                        25
```

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
gcgttaacat gcccatcttc tcatactcag acc                               33
```

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gctgacacgc aagcctcgc tagtc					25

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gcgttaacct taggaatcgt atggcagaga gct					33

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
atcccgggag gcattgaact acctggagtg ag					32

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
gcgatatcgt tgaactagta atctgtgtta actttatc					38

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
gcctgcctag ccccatcaag aaatt					25

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
atcccgggcg cagcatgtga ctcgtcacct g					31

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
gcgttaacag ctactacttg ctctaggaag ctg                                    33

<210> SEQ ID NO 47
<211> LENGTH: 538
<212> TYPE: PRT
<213> ORGANISM: Saccharomyces cerevisiae

<400> SEQUENCE: 47

```
Met Ser Met Pro Ile Ala Ser Thr Thr Leu Ala Val Asn Asn Leu Thr
 1               5                  10                  15

Asn Ile Asn Gly Asn Ala Asn Phe Asn Val Gln Ala Asn Lys Gln Leu
             20                  25                  30

His His Gln Ala Val Asp Ser Pro Ala Arg Ser Ser Met Thr Ala Thr
         35                  40                  45

Thr Ala Ala Asn Ser Asn Ser Asn Ser Ser Arg Asp Asp Ser Thr Ile
     50                  55                  60

Val Gly Leu His Tyr Lys Ile Gly Lys Lys Ile Gly Glu Gly Ser Phe
 65                  70                  75                  80

Gly Val Leu Phe Glu Gly Thr Asn Met Ile Asn Gly Val Pro Val Ala
                 85                  90                  95

Ile Lys Phe Glu Pro Arg Lys Thr Glu Ala Pro Gln Leu Arg Asp Glu
            100                 105                 110

Tyr Lys Thr Tyr Lys Ile Leu Asn Gly Thr Pro Asn Ile Pro Tyr Ala
        115                 120                 125

Tyr Tyr Phe Gly Gln Glu Gly Leu His Asn Ile Leu Val Ile Asp Leu
    130                 135                 140

Leu Gly Pro Ser Leu Glu Asp Leu Phe Asp Trp Cys Gly Arg Lys Phe
145                 150                 155                 160

Ser Val Lys Thr Val Val Gln Val Ala Val Gln Met Ile Thr Leu Ile
                165                 170                 175

Glu Asp Leu His Ala His Asp Leu Ile Tyr Arg Asp Ile Lys Pro Asp
            180                 185                 190

Asn Phe Leu Ile Gly Arg Pro Gly Gln Pro Asp Ala Asn Asn Ile His
        195                 200                 205

Leu Ile Asp Phe Gly Met Ala Lys Gln Tyr Arg Asp Pro Lys Thr Lys
    210                 215                 220

Gln His Ile Pro Tyr Arg Glu Lys Lys Ser Leu Ser Gly Thr Ala Arg
225                 230                 235                 240

Tyr Met Ser Ile Asn Thr His Leu Gly Arg Glu Gln Ser Arg Arg Asp
                245                 250                 255

Asp Met Glu Ala Leu Gly His Val Phe Phe Tyr Phe Leu Arg Gly His
            260                 265                 270

Leu Pro Trp Gln Gly Leu Lys Ala Pro Asn Asn Lys Gln Lys Tyr Glu
        275                 280                 285

Lys Ile Gly Glu Lys Lys Arg Ser Thr Asn Val Tyr Asp Leu Ala Gln
    290                 295                 300

Gly Leu Pro Val Gln Phe Gly Arg Tyr Leu Glu Ile Val Arg Ser Leu
```

```
305                 310                 315                 320

Ser Phe Glu Glu Cys Pro Asp Tyr Glu Gly Tyr Arg Lys Leu Leu Leu
                325                 330                 335

Ser Val Leu Asp Asp Leu Gly Glu Thr Ala Asp Gly Gln Tyr Asp Trp
                340                 345                 350

Met Lys Leu Asn Asp Gly Arg Gly Trp Asp Leu Asn Ile Asn Lys Lys
                355                 360                 365

Pro Asn Leu His Gly Tyr Gly His Pro Asn Pro Asn Glu Lys Ser
                370                 375                 380

Arg Lys His Arg Asn Lys Gln Leu Gln Met Gln Gln Leu Gln Met Gln
385                 390                 395                 400

Gln Leu Gln Gln Gln Gln Gln Gln Gln Tyr Ala Gln Lys Thr Glu
                405                 410                 415

Ala Asp Met Arg Asn Ser Gln Tyr Lys Pro Lys Leu Asp Pro Thr Ser
                420                 425                 430

Tyr Glu Ala Tyr Gln His Gln Thr Gln Gln Lys Tyr Leu Gln Glu Gln
                435                 440                 445

Gln Lys Arg Gln Gln Gln Lys Leu Gln Glu Gln Gln Leu Gln Glu
                450                 455                 460

Gln Gln Leu Gln Gln Gln Gln Gln Gln Gln Leu Arg Ala Thr
465                 470                 475                 480

Gly Gln Pro Pro Ser Gln Pro Gln Ala Gln Thr Gln Ser Gln Gln Phe
                485                 490                 495

Gly Ala Arg Tyr Gln Pro Gln Gln Pro Ser Ala Ala Leu Arg Thr
                500                 505                 510

Pro Glu Gln His Pro Asn Asp Asp Asn Ser Ser Leu Ala Ala Ser His
                515                 520                 525

Lys Gly Phe Phe Gln Lys Leu Gly Cys Cys
                530                 535

<210> SEQ ID NO 48
<211> LENGTH: 546
<212> TYPE: PRT
<213> ORGANISM: Saccharomyces cerevisiae

<400> SEQUENCE: 48

Met Ser Gln Val Gln Ser Pro Leu Thr Ala Thr Asn Ser Gly Leu Ala
 1               5                  10                  15

Val Asn Asn Asn Thr Met Asn Ser Gln Met Pro Asn Arg Ser Asn Val
                20                  25                  30

Arg Leu Val Asn Gly Thr Leu Pro Pro Ser Leu His Val Ser Ser Asn
                35                  40                  45

Leu Asn His Asn Thr Gly Asn Ser Ser Ala Ser Tyr Ser Gly Ser Gln
                50                  55                  60

Ser Arg Asp Asp Ser Thr Ile Val Gly Leu His Tyr Lys Ile Gly Lys
65                  70                  75                  80

Lys Ile Gly Glu Gly Ser Phe Gly Val Leu Phe Glu Gly Thr Asn Met
                85                  90                  95

Ile Asn Gly Leu Pro Val Ala Ile Lys Phe Glu Pro Arg Lys Thr Glu
                100                 105                 110

Ala Pro Gln Leu Lys Asp Glu Tyr Arg Thr Tyr Lys Ile Leu Ala Gly
                115                 120                 125

Thr Pro Gly Ile Pro Gln Glu Tyr Tyr Phe Gly Gln Glu Gly Leu His
                130                 135                 140
```

-continued

```
Asn Ile Leu Val Ile Asp Leu Gly Pro Ser Leu Glu Asp Leu Phe
145                 150                 155                 160

Asp Trp Cys Gly Arg Arg Phe Ser Val Lys Thr Val Gln Val Ala
            165                 170                 175

Val Gln Met Ile Thr Leu Ile Glu Asp Leu His Ala His Asp Leu Ile
            180                 185                 190

Tyr Arg Asp Ile Lys Pro Asp Asn Phe Leu Ile Gly Arg Pro Gly Gln
        195                 200                 205

Pro Asp Ala Asn Lys Val His Leu Ile Asp Phe Gly Met Ala Lys Gln
        210                 215                 220

Tyr Arg Asp Pro Lys Thr Lys Gln His Ile Pro Tyr Arg Glu Lys Lys
225                 230                 235                 240

Ser Leu Ser Gly Thr Ala Arg Tyr Met Ser Ile Asn Thr His Leu Gly
                245                 250                 255

Arg Glu Gln Ser Arg Arg Asp Asp Met Glu Ala Met Gly His Val Phe
                260                 265                 270

Phe Tyr Phe Leu Arg Gly Gln Leu Pro Trp Gln Gly Leu Lys Ala Pro
            275                 280                 285

Asn Asn Lys Gln Lys Tyr Glu Lys Ile Gly Glu Lys Lys Arg Leu Thr
290                 295                 300

Asn Val Tyr Asp Leu Ala Gln Gly Leu Pro Ile Gln Phe Gly Arg Tyr
305                 310                 315                 320

Leu Glu Ile Val Arg Asn Leu Ser Phe Glu Glu Thr Pro Asp Tyr Glu
                325                 330                 335

Gly Tyr Arg Met Leu Leu Leu Ser Val Leu Asp Asp Leu Gly Glu Thr
            340                 345                 350

Ala Asp Gly Gln Tyr Asp Trp Met Lys Leu Asn Gly Gly Arg Gly Trp
            355                 360                 365

Asp Leu Ser Ile Asn Lys Lys Pro Asn Leu His Gly Tyr Gly His Pro
        370                 375                 380

Asn Pro Pro Asn Glu Lys Ser Lys Arg His Arg Ser Lys Asn His Gln
385                 390                 395                 400

Tyr Ser Ser Pro Asp His His His Tyr Asn Gln Gln Gln Gln
                405                 410                 415

Gln Gln Ala Gln Ala Gln Ala Gln Ala Gln Ala Lys Val Gln
            420                 425                 430

Gln Gln Gln Leu Gln Gln Ala Gln Ala Gln Gln Ala Asn Arg Tyr
            435                 440                 445

Gln Leu Gln Pro Asp Asp Ser His Tyr Asp Glu Arg Glu Ala Ser
        450                 455                 460

Lys Leu Asp Pro Thr Ser Tyr Glu Ala Tyr Gln Gln Thr Gln Gln
465                 470                 475                 480

Lys Tyr Ala Gln Gln Gln Lys Gln Met Gln Gln Lys Ser Lys Gln
            485                 490                 495

Phe Ala Asn Thr Gly Ala Asn Gly Gln Thr Asn Lys Tyr Pro Tyr Asn
            500                 505                 510

Ala Gln Pro Thr Ala Asn Asp Glu Gln Asn Ala Lys Asn Ala Ala Gln
        515                 520                 525

Asp Arg Asn Ser Asn Lys Ser Ser Lys Gly Phe Phe Ser Lys Leu Gly
        530                 535                 540

Cys Cys
545
```

-continued

<210> SEQ ID NO 49
<211> LENGTH: 416
<212> TYPE: PRT
<213> ORGANISM: Homo sapiens

<400> SEQUENCE: 49

| Met | Glu | Leu | Arg | Val | Gly | Asn | Lys | Tyr | Arg | Leu | Gly | Arg | Lys | Ile | Gly |
|---|---|---|---|---|---|---|---|---|---|---|---|---|---|---|---|
| 1 | | | | 5 | | | | | 10 | | | | | 15 | |

| Ser | Gly | Ser | Phe | Gly | Asp | Ile | Tyr | Leu | Gly | Ala | Asn | Ile | Ala | Ser | Gly |
| | | | 20 | | | | | 25 | | | | | 30 | | |

| Glu | Glu | Val | Ala | Ile | Lys | Leu | Glu | Cys | Val | Lys | Thr | Lys | His | Pro | Gln |
| | | | 35 | | | | | 40 | | | | | 45 | | |

| Leu | His | Ile | Glu | Ser | Lys | Phe | Tyr | Lys | Met | Met | Gln | Gly | Gly | Val | Gly |
| | | | 50 | | | | | 55 | | | | | 60 | | |

| Ile | Pro | Ser | Ile | Lys | Trp | Cys | Gly | Ala | Glu | Gly | Asp | Tyr | Asn | Val | Met |
| 65 | | | | | 70 | | | | | 75 | | | | | 80 |

| Val | Met | Glu | Leu | Leu | Gly | Pro | Ser | Leu | Glu | Asp | Leu | Phe | Asn | Phe | Cys |
| | | | | 85 | | | | | 90 | | | | | 95 | |

| Ser | Arg | Lys | Phe | Ser | Leu | Lys | Thr | Val | Leu | Leu | Leu | Ala | Asp | Gln | Met |
| | | | | 100 | | | | | 105 | | | | | 110 | |

| Ile | Ser | Arg | Ile | Glu | Tyr | Ile | His | Ser | Lys | Asn | Phe | Ile | His | Arg | Asp |
| | | | | 115 | | | | | 120 | | | | | 125 | |

| Val | Lys | Pro | Asp | Asn | Phe | Leu | Met | Gly | Leu | Gly | Lys | Lys | Gly | Asn | Leu |
| | | | 130 | | | | | 135 | | | | | 140 | | |

| Val | Tyr | Ile | Ile | Asp | Phe | Gly | Leu | Ala | Lys | Lys | Tyr | Arg | Asp | Ala | Arg |
| 145 | | | | | 150 | | | | | 155 | | | | | 160 |

| Thr | His | Gln | His | Ile | Pro | Tyr | Arg | Glu | Asn | Lys | Asn | Leu | Thr | Gly | Thr |
| | | | | 165 | | | | | 170 | | | | | 175 | |

| Ala | Arg | Tyr | Ala | Ser | Ile | Asn | Thr | His | Leu | Gly | Ile | Glu | Gln | Ser | Arg |
| | | | 180 | | | | | 185 | | | | | 190 | | |

| Arg | Asp | Asp | Leu | Glu | Ser | Leu | Gly | Tyr | Val | Leu | Met | Tyr | Phe | Asn | Leu |
| | | | | 195 | | | | | 200 | | | | | 205 | |

| Gly | Ser | Leu | Pro | Trp | Gln | Gly | Leu | Lys | Ala | Ala | Thr | Lys | Arg | Gln | Lys |
| | | | 210 | | | | | 215 | | | | | 220 | | |

| Tyr | Glu | Arg | Ile | Ser | Glu | Lys | Lys | Met | Ser | Thr | Pro | Ile | Glu | Val | Leu |
| 225 | | | | | 230 | | | | | 235 | | | | | 240 |

| Cys | Lys | Gly | Tyr | Pro | Ser | Glu | Phe | Ser | Thr | Tyr | Leu | Asn | Phe | Cys | Arg |
| | | | | 245 | | | | | 250 | | | | | 255 | |

| Ser | Leu | Arg | Phe | Asp | Asp | Lys | Pro | Asp | Tyr | Ser | Tyr | Leu | Arg | Gln | Leu |
| | | | 260 | | | | | 265 | | | | | 270 | | |

| Phe | Arg | Asn | Leu | Phe | His | Arg | Gln | Gly | Phe | Ser | Tyr | Asp | Tyr | Val | Phe |
| | | | | 275 | | | | | 280 | | | | | 285 | |

| Asp | Trp | Asn | Met | Leu | Lys | Phe | Gly | Ala | Ala | Arg | Asn | Pro | Glu | Asp | Val |
| | | | 290 | | | | | 295 | | | | | 300 | | |

| Asp | Arg | Glu | Arg | Glu | His | Glu | Arg | Glu | Arg | Met | Gly | Gln | Leu |
| 305 | | | | | 310 | | | | | 315 | | | | | 320 |

| Arg | Gly | Ser | Ala | Thr | Arg | Ala | Leu | Pro | Pro | Gly | Pro | Thr | Gly | Ala |
| | | | | 325 | | | | | 330 | | | | | 335 | |

| Thr | Ala | Asn | Arg | Leu | Arg | Ser | Ala | Ala | Glu | Pro | Val | Ala | Ser | Thr | Pro |
| | | | 340 | | | | | 345 | | | | | 350 | | |

| Ala | Ser | Arg | Ile | Gln | Pro | Ala | Gly | Asn | Thr | Ser | Pro | Arg | Ala | Ile | Ser |
| | | | | 355 | | | | | 360 | | | | | 365 | |

| Arg | Val | Asp | Arg | Glu | Arg | Lys | Val | Ser | Met | Arg | Leu | His | Arg | Gly | Ala |
| | | | 370 | | | | | 375 | | | | | 380 | | |

Pro Ala Asn Val Ser Ser Asp Leu Thr Gly Arg Gln Glu Val Ser
385                 390                 395                 400

Arg Ile Pro Ala Ser Gln Thr Ser Val Pro Phe Asp His Leu Gly Lys
                405                 410                 415

<210> SEQ ID NO 50
<211> LENGTH: 415
<212> TYPE: PRT
<213> ORGANISM: Homo sapiens

<400> SEQUENCE: 50

Met Glu Leu Arg Val Gly Asn Arg Tyr Arg Leu Gly Arg Lys Ile Gly
1               5                   10                  15

Ser Gly Ser Phe Gly Asp Ile Tyr Leu Gly Thr Asp Ile Ala Ala Gly
                20                  25                  30

Glu Glu Val Ala Ile Lys Leu Glu Cys Val Lys Thr Lys His Pro Gln
            35                  40                  45

Leu His Ile Glu Ser Lys Ile Tyr Lys Met Met Gln Gly Gly Val Gly
    50                  55                  60

Ile Pro Thr Ile Arg Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                85                  90                  95

Ser Arg Lys Phe Ser Leu Lys Thr Val Leu Leu Leu Ala Asp Gln Met
                100                 105                 110

Ile Ser Arg Ile Glu Tyr Ile His Ser Lys Asn Phe Ile His Arg Asp
                115                 120                 125

Val Lys Pro Asp Asn Phe Leu Met Gly Leu Gly Lys Lys Gly Asn Leu
        130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
                180                 185                 190

Arg Asp Asp Leu Glu Ser Leu Gly Tyr Val Leu Met Tyr Phe Asn Leu
        195                 200                 205

Gly Ser Leu Pro Trp Gln Gly Leu Lys Ala Ala Thr Lys Arg Gln Lys
210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ala Thr Tyr Leu Asn Phe Cys Arg
                245                 250                 255

Ser Leu Arg Phe Asp Asp Lys Pro Asp Tyr Ser Tyr Leu Arg Gln Leu
                260                 265                 270

Phe Arg Asn Leu Phe His Arg Gln Gly Phe Ser Tyr Asp Tyr Val Phe
            275                 280                 285

Asp Trp Asn Met Leu Lys Phe Gly Ala Ser Arg Ala Ala Asp Asp Ala
    290                 295                 300

Glu Arg Glu Arg Arg Asp Arg Glu Glu Arg Leu Arg His Ser Arg Asn
305                 310                 315                 320

Pro Ala Thr Arg Gly Leu Pro Ser Thr Ala Ser Gly Arg Leu Arg Gly
                325                 330                 335

Thr Gln Glu Val Ala Pro Pro Thr Pro Leu Thr Pro Thr Ser His Thr
                340                 345                 350

```
Ala Asn Thr Ser Pro Arg Pro Val Ser Gly Met Glu Arg Glu Arg Lys
            355                 360                 365

Val Ser Met Arg Leu His Arg Gly Ala Pro Val Asn Ile Ser Ser Ser
    370                 375                 380

Asp Leu Thr Gly Arg Gln Asp Thr Ser Arg Met Ser Thr Ser Gln Ile
385                 390                 395                 400

Pro Gly Arg Val Ala Ser Ser Gly Leu Gln Ser Val Val His Arg
                405                 410                 415

<210> SEQ ID NO 51
<211> LENGTH: 337
<212> TYPE: PRT
<213> ORGANISM: Homo sapiens

<400> SEQUENCE: 51

Met Ala Ser Ser Gly Ser Lys Ala Glu Phe Ile Val Gly Gly Lys
  1               5                  10                  15

Tyr Lys Leu Val Arg Lys Ile Gly Ser Gly Ser Phe Gly Asp Ile Tyr
                 20                  25                  30

Leu Ala Ile Asn Ile Thr Asn Gly Glu Glu Val Ala Val Lys Leu Glu
             35                  40                  45

Ser Gln Lys Ala Arg His Pro Gln Leu Leu Tyr Glu Ser Lys Leu Tyr
         50                  55                  60

Lys Ile Leu Gln Gly Gly Val Gly Ile Pro His Ile Arg Trp Tyr Gly
 65                  70                  75                  80

Gln Glu Lys Asp Tyr Asn Val Leu Val Met Asp Leu Leu Gly Pro Ser
                 85                  90                  95

Leu Glu Asp Leu Phe Asn Phe Cys Ser Arg Arg Phe Thr Met Lys Thr
            100                 105                 110

Val Leu Met Leu Ala Asp Gln Met Ile Ser Arg Ile Glu Tyr Val His
            115                 120                 125

Thr Lys Asn Phe Ile His Arg Asp Ile Lys Pro Asp Asn Phe Leu Met
130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
                165                 170                 175

Glu Asp Lys Asn Leu Thr Gly Thr Ala Arg Tyr Ala Ser Ile Asn Ala
            180                 185                 190

His Leu Gly Ile Glu Gln Ser Arg Arg Asp Asp Met Glu Ser Leu Gly
        195                 200                 205

Tyr Val Leu Met Tyr Phe Asn Arg Thr Ser Leu Pro Trp Gln Gly Leu
    210                 215                 220

Lys Ala Ala Thr Lys Lys Gln Lys Tyr Glu Lys Ile Ser Glu Lys Lys
225                 230                 235                 240

Met Ser Thr Pro Val Glu Val Leu Cys Lys Gly Phe Pro Ala Glu Phe
                245                 250                 255

Ala Met Tyr Leu Asn Tyr Cys Arg Gly Leu Arg Phe Glu Glu Ala Pro
            260                 265                 270

Asp Tyr Met Tyr Leu Arg Gln Leu Phe Arg Ile Leu Phe Arg Thr Leu
        275                 280                 285

Asn His Gln Tyr Asp Tyr Thr Phe Asp Trp Thr Met Leu Lys Gln Lys
    290                 295                 300

Ala Ala Gln Gln Ala Ala Ser Ser Ser Gly Gln Gly Gln Gln Ala Gln
```

```
            305                 310                 315                 320
Thr Pro Thr Gly Lys Gln Thr Asp Lys Thr Lys Ser Asn Met Lys Gly
                    325                 330                 335
Phe

<210> SEQ ID NO 52
<211> LENGTH: 447
<212> TYPE: PRT
<213> ORGANISM: Homo sapiens

<400> SEQUENCE: 52

Met Glu Asn Lys Lys Asp Lys Asp Lys Ser Asp Asp Arg Met Ala
  1               5                  10                  15

Arg Pro Ser Gly Arg Ser Gly His Asn Thr Arg Gly Thr Gly Ser Ser
                 20                  25                  30

Ser Ser Gly Val Leu Met Val Gly Pro Asn Phe Arg Val Gly Lys Lys
             35                  40                  45

Ile Gly Cys Gly Asn Phe Gly Glu Leu Arg Leu Gly Lys Asn Leu Tyr
         50                  55                  60

Thr Asn Glu Tyr Val Ala Ile Lys Leu Glu Pro Met Lys Ser Arg Ala
 65                  70                  75                  80

Pro Gln Leu His Leu Glu Tyr Arg Phe Tyr Lys Gln Leu Gly Ser Gly
                 85                  90                  95

Asp Gly Ile Pro Gln Val Tyr Tyr Phe Gly Pro Cys Gly Lys Tyr Asn
            100                 105                 110

Ala Met Val Leu Glu Leu Leu Gly Pro Ser Leu Glu Asp Leu Phe Asp
            115                 120                 125

Leu Cys Asp Arg Thr Phe Ser Leu Lys Thr Val Leu Met Ile Ala Ile
        130                 135                 140

Gln Leu Ile Ser Arg Met Glu Tyr Val His Ser Lys Asn Leu Ile Tyr
145                 150                 155                 160

Arg Asp Val Lys Pro Glu Asn Phe Leu Ile Gly Arg Pro Arg Asn Lys
                165                 170                 175

Thr Gln Gln Val Ile His Ile Ile Asp Phe Gly Leu Ala Lys Glu Tyr
            180                 185                 190

Ile Asp Pro Glu Thr Lys Lys His Ile Pro Tyr Arg Glu His Lys Ser
        195                 200                 205

Leu Thr Gly Thr Ala Arg Tyr Met Ser Ile Asn Thr His Leu Gly Lys
    210                 215                 220

Glu Gln Ser Arg Arg Asp Asp Leu Glu Ala Leu Gly His Met Phe Met
225                 230                 235                 240

Tyr Phe Leu Arg Gly Ser Leu Pro Trp Gln Gly Leu Lys Ala Asp Thr
                245                 250                 255

Leu Lys Glu Arg Tyr Gln Lys Ile Gly Asp Thr Lys Arg Ala Thr Pro
            260                 265                 270

Ile Glu Val Leu Cys Glu Asn Phe Pro Glu Met Ala Thr Tyr Leu Arg
        275                 280                 285

Tyr Val Arg Arg Leu Asp Phe Phe Glu Lys Pro Asp Tyr Glu Tyr Leu
    290                 295                 300

Arg Lys Leu Phe Thr Asp Leu Phe Asp Arg Lys Gly Tyr Met Phe Asp
305                 310                 315                 320

Tyr Glu Tyr Asp Trp Ile Gly Lys Gln Leu Pro Thr Pro Val Gly Ala
                325                 330                 335

Val Gln Gln Asp Pro Ala Leu Ser Ser Asn Arg Glu Ala His Gln His
```

-continued

```
                340                 345                 350
Arg Asp Lys Met Gln Gln Ser Lys Asn Gln Ser Ala Asp His Arg Ala
            355                 360                 365
Ala Trp Asp Ser Gln Gln Ala Asn Pro His His Leu Arg Ala His Leu
        370                 375                 380
Ala Ala Asp Arg His Gly Gly Ser Val Gln Val Val Ser Ser Thr Asn
385                 390                 395                 400
Gly Glu Leu Asn Thr Asp Asp Pro Thr Ala Gly Arg Ser Asn Ala Pro
                405                 410                 415
Ile Thr Ala Pro Thr Glu Val Glu Val Met Asp Glu Thr Lys Cys Cys
            420                 425                 430
Cys Phe Phe Lys Arg Arg Lys Arg Lys Thr Ile Gln Arg His Lys
        435                 440                 445

<210> SEQ ID NO 53
<211> LENGTH: 463
<212> TYPE: PRT
<213> ORGANISM: Oryza sativa

<400> SEQUENCE: 53

Met Glu His Val Ile Gly Gly Lys Phe Lys Leu Gly Arg Lys Ile Gly
1               5                   10                  15
Ser Gly Ser Phe Gly Glu Leu Tyr Leu Gly Val Asn Ile Gln Ser Ser
            20                  25                  30
Glu Glu Val Ala Ile Lys Leu Glu Ser Val Lys Ser Arg His Pro Gln
        35                  40                  45
Leu His Tyr Glu Ser Lys Leu Tyr Met Leu Leu Gln Gly Gly Thr Gly
    50                  55                  60
Ile Pro His Leu Lys Trp Phe Gly Val Glu Gly Glu Tyr Asn Val Met
65                  70                  75                  80
Val Ile Asp Leu Leu Gly Pro Ser Leu Glu Asp Leu Phe Asn Tyr Cys
                85                  90                  95
Asn Arg Lys Phe Ser Leu Lys Thr Val Leu Met Leu Ala Asp Gln Met
            100                 105                 110
Ile Asn Arg Val Glu Tyr Met His Thr Arg Gly Phe Leu His Arg Asp
        115                 120                 125
Ile Lys Pro Asp Asn Phe Leu Met Gly Leu Gly Arg Lys Ala Ser Gln
    130                 135                 140
Val Tyr Val Ile Asp Tyr Val Leu Ala Lys Lys Tyr Arg Asp Leu Gln
145                 150                 155                 160
Thr His Lys His Ile Pro Tyr Arg Glu Asn Lys Asn Leu Thr Gly Thr
                165                 170                 175
Ala Arg Tyr Ala Ser Val Asn Thr His Leu Gly Val Glu Gln Ser Arg
            180                 185                 190
Arg Asp Asp Leu Glu Ser Leu Gly Tyr Val Leu Met Tyr Phe Leu Arg
        195                 200                 205
Gly Ser Leu Pro Trp Gln Gly Leu Lys Ala Gly Thr Lys Lys Gln Lys
    210                 215                 220
Tyr Asp Lys Ile Ser Glu Lys Lys Met Leu Thr Pro Val Glu Val Leu
225                 230                 235                 240
Cys Lys Ser Tyr Pro Thr Glu Phe Ile Ser Tyr Phe His Tyr Cys Arg
                245                 250                 255
Ser Leu Arg Phe Glu Asp Lys Pro Asp Tyr Ser Tyr Leu Lys Arg Leu
            260                 265                 270
```

-continued

```
Phe Arg Asp Leu Phe Ile Arg Glu Gly Tyr Gln Leu Asp Tyr Ile Phe
        275                 280                 285

Asp Trp Thr Lys Gln Gly Ser Glu Ser Asn Arg Leu Arg Ser Ser Gly
    290                 295                 300

Arg Thr Ser Gly Leu Val Gly Pro Ser Ala Glu Arg Thr Glu Arg Ala
305                 310                 315                 320

Ala Ala Arg Gln Asp Val Pro Asp Arg Phe Ser Gly Thr Val Asp Pro
                325                 330                 335

Phe Ala Arg Arg Thr Gly Ser Gly Ser Gly His Tyr Gly Glu His Thr
            340                 345                 350

Lys His Arg Asn Ile Leu Asp Ser Leu Leu Ala Pro Lys Thr Ala Val
        355                 360                 365

Asp Leu Asp Lys Arg Arg Pro Thr Ser Ser Ser Arg Asn Gly Ser Thr
    370                 375                 380

Ser Arg Lys Ala Leu Leu Ser Ser Ser Arg Pro Ser Ser Gly Asp Pro
385                 390                 395                 400

Ile Asp Pro Asn Arg Ser Asn Leu Ile Pro Thr Ser Ser Gly Ser Ser
                405                 410                 415

Arg Pro Ser Thr Met Gln Arg Leu His Gln Ser Thr Gly Leu Glu Thr
            420                 425                 430

Arg Ser Ser Leu Thr Lys Thr Ala Arg Asn Val His Asp Asp Pro Thr
        435                 440                 445

Leu Arg Thr Phe Glu Arg Leu Ser Ile Ser Ala Asp Arg Arg Lys
    450                 455                 460
```